US009475784B2

(12) United States Patent
Wu et al.

(10) Patent No.: US 9,475,784 B2
(45) Date of Patent: Oct. 25, 2016

(54) 4,6-DIARYLAMINOTHIAZINES AS BACE1 INHIBITORS AND THEIR USE FOR THE REDUCTION OF BETA-AMYLOID PRODUCTION

(71) Applicant: BRISTOL-MYERS SQUIBB COMPANY, Princeton, NJ (US)

(72) Inventors: Yong-Jin Wu, Madison, CT (US); Jason M. Guernon, Moodus, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/653,025

(22) PCT Filed: Dec. 19, 2012

(86) PCT No.: PCT/US2012/070546
§ 371 (c)(1),
(2) Date: Jun. 17, 2015

(87) PCT Pub. No.: WO2014/098831
PCT Pub. Date: Jun. 26, 2014

(65) Prior Publication Data
US 2015/0329506 A1    Nov. 19, 2015

(51) Int. Cl.
C07D 279/06    (2006.01)
C07D 417/10    (2006.01)
C07D 417/14    (2006.01)
C07D 417/04    (2006.01)
C07D 417/12    (2006.01)

(52) U.S. Cl.
CPC ........... C07D 279/06 (2013.01); C07D 417/04 (2013.01); C07D 417/10 (2013.01); C07D 417/12 (2013.01); C07D 417/14 (2013.01)

(58) Field of Classification Search
CPC .......................... C07D 279/06; C07D 417/10
USPC .................. 514/224.2, 227.2; 544/47, 53
See application file for complete search history.

(56) References Cited

U.S. PATENT DOCUMENTS 8,653,067 B2 *  2/2014  Kobayashi ........... C07D 239/14
514/211.01

FOREIGN PATENT DOCUMENTS

| EP | 1 942 105 A1 | 7/2008 | |
| EP | 2 151 435 A1 | 2/2010 | |
| JP | WO 2008133273 A1 * | 11/2008 | ........... C07D 239/14 |
| WO | WO 2011/005738 A1 | 1/2011 | |

OTHER PUBLICATIONS

Zhu et al. Organic Letters (2006), 8(12), 2599-2602.*

"Consensus Recommendations for the Postmortem Diagnosis of Alzheimer's Disease," Neurobiology of Aging, vol. 18, No. S4, pp. S1-S2, 1997.
Anderson, D.H. et al., "Characterization of β amyloid assemblies in drusen: the deposits associated with aging and age-related macular degeneration," Experimental Eye Research, 78, pp. 243-256, 2004.
Cleary, J.P. et al., "Natural oligomers of the amyloid-β protein specifically disrupt cognitive function," Nature Neuroscience, vol. 8, No. 1, pp. 79-84, Jan. 2005.
Davis F.A. et al., "Direct Asymmetric Synthesis of β-Amino Ketones from Sulfinimines (N-Sulfinylimines). Synthesis of (-)-indolizidine 209B," Organic Letters, vol. 5, No. 26, pp. 5011-5014, 2003.
Deramecourt V. et al., "Biochemical staging of Synucleinopathy and Amyloid Deposition in Dementia with Lewy Bodies," Journal of Neuropathology and Experimental Neurol., vol. 65, No. 3, pp. 278-288, Mar. 2006.
Goldstein L.E. et al., "Cytosolic β-amyloid deposition and supranuclear cataracts in lenses from people with Alzheimer's disease," The Lancet, vol. 361, pp. 1258-1265, Apr. 12, 2003.

(Continued)

*Primary Examiner* — Kahsay Habte
(74) *Attorney, Agent, or Firm* — John F. Levis

(57) ABSTRACT

Compounds of formula (I), including pharmaceutically acceptable salts thereof, are set forth herein: wherein $R^1$ and $R^2$ are independently hydrogen, or —$CH_3$; or $R^1$ and $R^2$ can join together in a ring by adding —$(CH_2)_4$—; $R^3$ is hydrogen or $C_1$-$C_3$ alkyl; Y and Z are independently a $C_6$-$C_{10}$-aryl group or a 5-10 membered heterocyclic group which can be further substituted with from 0-3 substituents selected from the group of halogen, hydroxy, amino, $C_{1-4}$alkylamino, $C_{1-4}$dialkylamino, halo$C_{1-4}$ alkyl, CN, $C_1$-$C_6$ alkyl or cycloalkyl, $C_1$-$C_6$ alkoxy, —C=O$C_{1-4}$alkyl, —$SO_2C_{1-4}$alkyl, and $C_2$-$C_4$ alkynyl; A is selected from the group of phenyl, benzyl, oxazolyl, thiazolyl, isoxazolyl, imidazolyl, pyrazolyl, pyridyl, pyrimidinyl, and pyrazinyl groups which can be further substituted with from 0-3 substituents selected from the group of halogen, hydroxy, amino, $C_{1-4}$alkylamino, $C_{1-4}$dialkylamino, halo$C_{1-4}$ alkyl, hydroxy$C_{1-6}$ alkyl, CN, $C_1$-$C_6$ alkyl or cycloalkyl, $C_1$-$C_6$ alkoxy, and $C_2$-$C_4$ alkynyl; L is —NHCO— or is a single bond; and L and Z together can be absent.

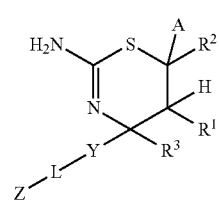

I

23 Claims, No Drawings

(56) References Cited

OTHER PUBLICATIONS

Grundman M et al., "Mild Cognitive Impairment Can Be Distinguished from Alzheimer Disease and Normal Aging for Clinical Trials," Archives of Neurology, vol. 61, pp. 59-66, Jan. 2004.

Hamilton R.L. et al., "Alzheimer disease pathology in amyotrophic lateral sclerosis," Acta Neuropathology, 107, pp. 515-522, 2004.

Loane D.J. et al., "Amyloid precursor protein secretases as therapeutic targets for traumatic brain injury," Nature Medicine, vol. 15, No. 4, pp. 377-379, Apr. 2009.

Hussain I. et al., "Identification of a Novel Aspartic Protease (Asp 2) as β-Secretase," Molecular and Cellular Neuroscience, 14, pp. 419-427, 1999.

Klapars A. et al., "A General and Efficient Copper Catalyst for the Amidation of aryl Halides," J. Am. Chem. Soc., vol. 124, No. 25, pp. 7421-7428, 2002.

Lin X. et al., Human aspartic protease memapsin 2 cleaves the β-secretase site of β-amyloid precursor protein, Proc. Natl. Acad. Sci., vol. 97, No. 4, pp. 1456-1460, Feb. 15, 2000.

Luo Y. et al., "Mice deficient in BACE1, the Alzheimer's β-secretase, have normal phenotype and abolished β-amyloid generation," Nature Neuroscience, vol. 4, No. 3, pp. 231-232, Mar. 2001.

Murphy, M.P. et al., "Inclusion-body myositis and Alzheimer disease: Two sides of the same coin, or different currencies altogether?" Neurology, 66, Suppl 1, pp. S65-S68, 2006.

Neumann M. et al., Ubiquitinated TDP-43 in Frontotemporal Lobar Degeneration and Amyotrophic Lateral Sclerosis, Science, vol. 314, pp. 130-133, Oct. 6, 2006.

Roberds S.L. et al., "BACE knockout mice are healthy despite lacking the primary β-secretase activity in brain: implications for Alzheimer's disease therapeutics," Human Molecular Genetics, vol. 10, No. 12, pp. 1317-1324, 2001.

Selkoe D.J., "Alzheimer's Disease: Genes, Proteins, and Therapy," Physiological Reviews, vol. 81, No. 2, pp. 741-766, Apr. 2001.

Sinha S. et al., "Purification and cloning of amyloid precursor protein β-secretase from human brain," Nature, vol. 402, pp. 537-540, Dec. 2, 1999.

Tang T.P. et al., "Asymmetric Synthesis of β-Amino Acid Derivatives Incorporating a Broad Range of Substitution Patterns by Enolate Additions to tert-Butanesulfinyl Imines," J. Org. Chem., 67, pp. 7819-7832, 2002.

Thal D.R. et al., "Two Types of Sporadic Cerebral Amyloid Angiopathy," Journal of Neuropathology and Experimental Neurology, vol. 61, No. 3, pp. 282-293, Mar. 2002.

Vassar R. et al., "β-Secretase Cleavage of Alzheimer's Amyloid Precursor Protein by the Transmembrane Aspartic Protease BACE," Science, vol. 286, pp. 735-741, Oct. 22, 1999.

Walsh D.M. et al., "Deciphering the Molecular Basis of Memory Failure in Alzheimer's Disease," Neuron, vol. 44, pp. 181-193, Sep. 30, 2004.

Wolfe M.S. et al., "Intramembrane Proteolysis: Theme and Variations," Science, vol. 305, pp. 1119-1123, Aug. 20, 2004.

Wolfe M.S., "Secretase Targets for Alzheimer's Disease, Identification and Therapeutic Potential," Journal of Medicinal Chemistry, vol. 44, No. 13, pp. 2039-2060, Jun. 21, 2001.

Yokota O. et al., "NACP/α-Synuclein, NAC, and β-amyloid pathology of familial Alzheimer's disease with the E184D presenilin-1 mutation: a clinicopathological study of two autopsy cases," Acta Neuropathol, 104, pp. 637-648, 2002.

Yoshida T. et al., "The potential role of amyloid β in the pathogenesis of age-related macular degeneration," The Journal of Clinical Investigation, vol. 115, No. 10, pp. 2793-2800, Oct. 2005.

Wan J.-P. et al., Microwave-Assisted Three-Component Reaction for Rapid Synthesis of Some 5,6-Dihydro-4H-1,3-Thiazine Derivatives Under Solvent-Free Conditions, Synthetic Communications, 40, pp. 709-716, 2010.

Yan R. et al., "Membrane-anchored aspartyl protease with Alzheimer's disease β-secretase activity," Nature, vol. 402, pp. 533-537, Dec. 2, 1999.

Zhu Y. et al., "Two Novel Diastereoselective Three-Component Reactions of Alkenes or 3,4-Dihydro-(2H)-pyran with Urea/thiourea-Aldehyde Mixtures, [4+2] Cycloaddition vs Viginelli-Type Reaction," Organic Letters, vol. 8, No. 12, pp. 2599-2602, 2006.

\* cited by examiner

4,6-DIARYLAMINOTHIAZINES AS BACE1 INHIBITORS AND THEIR USE FOR THE REDUCTION OF BETA-AMYLOID PRODUCTION

FIELD OF THE INVENTION

The present invention relates to compounds which are inhibitors of β-amyloid peptide (Aβ) production, as well as to methods of treating Alzheimer's Disease (AD) and other conditions related to β-amyloid production using compounds which are inhibitors of β-amyloid peptide (Aβ) production. The invention further relates to pharmaceutical compositions comprising these compounds.

BACKGROUND OF THE INVENTION

Alzheimer's disease (AD) is a progressive neurodegenerative disease which begins with memory loss and progresses to include severe cognitive impairment, altered behavior, and decreased motor function (Grundman, M. et al., *Arch Neurol*. (2004) 61: 59-66; Walsh, D. M. et al., *Neuron* (2004) 44: 181-193). It is the most common form of dementia and represents the third leading cause of death after cardiovascular disorders and cancer. The cost of AD is enormous and includes the suffering of the patients and families and the lost productivity of patients and caregivers. No treatment that effectively prevents AD or reverses the clinical symptoms and underlying pathophysiology is currently available.

A definitive diagnosis of AD for a demented patient requires a histopathological evaluation of the number and localization of neuritic plaques and neurofibrillary tangles upon autopsy (Consensus recommendations for the postmortem diagnosis of Alzheimer's disease. *Neurobiol Aging* (1997) 18: S1-2). Similar alterations are observed in patients with Trisomy 21 (Down syndrome). Plaques primarily consist of β-amyloid (Aβ) peptides that are formed by a stepwise proteolytic cleavage of the amyloid precursor protein (APP) by β-site APP-cleaving enzyme 1 (BACE1), to generate the N-terminus, and γ-secretase, to generate the C-terminus (Selkoe, D. J., *Physiol Rev*. (2001) 81: 741-766). γ-Secretase is a transmembrane protein complex that includes Nicastrin, Aph-1, PEN-2, and either Presenilin-1 (PS-1) or Presenilin-2 (PS-2) (Wolfe, M. S. et al., *Science* (2004) 305: 1119-1123). PS-1 and PS-2 are believed to contain the catalytic sites of γ-secretase. The BACE1 enzyme is a transmembrane aspartyl protease and was described in the literature by several independent groups [see Hussain, I. et al., (1999) *Mol. Cell. Neurosci.*, 14: 419-427; Lin, X. et al., (2000) *Proceedings of the National Academy of Sciences of the United States of America*, 97: 1456-1460; Sinha, S., et al., (1999) *Nature* (London), 402: 537-540; Vassar, R., et al., (1999) *Science* (Washington, D.C.), 286: 735-741; Walsh, D. M. et al., (2002); Wolfe, M. S. (2001); Yan, R. et al., (1999) *Nature* (London), 402: 533-537].

Aβ40 is the most abundant form of Aβ synthesized (80-90%), while Aβ42 is most closely linked with AD pathogenesis. In particular, mutations in the APP, PS-1, and PS-2 genes that lead to rare, familial forms of AD implicate Aβ42 aggregates as the primary toxic species (Selkoe, D. J., *Physiol Rev.*, (2001) 81: 741-766). Current evidence suggests that oligomeric, protofibrillar and intracellular Aβ42 play a significant role in the disease process (Cleary, J. P. et al., *Nat Neurosci*. (2005) 8: 79-84). Inhibitors of the enzymes that form Aβ42, such as BACE1, represent potential disease-modifying therapeutics for the treatment of AD.

Evidence suggests that a reduction in brain Aβ levels by inhibition of BACE may prevent the onset and progression of AD (Selkoe, D. *Physiol. Rev.* (2001) 81: 741-766; Wolfe, M., *J. Med. Chem*. (2001) 44: 2039-2060). There are emerging data for the role of Aβ in other diseases, including mild cognitive impairment (MCI), Down syndrome, cerebral amyloid angiopathy (CAA), dementia with Lewy bodies (DLB), amyotrophic lateral sclerosis (ALS-D), inclusion body myositis (IBM), and age-related macular degeneration. Advantageously, compounds that inhibit BACE1 and reduce production of Aβ could be used to treat these or other Aβ-dependent diseases.

Excess production and/or reduced clearance of Aβ causes CAA (Thal, D. et al., *J. Neuropath. Exp. Neuro*. (2002) 61: 282-293). In these patients, vascular amyloid deposits cause degeneration of vessel walls and aneurysms that may be responsible for 10-15% of hemorrhagic strokes in elderly patients. As in AD, mutations in the gene encoding Aβ lead to an early onset form of CAA, referred to as cerebral hemorrhage with amyloidosis of the Dutch type, and mice expressing this mutant protein develop CAA that is similar to patients. Compounds that reduce Aβ levels could reduce or prevent CAA.

DLB manifests with visual hallucinations, delusions, and parkinsonism. Interestingly, familial AD mutations that cause Aβ deposits can also cause Lewy bodies and DLB symptoms (Yokota, O. et al., *Acta Neuropathol* (*Berl*) (2002) 104: 637-648). Further, sporadic DLB patients have Aβ deposits similar to those in AD (Deramecourt, V. et al., *J Neuropathol Exp Neurol* (2006) 65: 278-288). Based on this data, Aβ likely drives Lewy body pathology in DLB and, therefore, compounds that reduce Aβ levels could reduce or prevent DLB.

Approximately 25% of ALS patients have significant dementia or aphasia (Hamilton, R. L. et al., *Acta Neuropathol* (*Berl*) (2004) 107: 515-522). The majority (~60%) of these patients, designated ALS-D, contain ubiquitin-positive inclusions comprised primarily of the TDP-43 protein (Neumann, M. et al., *Science* (2006) 314: 130-133). About 30% of the ALS-D patients have amyloid plaques consistent with Aβ causing their dementia (Hamilton, R. L. et al., *Acta Neuropathol* (*Berl*) (2004) 107: 515-522). These patients should be identifiable with amyloid imaging agents and potentially could be treated by compounds that reduce Aβ levels.

IBM is a rare, age-related degenerative disease of skeletal muscle. The appearance of Aβ deposits in IBM muscle and the recapitulation of several aspects of the disease by directing APP overexpression to muscle in transgenic mice support the role of Aβ in IBM (reviewed in Murphy, M. P. et al., *Neurology* (2006) 66: S65-68). Compounds that reduce Aβ levels could reduce or prevent IBM.

In age-related macular degeneration, Aβ was identified as one of several components of drusen, extracellular deposits beneath the retinal pigment epithelium (RPE) (Anderson, D. H. et al., *Exp Eye Res* (2004) 78: 243-256). A recent study has shown potential links between Aβ and macular degeneration in mice (Yoshida, T. et al., *J Clin Invest* (2005) 115: 2793-2800). Increases in Aβ deposition and supranuclear cataracts have been found in AD patients (Goldstein, L. E. et al., *Lancet* (2003) 361: 1258-1265). Compounds that reduce Aβ levels could reduce or prevent age-related macular degeneration.

A recent study by Georgetown University Medical Center researchers suggests that BACE1 inhibitors may prevent long-term damage from traumatic brain injury (Loane, D. J., et al., *Nature Medicine* (2009) 15: 377-379).

A logical approach to reducing Aβ levels is to block the action of the secretases. The β-secretase enzyme (BACE) is responsible for cleaving APP and forms the amino-terminus of Aβ, initiating the amyloidogenic pathway. Removal of BACE activity in mice by gene targeting completely abolishes Aβ production [see Luo, Y., et al., (2001) *Nature Neuroscience*, 4: 231-232; Roberds, S. L. et al., (2001) *Human Molecular Genetics*, 10: 1317-1324]. BACE –/– mice also show no significant negative phenotypes, suggesting that disruption of BACE-mediated cleavage of APP does not produce additional undesired effects. Thus, compounds that reduce Aβ1-42 production and their pharmaceutical compositions are beneficial agents that will prevent damage from overproduction of Aβ and are useful in treating Alzheimer's disease, Down syndrome, CAA, and inclusion body myositis, DLB, and other disorders where Aβ is overproduced.

PCT Publication WO 2011/005738, published Jan. 13, 2011, discloses BACE inhibitors.

What is therefore needed in the art are new compounds that inhibit β-amyloid peptide (Aβ) production, as well as compositions containing these compounds, and methods of treatment which utilize these compounds.

SUMMARY OF THE INVENTION

In its first aspect, the present invention provides a compound of formula (I), including pharmaceutically acceptable salts thereof:

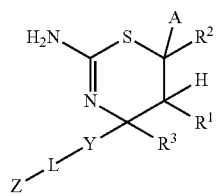

I wherein $R^1$ and $R^2$ are independently hydrogen or —$CH_3$; or $R^1$ and $R^2$ can join together in a ring by adding —$(CH_2)_4$—;
$R^3$ is hydrogen, or $C_1$-$C_3$ alkyl;
Y and Z are independently a $C_6$-$C_{10}$-aryl group or a 5-10 membered heterocyclic group which can be further substituted with from 0-3 substituents selected from the group of halogen, hydroxy, amino, $C_{1-4}$alkylamino, $C_{1-4}$dialkylamino, halo$C_{1-4}$ alkyl, CN, $C_1$-$C_6$ alkyl or cycloalkyl, $C_1$-$C_6$ alkoxy, —C=O$C_{1-4}$alkyl, —$SO_2C_{1-4}$alkyl, and $C_2$-$C_4$ alkynyl;
A is selected from the group of phenyl, benzyl, oxazolyl, thiazolyl, isoxazolyl, imidazolyl, pyrazolyl, pyridyl, pyrimidinyl, and pyrazinyl groups which can be further substituted with from 0-3 substituents selected from the group of halogen, hydroxy, amino, $C_{1-4}$alkylamino, $C_{1-4}$dialkylamino, halo$C_{1-4}$ alkyl, hydroxy$C_{1-6}$alkyl, CN, $C_1$-$C_6$ alkyl or cycloalkyl, $C_1$-$C_6$ alkoxy, and $C_2$-$C_4$ alkynyl;
L is —NHCO—, or is a single bond; and
L and Z together can be absent.

In a second aspect, the present invention provides a pharmaceutical composition for the treatment of disorders responsive to the reduction of β-amyloid peptide production comprising a therapeutically effective amount of a compound of formula (I), including pharmaceutically acceptable salts thereof, in association with a pharmaceutically acceptable carrier or diluent.

In a third aspect, the present invention provides a method for the treatment of disorders responsive to the reduction of β-amyloid peptide production in a mammal in need thereof, which comprises administering to said mammal a therapeutically effective amount of a compound of formula (I), including pharmaceutically salts thereof. In a first embodiment of the first aspect said disorder is selected from Alzheimer's Disease (AD), Down Syndrome, mild cognitive impairment (MCI), cerebral amyloid angiopathy (CAA), dementia with Lewy bodies (DLB), amyotrophic lateral sclerosis (ALS-D), inclusion body myositis (IBM), age-related macular degeneration, and cancer. In a second embodiment of the third aspect, said disorder is selected from Alzheimer's Disease and Down Syndrome. In a third embodiment of the third aspect, said disorder is Alzheimer's Disease.

Other aspects of the present invention may include suitable combinations of embodiments set forth herein.

Yet other aspects and embodiments may be found in the description provided herein.

DETAILED DESCRIPTION OF THE EMBODIMENTS

The description of the present disclosure herein should be construed in congruity with the laws and principals of chemical bonding. In some instances it may be necessary to remove a hydrogen atom in order to accommodate a substituent at any given location.

It should be understood that the compounds encompassed by the present disclosure are those that are suitably stable for use as pharmaceutical agent.

It is intended that the definition of any substituent or variable at a particular location in a molecule be independent of its definitions elsewhere in that molecule.

All patents, patent applications, and literature references cited in the specification are herein incorporated by reference in their entirety. In the case of inconsistencies, the present disclosure, including definitions, will prevail.

In some instances, the number of carbon atoms in any particular group is denoted before the recitation of the group. For example, the term "halo$C_{1-6}$alkoxy" denotes a haloalkoxy group containing one to six carbon atoms and the term "$C_{1-4}$alkoxy$C_{1-2}$alkyl" denotes an alkoxy group containing one to four alkoxy groups attached to the parent molecular moiety through an alkyl group of one or two carbon atoms. Where these designations exist they supersede all other definitions contained herein.

As used herein and unless otherwise expressly set forth elsewhere in the application, the following terms shall have the following meanings:

As used herein, the singular forms "a", "an", and "the" include plural reference unless the context clearly dictates otherwise.

The term "alkoxy," as used herein, refers to an alkyl group attached to the parent molecular moiety through an oxygen atom.

The term "alkoxyalkyl," as used herein, refers to an alkyl group substituted with one, two, or three alkoxy groups.

The term "alkoxyalkylcarbonyl," as used herein, refers to an alkoxyalkyl group attached to the parent molecular moiety through a carbonyl group.

The term "alkoxycarbonyl," as used herein, refers to an alkoxy group attached to the parent molecular moiety through a carbonyl group.

The term "alkyl," as used herein, refers to a group derived from a straight or branched chain saturated hydrocarbon containing from one to ten carbon atoms.

The term "alkylamino," as used herein, refers to —NHR$^x$, wherein R$^x$ is an alkyl group.

The term "alkylaminoalkoxy," as used herein, refers to an alkylamino group attached to the parent molecular moiety through an alkoxy group.

The term "alkylcarbonyl," as used herein, refers to an alkyl group attached to the parent molecular moiety through a carbonyl group.

The term "alkylsulfonyl," as used herein, refers to an alkyl group attached to the parent molecular moiety through a sulfonyl group.

The term "alkylsulfonylamido," as used herein refers to —C(O)NHS(O)$_2$R$^x$ wherein R$^x$ is an alkyl group.

The term "amino," as used herein, refers to —NH$_2$.

The term "carbonyl," as used herein, refers to —C(O)—.

The term "cyano," as used herein, refers to —CN.

The term "cycloalkyl," as used herein, refers to a saturated monocyclic hydrocarbon ring system having three to fourteen carbon atoms and zero heteroatoms.

The term "(cycloalkyl)alkyl," as used herein, refers to an alkyl group substituted with one, two, or three cycloalkyl groups.

The term "cycloalkylamino," as used herein, refers to —NHR$^x$ wherein Rx is a cycloalkyl group.

The term "cycloalkylcarbonyl," as used herein, refers to a cycloalkyl group attached to the parent molecular moiety through a carbonyl group.

The term "cycloalkylsulfonyl," as used herein, refers to a cycloalkyl group attached to the parent molecular moiety through a sulfonyl group.

The term "dialkylamino," as used herein, refers to —NR$^x$R$^y$, wherein R$^x$ and R$^y$ are each alkyl groups.

The term "dialkylaminoalkoxy," as used herein, refers to a dialkylamino group attached to the parent molecular moiety through an alkoxy group.

The term "dialkylaminoalkyl," as used herein, refers to an alkyl group substituted with one, two, or three dialkylamino groups.

The term "dialkylaminoalkylcarbonyl," as used herein, refers to a dialkylaminoalkyl group attached to the parent molecular moiety through a carbonyl group.

The term "H", as used herein, refers to hydrogen, including its isotopes.

The terms "halo" and "halogen," as used herein, refer to F, Cl, Br, and I.

The term "haloalkoxy," as used herein, refers to a haloalkyl group attached to the parent molecular moiety through an oxygen atom.

The term "haloalkyl," as used herein, refers to an alkyl group substituted with one, two, three, or four halogen atoms.

The term "hydroxy," as used herein, refers to —OH.

The term "hydroxyalkyl," as used herein, refers to an alkyl group substituted with one, two, or three hydroxy groups.

The term "methylamino," as used herein, refers to —NHCH$_3$.

The term "oxo," as used herein, refers to =O.

The term "sulfonyl," as used herein, refers to —SO$_2$—.

It should be understood that the disclosure encompasses all stereochemical forms, or mixtures thereof, which possess the ability to reduce β-amyloid peptide production.

Certain compounds of the present invention may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

The present disclosure is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Certain compounds of the present invention may exist in zwitterionic form and the present disclosure includes each zwitterionic form of these compounds and mixtures thereof.

The compounds of the present invention can exist as pharmaceutically acceptable salts. The term "pharmaceutically acceptable salt," as used herein, represents salts or zwitterionic forms of the compounds of the present invention which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methyl-amine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

As set forth above, the present invention provides a compound of formula (I), including pharmaceutically acceptable salts thereof:

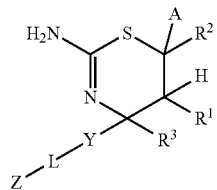

I wherein $R^1$ and $R^2$ are independently hydrogen or $CH_3$;
or $R^1$ and $R^2$ can join together in a ring by adding —$(CH_2)_4$—;
$R^3$ is hydrogen or $C_1$-$C_3$ alkyl;
Y and Z are independently a $C_6$-$C_{10}$-aryl group or a 5-10 membered heterocyclic group which can be further substituted with from 0-3 substituents selected from the group of halogen, hydroxy, amino, $C_{1-4}$alkylamino, $C_{1-4}$dialkylamino, halo$C_{1-4}$ alkyl, CN, $C_1$-$C_6$ alkyl or cycloalkyl, $C_1$-$C_6$ alkoxy, —C=O$C_{1-4}$alkyl, —$SO_2C_{1-4}$alkyl, and $C_2$-$C_4$ alkynyl;
A is selected from the group of phenyl, benzyl, oxazolyl, thiazolyl, isoxazolyl, imidazolyl, pyrazolyl, pyridyl, pyrimidinyl, and pyrazinyl groups which can be further substituted with from 0-3 substituents selected from the group of halogen, hydroxy, amino, $C_{1-4}$alkylamino, $C_{1-4}$dialkylamino, halo$C_{1-4}$ alkyl, hydroxy$C_{1-6}$alkyl, CN, $C_1$-$C_6$ alkyl or cycloalkyl, $C_1$-$C_6$ alkoxy, and $C_2$-$C_4$ alkynyl;
L is —NHCO—, or is a single bond; and
L and Z together can be absent.

In a further embodiment of the invention, $R^1$ and $R^2$ are independently hydrogen or $CH_3$;
or $R^1$ and $R^2$ can join together in a ring by adding —$(CH_2)_4$—;
$R^3$ is hydrogen, methyl or ethyl;
Y is phenyl or thiophenyl and Z is a pyridyl, pyrimidinyl or pyrazinyl group in which either Y or Z group can be further substituted with from 0-3 substituents selected from halogen, hydroxyl, amino, $C_{1-4}$alkylamino, $C_{1-4}$dialkylamino, halo$C_{1-4}$ alkyl, CN, $C_1$-$C_6$ alkyl or cycloalkyl, $C_1$-$C_6$ alkoxy, or $C_2$-$C_4$ alkynyl;
A is selected from the group of phenyl, benzyl, oxazolyl, thiazolyl, isoxazolyl, imidazolyl, pyrazolyl, pyridyl, pyrimidinyl, pyrazinyl, groups which can be further substituted with from 0-3 substituents selected from the group of halogen, hydroxy, amino, $C_{1-4}$alkylamino, $C_{1-4}$dialkylamino, halo$C_{1-4}$ alkyl, hydroxy$C_{1-6}$alkyl, CN, $C_1$-$C_6$ alkyl or cycloalkyl, $C_1$-$C_6$ alkoxy, and $C_2$-$C_4$ alkynyl;
L is —NHCO— or is a single bond; and
L and Z together can be absent.

In another embodiment, $R^1$ and $R^2$ are independently hydrogen;
$R^3$ is hydrogen or methyl;
Y is a phenyl or thiophenyl group which can be substituted with from 0-3 halogen, methyl, or trifluoromethyl substituents; Z is a pyridyl, pyrimidinyl or pyrazinyl group which can be substituted with form 0-3 substituents selected from halogen, CN, or $C_2$-$C_4$ alkynyl;
A is selected from the group of oxazolyl, thiazolyl, isoxazolyl, pyrazolyl, or pyrimidinyl which can be further substituted with from 0-3 halogen, $C_1$-$C_6$ alkoxy, halo$C_{1-4}$ alkyl or $C_1$-$C_6$ alkyl substituents;
L is —NHCO— or is a single bond; and
L and Z together can be absent.

In a further embodiment, $R^1$ and $R^2$ are independently hydrogen;
$R^3$ is hydrogen, methyl or fluorinated methyl.
Y is a phenyl or thiophenyl group which can be substituted with from 0-3 halogen, methyl, or trifluoromethyl substituents;
Z is a pyridyl, pyrimidinyl or pyrazinyl group which can be substituted with form 0-3 substituents selected from halogen, CN, or C2-C4 alkynyl;
A is isoxazolyl which can be further substituted with from 0-3 $C_1$-$C_6$ alkyl substituents;
L is —NHCO— or is a single bond; and
L and Z together can be absent.

In another embodiment of the invention, $R^1$ and $R^2$ are independently hydrogen;
$R^3$ is hydrogen or methyl;
Y is a phenyl or thiophenyl group which can be substituted with from 0-3 halogen substituents;
Z is a pyridyl, pyrimidinyl or pyrazinyl group which can be substituted with form 0-3 substituents selected from halogen, CN, or $C_2$-$C_4$ alkynyl;
A is isoxazolyl, pyrazolyl, or pyrimidinyl which can be further substituted with from 0-3 $C_1$-$C_6$ alkyl substituents;
L is —NHCO— or is a single bond; and
L and Z together can be absent.

In a further embodiment, $R^1$ and $R^2$ are independently hydrogen;
$R^3$ is hydrogen or methyl;
Y is a phenyl or thiophenyl group which can be substituted with from 0-3 halogen substituents;
Z is a pyridyl group which can be further substituted with from 0-3 substituents selected from halogen, CN or $C_2$-$C_4$ alkynyl;
A is isoxazolyl, pyrazolyl, or pyrimidinyl which can be further substituted with from 0-3 $C_1$-$C_6$ alkyl substituents; and L is —HNCO—.

In another embodiment, $R^1$ and $R^2$ are independently hydrogen;
$R^3$ is hydrogen or methyl;
Y is a phenyl or thiophenyl group which can be substituted with from 0-3 halogen substituents;
Z is pyrimidin-5-yl or pyridin-5-yl;
A is isoxazolyl, pyrazolyl, or pyrimidinyl which can be further substituted with from 0-3 $C_1$-$C_6$ alkyl substituents; and
and L is a single bond.

In another embodiment, $R^1$ and $R^2$ are independently hydrogen;
$R^3$ is hydrogen or methyl;
Y is a phenyl or thiophenyl group which can be substituted with from 0-3 halogen substituents;
A is isoxazolyl, pyrazolyl, or pyrimidinyl which can be further substituted with from 0-3 $C_1$-$C_6$ alkyl substituents; and
and L and Z together are absent.

Also preferred are compounds of formula (I) wherein the Y-L-Z substituent and ring A are trans to each other, and the configuration of the chiral center adjacent to the nitrogen of the aminothiazine is (S).

In addition, the following compounds, including pharmaceutically salts thereof, are also preferred which are selected from the group of:

N-(3-((4S,6S)-2-amino-6-(3,5-dimethylisoxazol-4-yl)-4-methyl-5,6-dihydro-4H-1,3-thiazin-4-yl)-4-fluorophenyl)-5-chloropicolinamide;

N-(3-((4S,6S)-2-amino-6-(3,5-dimethylisoxazol-4-yl)-4-methyl-5,6-dihydro-4H-1,3-thiazin-4-yl)-4-fluorophenyl)-5-cyanopicolinamide;

N-(3-((4S,6S)-2-amino-6-(3,5-dimethylisoxazol-4-yl)-4-methyl-5,6-dihydro-4H-1,3-thiazin-4-yl)-4-fluorophenyl)-5-fluoropicolinamide;

N-(3-((4S,6S)-2-amino-6-(3,5-dimethylisoxazol-4-yl)-4-methyl-5,6-dihydro-4H-1,3-thiazin-4-yl)-4-difluoromethylphenyl)-5-cyanopicolinamide;

N-(3-((4S,6S)-2-amino-6-(3,5-dimethylisoxazol-4-yl)-5,6-dihydro-4H-1,3-thiazin-4-yl)-4-fluorophenyl)-5-chloropicolinamide;

N-(3-((4S,6S)-2-amino-6-(3,5-dimethylisoxazol-4-yl)-5,6-dihydro-4H-1,3-thiazin-4-yl)-4-fluorophenyl)-5-cyanopicolinamide;

N-(3-((4S,6S)-2-amino-6-(3,5-dimethylisoxazol-4-yl)-5,6-dihydro-4H-1,3-thiazin-4-yl)-4-fluorophenyl)-5-fluoropicolinamide;

N-(3-((4S,6S)-2-amino-6-(3,5-dimethylisoxazol-4-yl)-5,6-dihydro-4H-1,3-thiazin-4-yl)-4-fluorophenyl)-5-difluoromethylpicolinamide;

(4S,6S)-4-(3-chloro-5-(5-(prop-1-ynyl)pyridin-3-yl)thiophen-2-yl)-6-(3,5-dimethylisoxazol-4-yl)-4-methyl-5,6-dihydro-4H-1,3-thiazin-2-amine;

(4S,6S)-4-(2,4-difluoro-5-(pyrimidin-5-yl)phenyl)-6-(3,5-dimethylisoxazol-4-yl)-5,6-dihydro-4H-1,3-thiazin-2-amine;

(4S,6S)-4-(2,4-difluoro-5-(pyrimidin-5-yl)phenyl)-6-(3,5-dimethylisoxazol-4-yl)-4-methyl-5,6-dihydro-4H-1,3-thiazin-2-amine;

tert-butyl (4S,6S)-4-(3-chloro-5-(5-(prop-1-ynyl)pyridin-3-yl)thiophen-2-yl)-6-(3,5-dimethylisoxazol-4-yl)-4-methyl-5,6-dihydro-4H-1,3-thiazin-2-ylcarbamate;

(4S,6S)-4-(2,4-difluoro-5-(2-(methylsulfonyl)pyrimidin-5-yl)phenyl)-6-(3,5-dimethylisoxazol-4-yl)-4-methyl-5,6-dihydro-4H-1,3-thiazin-2-amine;

(4S,6S)-4-(2,4-difluoro-5-(2-methylpyrimidin-5-yl)phenyl)-6-(3,5-dimethylisoxazol-4-yl)-4-methyl-5,6-dihydro-4H-1,3-thiazin-2-amine;

3-(5-((4S,6S)-2-amino-6-(3,5-dimethylisoxazol-4-yl)-4-methyl-5,6-dihydro-4H-1,3-thiazin-4-yl)-2,4-difluorophenyl)picolinonitrile;

(4S,6S)-4-(2,4-difluoro-5-(6-methoxypyridin-3-yl)phenyl)-6-(3,5-dimethylisoxazol-4-yl)-4-methyl-5,6-dihydro-4H-1,3-thiazin-2-amine;

(4S,6S)-6-(3,5-dimethylisoxazol-4-yl)-4-methyl-4-(3,4,5-trifluorophenyl)-5,6-dihydro-4H-1,3-thiazin-2-amine;

(4S,6S)-4-(3,5-difluorophenyl)-6-(3,5-dimethylisoxazol-4-yl)-4-methyl-5,6-dihydro-4H-1,3-thiazin-2-amine;

(4S,6S)-4-(2,4-difluorophenyl)-6-(3,5-dimethylisoxazol-4-yl)-4-methyl-5,6-dihydro-4H-1,3-thiazin-2-amine;

(4S,6S)-4-(4-fluorophenyl)-6-(3,5-dimethylisoxazol-4-yl)-4-methyl-5,6-dihydro-4H-1,3-thiazin-2-amine;

(4S,6S)-4-(2-fluorophenyl)-6-(3,5-dimethylisoxazol-4-yl)-4-methyl-5,6-dihydro-4H-1,3-thiazin-2-amine; and 1-(4-((4S,6S)-2-amino-4-(2,4-difluorophenyl)-4-methyl-5,6-dihydro-4H-1,3-thiazin-6-yl)-3-methylisoxazol-5-yl)-2-methylpropan-2-ol.

Also preferred are the following compounds, including pharmaceutically acceptable salts thereof:

(4S,6S)-4-(2,4-difluorophenyl)-4-methyl-6-(pyrimidin-5-yl)-5,6-dihydro-4H-1,3-thiazin-2-amine;

(4S,6S)-4-(2,4-difluorophenyl)-4-methyl-6-(3-methylisoxazol-4-yl)-5,6-dihydro-4H-1,3-thiazin-2-amine; and (4S,6S)-4-(2,4-difluorophenyl)-4-methyl-6-(1-methyl-1H-pyrazol-5-yl)-5,6-dihydro-4H-1,3-thiazin-2-amine.

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the invention further provides pharmaceutical compositions, which include therapeutically effective amounts of compounds of formula (I), including pharmaceutically acceptable salts thereof, and one or more pharmaceutically acceptable carriers, diluents, or excipients. The compounds of formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of formula (I), including pharmaceutically salts thereof, with one or more pharmaceutically acceptable carriers, diluents, or excipients.

The dosage of the compounds of Formula I to achieve a therapeutic effect will depend not only on such factors as the age, weight and sex of the patient and mode of administration, but also on the degree of β-AP reduction desired and the potency of the particular compound being utilized for the particular disorder of disease concerned. It is also contemplated that the treatment and dosage of the particular compound may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

A suitable dose of a compound of Formula I or pharmaceutical composition thereof for a mammal, including man, suffering from, or likely to suffer from any condition related to β-AP production as described herein, generally the daily dose will be from about 0.05 mg/kg to about 10 mg/kg and preferably, about 0.1 to 2 mg/kg when administered parenterally. For oral administration, the dose may be in the range from about 0.1 to about 75 mg/kg and preferably from 0.1 to 10 mg/kg body weight. The active ingredient will preferably be administered in equal doses from one to four times a day. However, usually a small dosage is administered, and the dosage is gradually increased until the optimal dosage for the host under treatment is determined. In accordance with good clinical practice, it is preferred to administer the instant compounds at a concentration level that will produce an effective anti-amyloid effect without causing any harmful or untoward side effects. However, it will be understood that the amount of the compound actually administered will be determined by a physician, in the light of the relevant circumstances including the condition to be treated, the choice of compound of be administered, the chosen route of administration, the age, weight, and response of the individual patient, and the severity of the patient's symptoms.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The present invention will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

The compounds of the present application can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The compounds may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

The starting materials useful to synthesize the compounds of the present disclosure are known to those skilled in the art and can be readily manufactured or are commercially available.

The following methods set forth below are provided for illustrative purposes and are not intended to limit the scope of the claims. It will be recognized that it may be necessary to prepare such a compound in which a functional group is protected using a conventional protecting group then to remove the protecting group to provide a compound of the present disclosure. The details concerning the use of protecting groups in accordance with the present disclosure are known to those skilled in the art.

The abbreviations used in the present application, including particularly in the illustrative schemes and examples which follow, are well-known to those skilled in the art. Some of the abbreviations used are as follows:

Chemical abbreviations used in the specification and Examples are defined as follows: "dba" for dibenzylideneacetone; "t-Bu" for tert-butyl; "DCM" for dichloromethane; "DIEA" for N,N-diisopropylethylamine; "LDA" for lithium diisopropylamide; "Ph" for phenyl; "TFA" for trifluoracetic acid; "Et" for ethyl; "DMF" for N,N-dimethylformamide; "OAc" for acetate; "h" for hours, "min" for minutes; and "THF" for tetrahydrofuran.

A general synthesis of the compounds of claim 1 wherein $R^3$ is hydrogen is presented below in Scheme 1. The three-component reaction of alkene 1, aldehyde 2 and thiourea proceeds in the presence of trimethylsilyl chloride in a polar solvent such as DMF and acetonitrile under thermal conditions to give compound 3 following the procedures of Wu et. al. (Org. Lett., 2006, 8, 2599-2602).

SCHEME 1

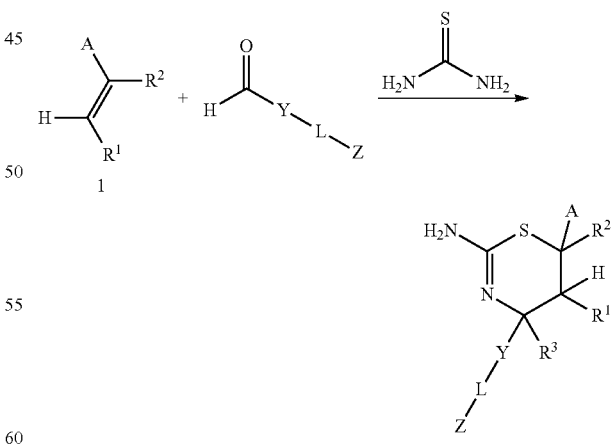

Scheme 2 describes another general synthesis of compounds of claim 1. Condensation of the carbonyl compound 4 with tert-butanesulfinamide 5 is carried out in the presence of a Lewis acid catalyst such as Ti(OEt)$_4$ to give imine 6. The enolate derived from the carbonyl compound 7 adds to imine 6 to give adduct 8. Treatment of compound 8 with lithium reagent 9 gives the Weinreb amide 10, which undergoes addition with metal reagent 11 to give ketone 12. Addition of R²Li or R²MgBr to ketone 12 produces alcohol 13, which is hydrolyzed under acidic conditions to give hydroxylamine 14. This amine reacts with benzoyl isothiocyanate to give adduct 15, which is cyclized under acidic conditions to afford compound of formula I.

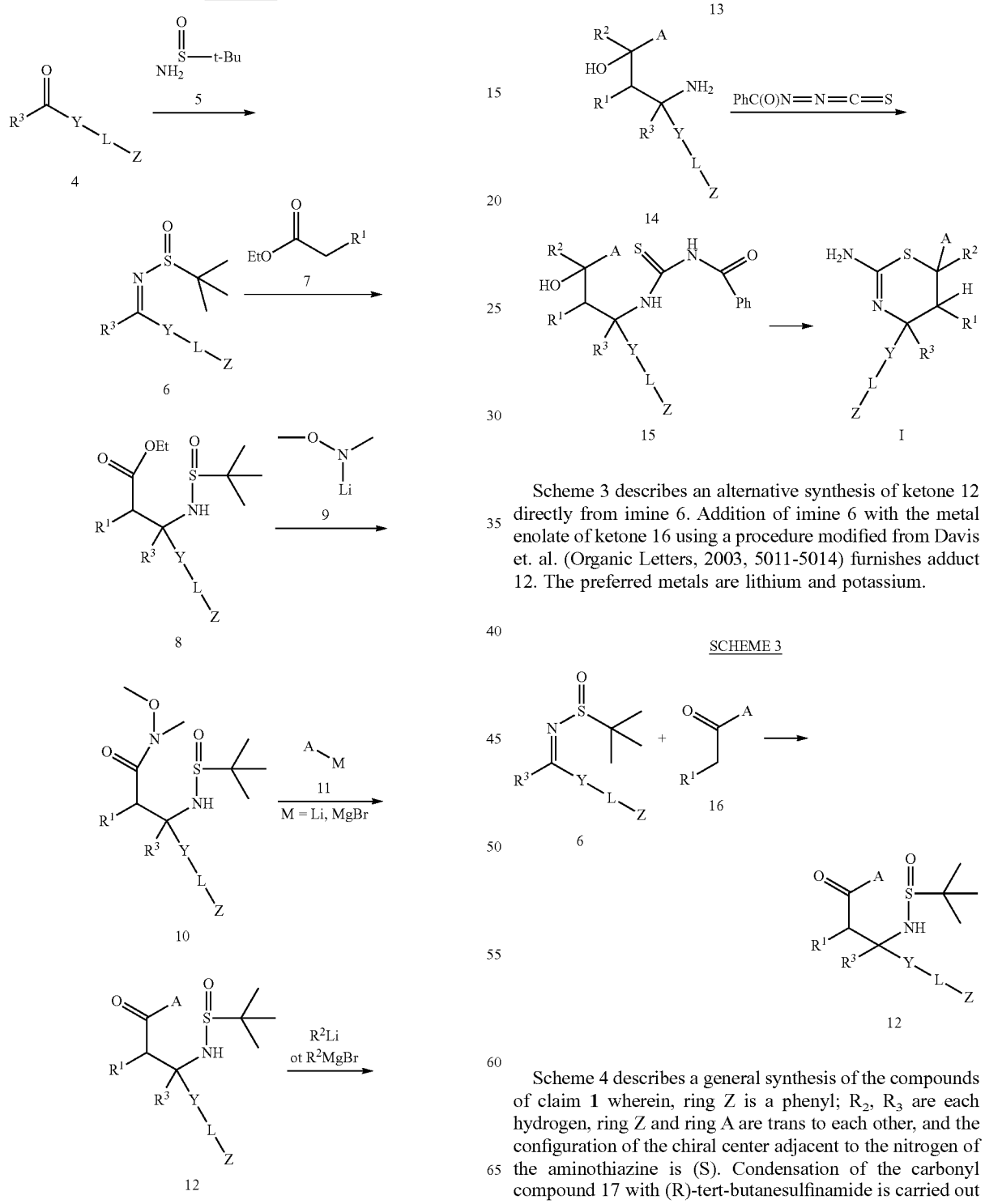

Scheme 3 describes an alternative synthesis of ketone 12 directly from imine 6. Addition of imine 6 with the metal enolate of ketone 16 using a procedure modified from Davis et. al. (Organic Letters, 2003, 5011-5014) furnishes adduct 12. The preferred metals are lithium and potassium.

Scheme 4 describes a general synthesis of the compounds of claim 1 wherein, ring Z is a phenyl; R₂, R₃ are each hydrogen, ring Z and ring A are trans to each other, and the configuration of the chiral center adjacent to the nitrogen of the aminothiazine is (S). Condensation of the carbonyl compound 17 with (R)-tert-butanesulfinamide is carried out in the presence of a Lewis acid catalyst such as Ti(OEt)₄ to give imine 18. This imine is converted to compound 20 via asymmetric addition with enolate derived from ester 19 following the procedures of Ellman et. al. (J. Org. Chem., 2002, 67, 7819). The ester group of 20 is reduced with lithium aluminum hydride to give primary alcohol 21, which undergoes hydrolysis under acidic conditions to give hydroxylamine 22. The primary amine of 22 is protected to give the NH-Boc derivative 23 under well known conditions, and the primary alcohol of 23 is oxidized using the typical Swern oxidation conditions to give aldehyde 24. Addition of this aldehyde with metal reagent 11 gives secondary alcohol 25, which is treated with acid to give primary amine 26. Treatment of this amine with reagent 15 furnishes adduct 27, which is cyclized under acidic conditions to give 28. The primary amine group of 28 is protected using the methods as described in Protecting Groups in organic Synthesis (T. W. Green and P. G. M. Wuts, 3$^{rd}$ edition, John Wiley & Sons) to give compound 29, wherein P1 is a protecting group. Coupling .reaction of amide 30 with 29 using Buchwald conditions (J. Amer. Chem. Soc. 2002, 124, 7421-7428) gives 31, which is deprotected to give 32. Suzuki reaction of 29 with boronic acid 33 gives 34, which is deprotected to give 35.

SCHEME 4

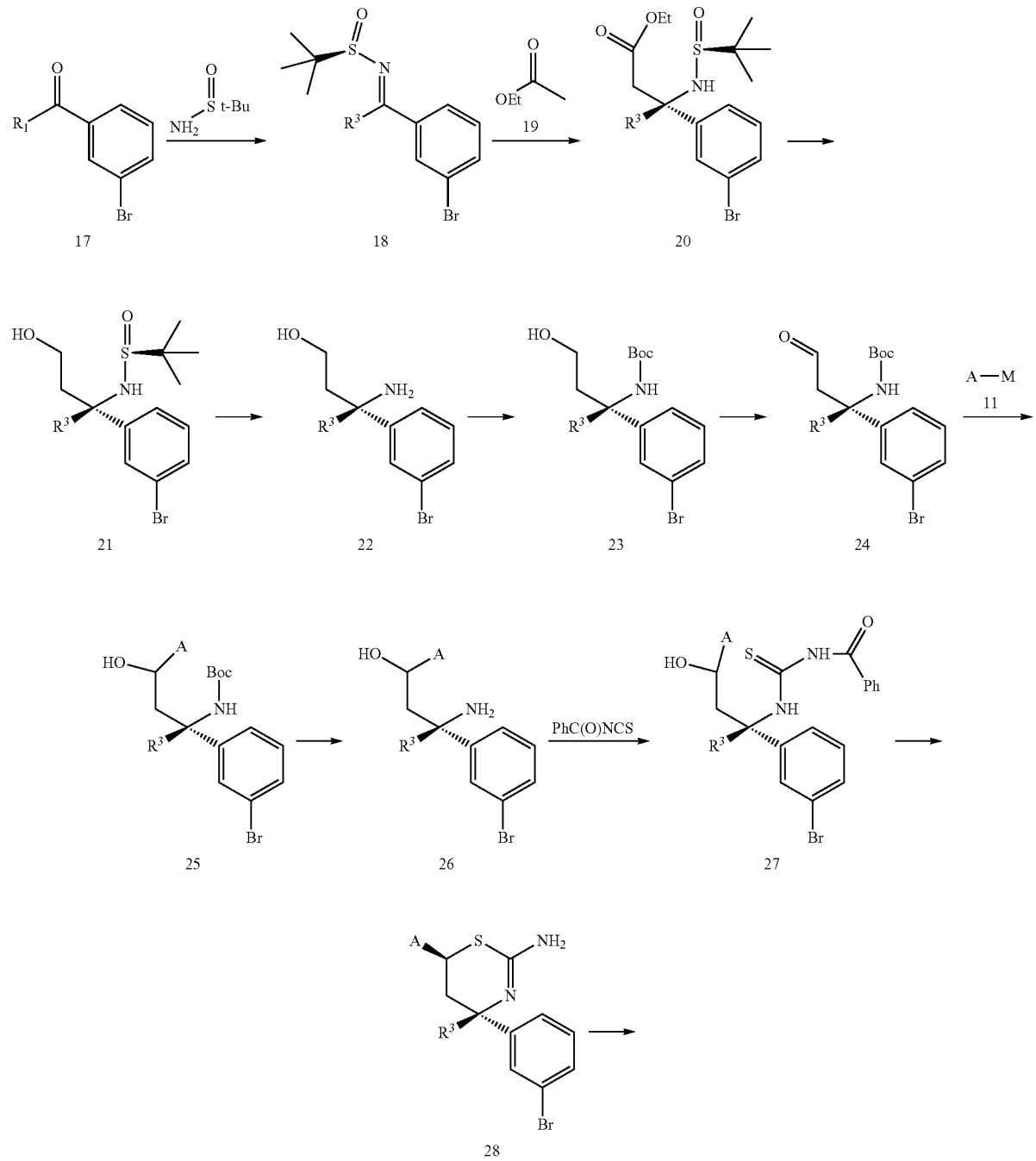

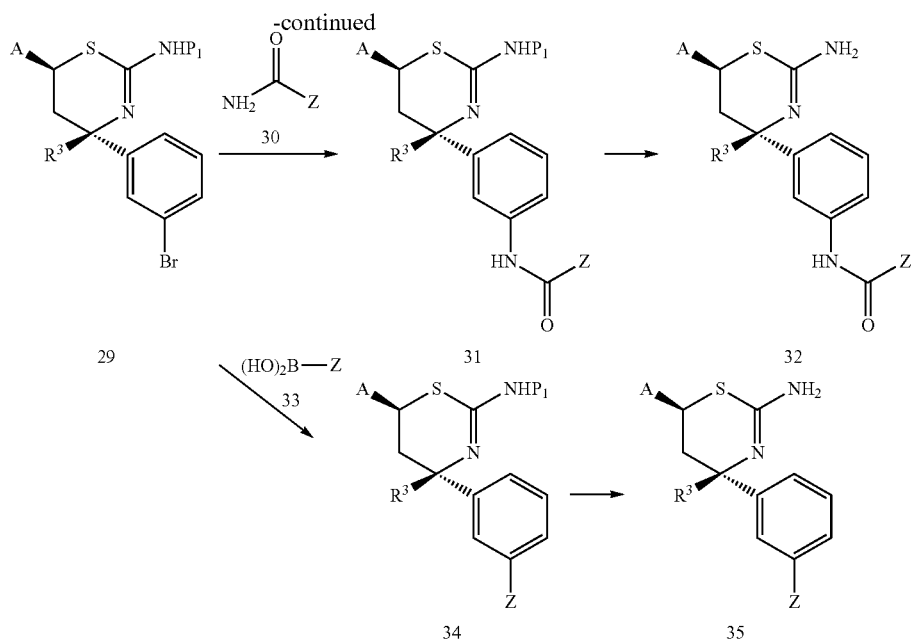

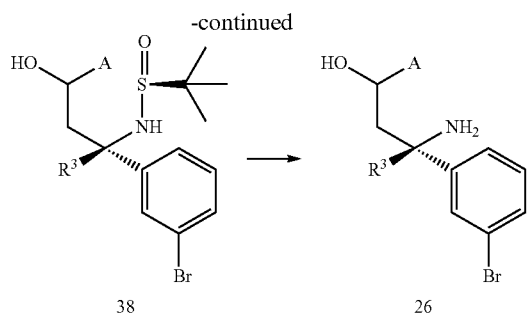

Scheme 5 describes a general synthesis of intermediate 26 shown in Scheme 4. The lithium enolate of methyl ketone 36 is formed using a variety of reagents such as LDA, lithium bis(trimethylsilyl)amide or n-butyllithium at low temperature, while the corresponding potassium enolate is prepared using potassium bis(trimethylsilyl)amide. Addition of the lithium or potassium enolate of 36 to imine 18 following a procedure modified from Davis et. al. (Organic Letters, 2003, 5011-5014) furnishes adduct 37. Ketone 37 is reduced to alcohol 38, which is then hydrolyzed under acidic conditions to provide hydroxylamine 26.

SCHEME 5

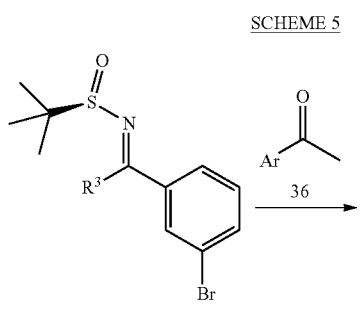

"HPLC" is an abbreviation used herein for high pressure liquid chromatography. "MS" refers to mass spectrometry data collected on a high pressure liquid chromatography system with a mass spectrometry detector, and are typically collected using electrospray ionization. "TLC" is an abbreviation used herein for thin layer chromatography. Proton NMR spectra were obtained on a Bruker 400 or 500 spectrometer. Data were referred to the lock solvent.

The examples provided are intended to assist in a further understanding of the present disclosure. Particular materials employed, species and conditions are intended to further illustrate the specific embodiments of the invention and not limit the reasonable scope thereof.

SYNTHESIS OF INTERMEDIATES

Preparation 1

1,5-dibromo-2,4-difluorobenzene

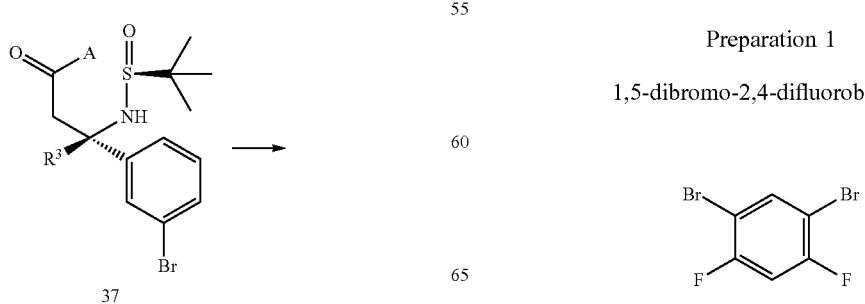

To a solution of 1-bromo-2,4-difluorobenzene (19.3 mL, 171 mmol) in CH$_2$Cl$_2$ (100 mL) was added iron (3.15 g, 56 mmol). To this stirred suspension was added a solution of bromine (11 mL, 214 mmol) in CH$_2$Cl$_2$ (25 mL) drop wise over 30 min. The resulting mixture was stirred at rt overnight. The reaction mixture was slowly poured into saturated aqueous Na$_2$S$_2$O$_3$ (200 mL), and the resulting mixture was stirred at rt for 30 min. This was extracted with CH$_2$Cl$_2$ (3×80 mL). The combined extracts were washed with brine, dried over MgSO$_4$, filtered and concentrated in vacuo to give 1,5-dibromo-2,4-difluorobenzene (40 g, 86% yield) as a brown oil. $^1$H NMR (500 MHz, CHLOROFORM-d) δ 7.79 (t, J=7.0 Hz, 1H), 7.00 (t, J=8.2 Hz, 1H).

Preparation 2

5-bromo-2,4-difluorobenzaldehyde

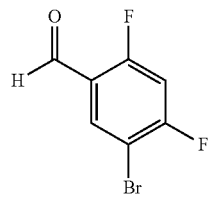

To a solution of 1,5-dibromo-2,4-difluorobenzene (17.5 g, 64.2 mmol) in ether (100 mL) at −78° C. was added n-BuLi (2.5 M solution, 30.8 mL, 77 mmol) over a period of 5 min, and the reaction mixture was stirred at −78° C. for 30 min. Then DMF (9.94 mL, 148 mmol) was added in one portion, and the mixture was stirred at −78° C. for 30 min. The reaction mixture was worked up with EtOAc/sat. NH$_4$Cl, and the crude product was purified by silica gel chromatography eluting with 0-10% EtOAc/Hexanes to give the title compound as a slightly yellow oil (8.5 g, 60% yield). $^1$H NMR (400 MHz, CHLOROFORM-d) δ 10.26 (s, 1H), 8.14 (t, J=7.5 Hz, 1H), 7.05 (dd, J=9.8, 8.0 Hz, 1H).

Preparation 3

2,4-difluoro-5-(pyrimidin-5-yl)benzaldehyde

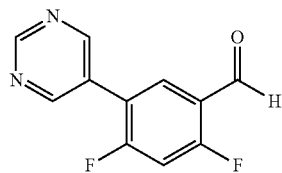 [SMILES: O=Cc1cc(-c2cncnc2)c(F)cc1F]

A mixture of bis(triphenylphosphine)palladium(II) chloride (0.56 g, 0.80 mmol), pyrimidin-5-ylboronic acid (0.99 g, 8.0 mmol), 5-bromo-2,4-difluorobenzaldehyde (0.88 g, 3.98 mmol), cesium carbonate (2.59 g, 7.96 mmol) in DME (13 mL), EtOH (7 mL) and water (7 mL) was heated at 100° C. for 45 min, and the crude reaction mixture was subjected to HPLC separation eluting with 0-100% A/B (A: 95% H$_2$O/5% MeCN, 10 MM NH$_4$OAc; B: 5% H$_2$O/95% MeCN, 10 mM NH$_4$OAC over 30 min period to give the title compound as a white solid (450 mg, 51% yield). $^1$H NMR (500 MHz, CHLOROFORM-d) δ 10.40-10.33 (m, 1H), 9.28 (s, 1H), 8.94 (d, J=1.2 Hz, 2H), 8.06 (dd, J=8.4, 7.8 Hz, 1H), 7.15 (t, J=9.9 Hz, 1H), 10.37 (s, 1H).

Preparation 4

4-fluoro-3-(pyrimidin-5-yl)benzaldehyde

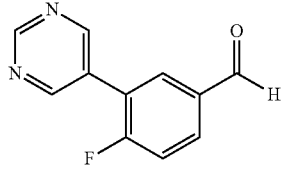 [SMILES: O=Cc1ccc(F)c(-c2cncnc2)c1]

The title compound was made from 3-bromo-4-fluorobenzaldehyde in the same fashion as described in Preparation 3. $^1$H NMR (500 MHz, CHLOROFORM-d) δ 10.07 (s, 1H), 9.29 (s, 1H), 9.00 (d, J=1.5 Hz, 2H), 8.08-7.95 (m, 2H), 7.44 (dd, J=9.8, 8.5 Hz, 1H).

Preparation 5

2-fluoro-5-(pyrimidin-5-yl)benzaldehyde

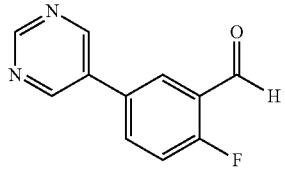 [SMILES: O=Cc1cc(-c2cncnc2)ccc1F]

The title compound was made from 3-bromo-4-fluorobenzaldehyde in the same fashion as described in Preparation 3. $^1$H NMR (500 MHz, CHLOROFORM-d) δ 10.35 (s, 1H), 9.27 (s, 1H), 8.93 (d, J=0.6 Hz, 2H), 8.05 (t, J=7.9 Hz, 1H), 7.63-7.50 (m, 1H), 7.15 (t, J=9.9 Hz, 1H).

Preparation 6

2-methoxy-5-vinylpyridine

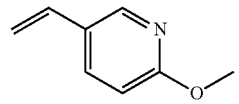

To a suspension of (methyl)triphenylphosphonium bromide (1234 mg, 3.46 mmol) in THF (11.200 mL) at rt was added N-butyllithium (2.5 M in hexanes) (1.508 mL, 3.77 mmol) drop wise over 5 min. The resulting mixture was stirred at rt for 1 h. A solution of 6-methoxynicotinaldehyde (431 mg, 3.14 mmol) in THF (1.400 mL) was then added drop wise over 5 min. The resulting reaction mixture was then stirred at rt for 1 h. The reaction was then diluted with EtOAc (30 mL), washed with water (3×15 mL), brine (15 mL), dried over MgSO$_4$, filtered and concentrated in vacuo. Purification by flash chromatography (silica, EtOAc/Hexanes) gave 2-methoxy-5-vinylpyridine (276 mg, 2.042 mmol, 65.0% yield) as a clear oil; MS (M+H)$^+$=136.1.

Preparation 7

1,5-dimethyl-4-vinyl-1H-pyrazole

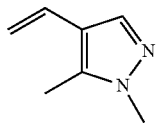

1,5-Dimethyl-1H-pyrazole-4-carbaldehyde (414 mg, 3.33 mmol) was treated under the same conditions reported for the aldehyde in Preparation 6 to give 1,5-dimethyl-4-vinyl-1H-pyrazole (311 mg, 2.55 mmol, 76% yield) as a clear, colorless oil; $^1$H NMR (500 MHz, CDCl$_3$) δ 7.57 (s, 1H), 6.55-6.42 (m, 1H), 5.42 (dd, J=17.7, 1.5 Hz, 1H), 5.06 (dd, J=11.1, 1.4 Hz, 1H), 3.78 (s, 3H), 2.27 (s, 3H).

Preparation 8

1,3-dimethyl-4-vinyl-1H-pyrazole

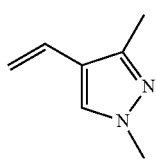

1,3-dimethyl-1H-pyrazole-4-carbaldehyde (700 mg, 5.64 mmol) was treated under the same conditions reported for the aldehyde in Preparation 6 to give 1,3-dimethyl-4-vinyl-1H-pyrazole (456 mg, 3.73 mmol, 66.2% yield) as a clear, colorless oil; $^1$H NMR (500 MHz, CDCl$_3$) δ 7.36 (s, 1H), 6.51 (dd, J=17.8, 11.2 Hz, 1H), 5.35 (dd, J=17.7, 1.4 Hz, 1H), 5.06 (dd, J=11.1, 1.4 Hz, 1H), 3.82 (s, 3H), 2.30 (s, 3H).

Preparation 9

1-methyl-4-vinyl-1H-pyrazole

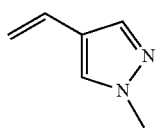

1-methyl-1H-pyrazole-4-carbaldehyde (651 mg, 5.91 mmol) was treated under the same conditions reported for the aldehyde in Preparation 6 to give 1-methyl-4-vinyl-1H-pyrazole (211 mg, 1.951 mmol, 33.0% yield) as a clear, colorless oil; $^1$H NMR (500 MHz, CDCl$_3$) δ 7.57 (s, 1H), 7.37 (s, 1H), 6.53 (dd, J=17.6, 10.9 Hz, 1H), 5.46 (dd, J=17.7, 1.4 Hz, 1H), 5.07 (dd, J=11.0, 1.4 Hz, 1H), 3.89 (s, 3H).

Preparation 10

1,3,5-trimethyl-4-vinyl-1H-pyrazole

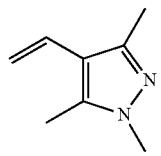

1,3,5-trimethyl-1H-pyrazole-4-carbaldehyde (664 mg, 4.81 mmol) was treated under the same conditions reported for the aldehyde in Preparation 6 to give 1,3,5-trimethyl-4-vinyl-1H-pyrazole (471 mg, 3.46 mmol, 72.0% yield) as a clear, colorless oil; $^1$H NMR (500 MHz, CDCl$_3$) δ 7.28 (s, 1H), 6.53 (dd, J=17.9, 11.6 Hz, 1H), 5.29 (dd, J=17.9, 1.6 Hz, 1H), 5.13 (dd, J=11.5, 1.6 Hz, 1H), 3.73 (s, 3H), 2.31 (s, 3H), 2.27 (s, 3H).

Preparation 11

4-(pyrimidin-5-yl)thiophene-2-carbaldehyde

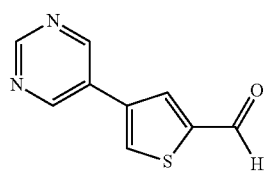 [SMILES: O=Cc1cc(-c2cncnc2)cs1]

To a solution of 4-bromothiophene-2-carbaldehyde (500 mg, 2.62 mmol) and Pyrimidin-5-ylboronic acid hemihydrate (1391 mg, 10.47 mmol) in DME (11.900 mL), EtOH (5.95 mL), and water (5.95 mL) was added bis(triphenylphosphine)palladium(II) chloride (367 mg, 0.523 mmol) and cesium carbonate (3411 mg, 10.47 mmol). The resulting mixture was brought to 100° C. and stirred for 1 h. The reaction mixture was then diluted with EtOAc (50 mL), washed with water (2×25 mL), brine (25 mL), dried over MgSO$_4$, filtered and concentrated in vacuo. Purification by flash chromatography (Silica, EtOAc/Hexanes) gave 4-(pyrimidin-5-yl)thiophene-2-carbaldehyde (329 mg, 1.730 mmol, 66.1% yield) as an off-white solid; MS (M+H)$^+$ =191.2.

Preparation 12

3'-formylbiphenyl-3-carbonitrile

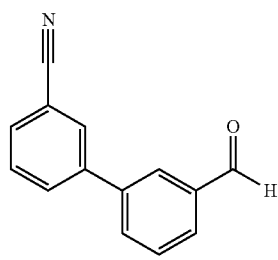 [SMILES: N#Cc1cccc(-c2cccc(C=O)c2)c1]

3-Bromobenzaldehyde and (3-cyanophenyl)boronic acid were reacted in the same manner as the corresponding reagents in Preparation 11 to give 3'-formyl-[1,1'-biphenyl]-3-carbonitrile which was used without purification.

Preparation 13

3-bromo-5-(prop-1-ynyl)pyridine

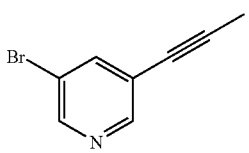

A solution of trimethyl(prop-1-yn-1-yl)silane (1.7 g, 11.48 mmol), 3,5-dibromopyridine (2.72 g, 11.48 mmol), Pd(PPh3)$_4$ (0.66 g, 0.57 mmol), TBAF (1.0 M solution in THF, 11.48 mL, 11.48 mmol), copper(I) iodide (0.66 g, 3.44 mmol), and triethylamine (5.28 mL, 37.9 mmol) was stirred at rt for 12 h. The reaction mixture was worked up with EtOAc and water, and the crude product was purified by silica gel chromatography eluting with 0-3% EtOAc/Hexanes to give the title compound as a white solid (0.96 g, 42% yield). $^1$H NMR (400 MHz, CHLOROFORM-d) δ 8.55 (dd, J=12.3, 2.0 Hz, 2H), 7.83 (t, J=1.9 Hz, 1H), 2.10 (s, 3H).

Preparation 14

(5-(prop-1-yn-1-yl)pyridin-3-yl)boronic acid

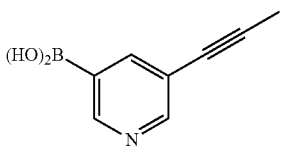

To a solution of 3-bromo-5-(prop-1-ynyl)pyridine (2.96 g, 15.10 mmol) and triisopropyl borate (4.21 ml, 18.12 mmol) in THF and toluene at −40° C. was added n-BuLi (2.5 M solution in hexanes, 7.25 mL, 18.12 mmol) drop wise over a period of 7 min, and the reaction mixture was stirred at −40° C. for 30 min and then warmed up to −20° C. over a period of 8 min. The reaction was quenched with HCl (15.10 ml, 2 M solution, 30.2 mmol), and a reddish solution was formed. The two layers were separated, and the organic layer was extracted with water (3×10 mL). To the combined organic layers were added NaOH (5M solution, 2.416 ml, 12.08 mmol) (to adjust pH to 7). During the addition, a very white cloudy solution was formed. THF (30 mL) was added, but the layers did not separate. Solid sodium chloride was added to make the solution saturated, and the two layers were formed. The layers were separated, and the aqueous layer was extracted with THF (3×20 mL), and the combined THF layers were dried over sodium sulfate and then filtered. The filtrate was evaporated in vacuo, and the residue was concentrated to give a white powder (553 mg). This material was used without further purification.

Preparation 15

2,4-difluoro-5-(5-(prop-1-yn-1-yl)pyridin-3-yl)benzaldehyde

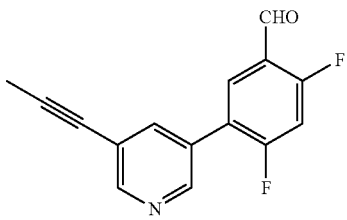 [SMILES: CC#Cc1cncc(-c2cc(C=O)c(F)cc2F)c1]

The title compound was made from 5-bromo-2,4-difluorobenzaldehyde and 5-(prop-1-yn-1-yl)pyridin-3-yl)boronic acid in the same fashion as described in Preparation 3. $^1$H NMR (400 MHz, CHLOROFORM-d) δ 10.36 (s, 1H), 8.80 (br. s., 2H), 8.02 (t, J=8.0 Hz, 1H), 7.10 (t, J=9.9 Hz, 1H), 2.12 (s, 3H).

Preparation 16

5-methyl-4-(prop-1-en-2-yl)isoxazole

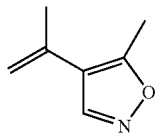

1-(5-methylisoxazol-4-yl)ethanone (1 g, 7.99 mmol) was treated under the same conditions reported for the aldehyde in Preparation 6 to give 5-methyl-4-(prop-1-en-2-yl)isoxazole (151 mg, 1.226 mmol, 15.34% yield) as a clear, colorless oil; $^1$H NMR (500 MHz, CDCl$_3$) δ 8.19 (s, 1H), 5.17-4.99 (m, 2H), 2.52 (s, 3H), 2.13-1.97 (m, 3H).

Preparation 17

3,5-dimethyl-4-(prop-1-en-2-yl)isoxazole

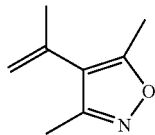

To a solution of ethyl 3,5-dimethylisoxazole-4-carboxylate (5 g, 29.6 mmol) in THF (148 ml) at −78° C. was added methyllithium (1.6 M in ether) (55.4 ml, 89 mmol) drop wise over 15 min. When the addition was complete, the reaction mixture was allowed to stir at −78° C. for 30 min. Water (100 mL) was then added very slowly. The mixture was then allowed to come to rt. This mixture was then extracted with EtOAc (3×30 mL). The combined extracts were washed with brine (30 mL), dried over MgSO$_4$, filtered and concentrated in vacuo. The resulting oil was taken up in dichloromethane (148 ml). This mixture was cooled to 0° C.

and triethylamine (16.48 ml, 118 mmol) was added. Methanesulfonic anhydride (7.72 g, 44.3 mmol) was then added and the resulting mixture was stirred at 0° C. for 30 min. The reaction mixture was then washed with water (2×40 mL) dried over MgSO₄, filtered and concentrated in vacuo. Purification by flash chromatography (Silica, EtOAc/Hexanes) gave 3,5-dimethyl-4-(prop-1-en-2-yl)isoxazole (1.2 g, 8.75 mmol, 29.6% yield) as a clear, colorless oil; $^1$H NMR (500 MHz, CDCl₃) δ 5.23 (quin, J=1.6 Hz, 1H), 4.92 (dd, J=1.8, 0.9 Hz, 1H), 2.38 (s, 3H), 2.26 (s, 3H), 2.00 (dd, J=1.5, 0.9 Hz, 3H).

Preparation 18

3-(5-formylthiophen-3-yl)benzonitrile

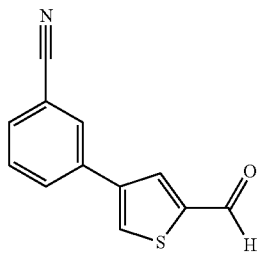 [SMILES: N#Cc1cccc(-c2csc(C=O)c2)c1]

4-bromothiophene-2-carbaldehyde (1 g, 5.23 mmol) and (3-cyanophenyl)boronic acid (1.923 g, 13.09 mmol) were treated in essentially the same manner as the corresponding reagents in Preparation 11 to give 3-(5-formylthiophen-3-yl)benzonitrile (0.670 g, 3.14 mmol, 60% yield) as a yellow solid; $^1$H NMR (500 MHz, MeOD-d₄) δ 9.99 (d, J=1.4 Hz, 1H), 8.41-8.32 (m, 2H), 8.18-8.04 (m, 2H), 7.72 (dt, J=7.9, 1.3 Hz, 1H), 7.68-7.60 (m, 1H).

Preparation 19

4-(5-(prop-1-ynyl)pyridin-3-yl)thiophene-2-carbaldehyde

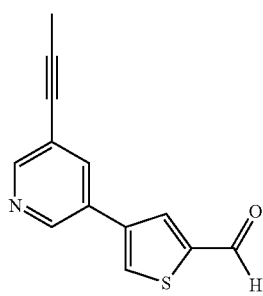 [SMILES: CC#Cc1cncc(-c2csc(C=O)c2)c1]

4-Bromothiophene-2-carbaldehyde (166 mg, 0.870 mmol) and (5-(prop-1-yn-1-yl)pyridin-3-yl)boronic acid (Preparation 14, 140 mg, 0.870 mmol) were treated in essentially the same manner as the corresponding reagents in Preparation 11 to give 4-(5-(prop-1-yn-1-yl)pyridin-3-yl)thiophene-2-carbaldehyde (86 mg, 0.378 mmol, 43.5% yield) as a yellow oil; $^1$H NMR (500 MHz, Methanol-d₄) δ 9.99 (d, J=1.2 Hz, 1H), 8.84 (s, 1H), 8.50 (s, 1H), 8.40-8.34 (m, 2H), 8.17 (s, 1H), 2.12 (s, 3H).

Preparation 20

(5-amino-2-fluorophenyl)methanol

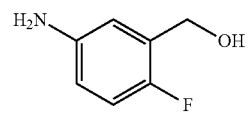

To a solution of 2-fluoro-5-nitrobenzaldehyde (5 g, 29.6 mmol) in MeOH (118 ml) was added NaBH₄ (1.119 g, 29.6 mmol) portion wise with stirring (gas evolution). The addition took approx. 20 min. When the addition was complete, the reaction mixture was stirred at rt for 30 min. The mixture was quenched by the slow addition of water (100 mL). The mixture was then concentrated to remove MeOH. The remaining aqueous mixture was extracted with EtOAc (3×25 mL). The combined extracts were washed with brine, dried over MgSO₄, filtered and concentrated in vacuo. The resulting residue was taken up in MeOH (118 ml). Pd/C (0.157 g, 1.478 mmol) was added and the resulting mixture was stirred vigorously under an atmosphere of hydrogen for 2 h. The reaction mixture was then filtered through Celite and concentrated in vacuo to give (5-amino-2-fluorophenyl)methanol (80% yield) which was used without further purification; MS (M+H)⁺=142.1.

Preparation 21

5-bromo-N-(4-fluoro-3-(hydroxymethyl)phenyl)picolinamide

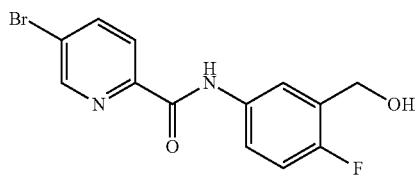 [SMILES: O=C(Nc1ccc(F)c(CO)c1)c1ccc(Cl)cn1]

To a solution of (5-amino-2-fluorophenyl)methanol (Preparation 20, 1.043 g, 7.39 mmol) in DMF (37.0 ml) was added 5-bromopyridine-2-carboxylic acid (1.493 g, 7.39 mmol) and HATU (2.81 g, 7.39 mmol). DIEA (1.291 ml, 7.39 mmol) was then added to the mixture which was stirred at rt for 1 h. The mixture was then diluted with EtOAc (50 mL), washed with water (3×25 mL), brine (25 mL), dried over MgSO₄, filtered and concentrated in vacuo. Chloroform was added to the resulting oil at which time a precipitate formed. The precipitate was isolated by filtration to give 5-bromo-N-(4-fluoro-3-(hydroxymethyl)phenyl)picolinamide (1.69 g, 5.20 mmol, 70.3% yield) as an off-white crystalline solid; LC-MS (M+H)⁺=325.1; $^1$H NMR (500 MHz, DMSO-d₆) δ 10.70 (s, 1H), 8.86 (dd, J=2.3, 0.6 Hz, 1H), 8.33 (dd, J=8.4, 2.3 Hz, 1H), 8.08 (dd, J=8.3, 0.5 Hz, 1H), 8.06 (dd, J=6.8, 2.7 Hz, 1H), 7.75 (ddd, J=8.7, 4.7, 2.7 Hz, 1H), 7.18-7.10 (m, 1H), 5.30 (t, J=5.6 Hz, 1H), 4.55 (d, J=5.6 Hz, 2H).

Preparation 22

5-chloro-N-(4-fluoro-3-(hydroxymethyl)phenyl)picolinamide

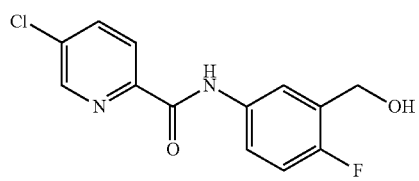

5-Chloropicolinic acid (1.35 g, 8.57 mmol) was treated essentially the same as the corresponding acid in Preparation 21 except that the crude product was purified by flash chromatography (silica, EtOAc/Hexanes) to give 5-chloro-N-(4-fluoro-3-(hydroxymethyl)phenyl)picolinamide (1.69 g, 6.02 mmol, 70.3% yield) as an off-white solid; LC-MS (M+H)$^+$=281.1; $^1$H NMR (500 MHz, DMSO-d$_6$) δ 10.71 (s, 1H), 8.78 (dd, J=2.4, 0.7 Hz, 1H), 8.76 (dd, J=4.4, 1.4 Hz, 1H), 8.53 (dd, J=8.4, 1.4 Hz, 1H), 8.24-8.11 (m, 2H), 8.06 (dd, J=6.8, 2.7 Hz, 1H), 7.75 (ddd, J=8.8, 4.7, 2.8 Hz, 1H), 7.21-7.08 (m, 1H), 5.31 (t, J=5.6 Hz, 1H), 4.55 (d, J=4.9 Hz, 2H).

Preparation 23

5-bromo-N-(4-fluoro-3-formylphenyl)picolinamide

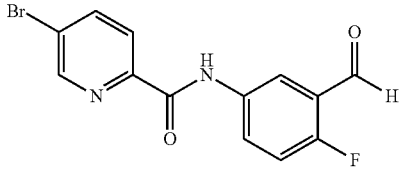

To a solution of oxalyl chloride (0.538 ml, 6.15 mmol) in DCM (30.8 ml) at −78° C. was added DMSO (0.873 ml, 12.30 mmol) drop wise (caution: gas evolution). When the addition was complete, the resulting mixture was allowed to stir at −78° C. for 10 min. The 5-bromo-N-(4-fluoro-3-(hydroxymethyl)phenyl)picolinamide (Preparation 21, 1 g, 3.08 mmol) was then added portion wise over 5 min. When this addition was complete, the reaction mixture was stirred at −78° C. for 10 min. DIEA (4.30 ml, 24.61 mmol) was then added to the reaction mixture at which time the cooling bath was removed and the reaction mixture was allowed to come to rt. After stirring at rt for 1 h., the reaction mixture was washed with saturated aqueous sodium bicarbonate (2×15 mL), brine (15 mL), dried over MgSO$_4$, filtered and concentrated in vacuo. Purification by flash chromatography (Silica, EtOAc/Hexanes) gave 5-bromo-N-(4-fluoro-3-formylphenyl)picolinamide (433 mg, 1.340 mmol, 43.6% yield) as a white solid; LC-MS (M+H)$^+$=323.1; $^1$H NMR (500 MHz, DMSO-d$_6$) δ 11.03 (s, 1H), 10.24 (s, 1H), 8.88 (dd, J=2.2, 0.7 Hz, 1H), 8.48 (dd, J=6.3, 2.7 Hz, 1H), 8.34 (dd, J=8.4, 2.4 Hz, 1H), 8.18 (ddd, J=9.0, 4.7, 2.9 Hz, 1H), 8.10 (dd, J=8.4, 0.6 Hz, 1H), 7.44 (dd, J=10.1, 9.1 Hz, 1H).

Preparation 24

5-chloro-N-(4-fluoro-3-formylphenyl)picolinamide

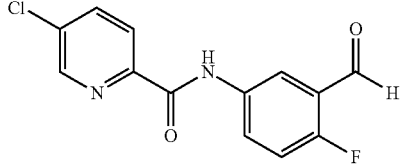 [SMILES: O=Cc1cc(NC(=O)c2ccc(Cl)cn2)ccc1F]

To a suspension of 5-chloro-N-(4-fluoro-3-(hydroxymethyl)phenyl) picolinamide (Preparation 22, 1.6 g, 5.70 mmol) in DCM (28.500 mL) was added a mixture of PCC (4.92 g, 22.80 mmol) and finely ground 4 A molecular sieves (4.92 g, 5.70 mmol). The resulting mixture was stirred at rt for 1 h. The mixture was then applied directly to a silica gel column. Purification by flash chromatography (Silica, MeOH/CHCl$_3$) gave 5-chloro-N-(4-fluoro-3-formylphenyl) picolinamide (1.4 g, 5.02 mmol, 88% yield) as a white solid; LC-MS (M+H)$^+$=323.1; $^1$H NMR (500 MHz, DMSO-d$_6$) δ 11.01 (s, 1H), 10.24 (s, 1H), 8.79 (dd, J=2.3, 0.6 Hz, 1H), 8.48 (dd, J=6.3, 2.9 Hz, 1H), 8.24-8.13 (m, 3H), 7.44 (dd, J=10.1, 9.2 Hz, 1H).

Preparation 25

1-(5-bromo-2,4-difluorophenyl)ethanone

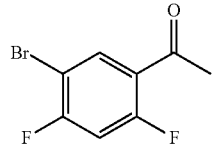

The title compound was made from 1,5-dibromo-2,4-difluorobenzene in the same fashion as described in Preparation 1 except that N-methoxy-N-methylacetamide was used instead of DMF. $^1$H NMR (500 MHz, CHLOROFORM-d) δ 8.17 (t, J=7.8 Hz, 1H), 6.99 (dd, J=10.3, 8.0 Hz, 1H), 2.65 (d, J=5.2 Hz, 3H).

Preparation 26

(R,E)-N-(1-(5-bromo-2,4-difluorophenyl)ethylidene)-2-methylpropane-2-sulfinamide

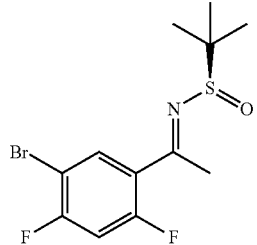 [SMILES: C/C(=N\[S@](=O)C(C)(C)C)c1cc(Br)c(F)cc1F]

To a solution of 1-(5-bromo-2,4-difluorophenyl)ethanone (7.4 g, 31.5 mmol) and (R)-2-methylpropane-2-sulfinamide (4.86 g, 40.9 mmol) in THF (79 mL) was added ethyl orthotitanate (15.8 g, 69.3 mmol), and the reaction mixture was heated at 65° C. for 48 h. Water was added, and the resulting suspension was filtered through a pad of Celite. The filtrate was worked up with EtOAc, and the crude product was purified by silica gel chromatography eluting with 10-40% EtOAc/Hexanes to give the title compound as a yellow oil (7.3 g, 68% yield). $^1$H NMR (500 MHz, CHLOROFORM-d) δ 7.94 (t, J=7.7 Hz, 1H), 6.97 (dd, J=10.5, 8.1 Hz, 1H), 2.76 (d, J=3.7 Hz, 3H), 1.33 (s, 9H).

Preparation 27

(S)-methyl 3-(5-bromo-2,4-difluorophenyl)-3-((R)-1,1-imethylethylsulfinamido)butanoate

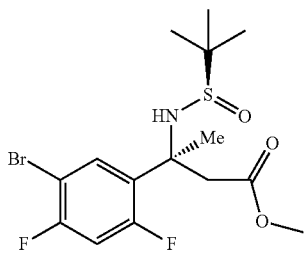 [SMILES: COC(=O)C[C@](C)(N[S@](=O)C(C)(C)C)c1cc(Br)c(F)cc1F]

To a solution of diisopropylamine (7.69 ml, 54.0 mmol) in THF (10 mL) at 0° C. was added n-BuLi (21.58 ml, 2.50 M solution in hexanes, 54.0 mmol) and the reaction mixture was stirred at 0° C. for 15 min and then cooled to −78° C. Methyl acetate (4.30 ml, 54.0 mmol) was added drop wise, and the reaction mixture was stirred at −78° C. for 30 min. Chlorotitanium triisopropoxide (14.18 ml, 59.4 mmol) in THF (5 mL) was added drop wise, and the solution was stirred at −78° C. for 1 h. A solution of (R,E)-N-(1-(5-bromo-2,4-difluorophenyl)ethylidene)-2-methylpropane-2-sulfinamide (7.3 g, 21.58 mmol) in THF (5 mL) was added, and the reaction mixture was stirred at −78° C. for 3 h. Saturated NH$_4$Cl was added, and a sticky suspension was formed. This suspension was filtered through a pad of Celite and washed with EtOAc. The filtrate was worked up with EtOAc, and the crude product was purified by silica gel chromatography eluting with 10-30% EtOAc/Hexanes to give the title compound as a slightly yellow oil (6.5 g, 15.77 mmol, 73.0% yield). $^1$H NMR (500 MHz, CHLOROFORM-d) δ 7.72 (t, J=8.1 Hz, 1H), 6.87 (dd, J=11.8, 8.0 Hz, 1H), 3.62 (s, 3H), 3.34 (dd, J=16.8, 1.1 Hz, 1H), 3.12 (dd, J=16.8, 1.5 Hz, 1H), 1.82 (s, 3H), 1.32 (s, 9H).

Preparation 28

(R)—N—((S)-2-(5-bromo-2,4-difluorophenyl)-4-hydroxybutan-2-yl)-2-methylpropane-2-sulfinamide

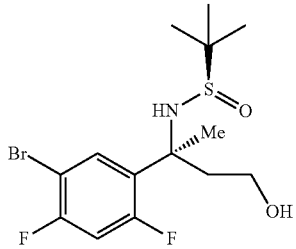 [SMILES: CC(C)(C)[S@@](=O)N[C@@](C)(CCO)c1cc(Br)c(F)cc1F]

To a solution of (S)-methyl 3-(5-bromo-2,4-difluorophenyl)-3-((R)-1,1-dimethylethylsulfinamido)butanoate (1.9 g, 4.61 mmol) in THF (15 mL) at 0° C. was added LiAlH$_4$ solution in ether (1.0 M solution, 5.0 mL, 5.0 mmol) drop wise, and the reaction mixture was stirred at 0° C. for 1 h. A minimum amount of saturated sodium sulfate solution was added to quench the excessive LiAlH$_4$, and 100 mL of ether was added followed by anhydrous sodium sulfate. This mixture was stirred at rt for 2 h and then filtered. The filtrate was evaporated in vacuo to give the title compound as a colorless oil (1.7 g, 98%). $^1$H NMR (500 MHz, CHLOROFORM-d) δ 7.73 (t, J=8.1 Hz, 1H), 6.90 (dd, J=11.7, 7.9 Hz, 1H), 4.04-3.92 (m, 1H), 3.61-3.52 (m, 1H), 2.48-2.27 (m, 2H), 1.82 (s, 3H), 1.33-1.31 (m, 9H).

Preparation 29

(S)-3-amino-3-(5-bromo-2,4-difluorophenyl)butan-1-ol

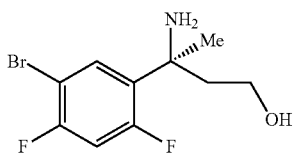 [SMILES: C[C@](N)(CCO)c1cc(Br)c(F)cc1F]

To a solution of (R)—N—((S)-2-(5-bromo-2,4-difluorophenyl)-4-hydroxybutan-2-yl)-2-methylpropane-2-sulfinamide (1.73 g, 4.5 mmol) in MeOH (15 mL) at rt was added 4 M HCl in dioxane (12.38 mL, 49.5 mmol), and the reaction mixture was stirred at rt for 12 h. The solvent was removed, and the residue was worked up with saturated sodium bicarbonate and EtOAc. The crude product was used directly without further purification. $^1$H NMR (500 MHz, CHLOROFORM-d) δ 7.72 (t, J=8.0 Hz, 1H), 6.92 (dd, J=11.7, 8.0 Hz, 1H), 3.92-3.81 (m, 1H), 3.56 (ddd, J=11.5, 8.0, 3.7 Hz, 1H), 2.28-2.18 (m, 1H), 2.03-1.96 (m, 1H), 1.67 (s, 3H).

Preparation 30

(S)-tert-butyl (2-(5-bromo-2,4-difluorophenyl)-4-hydroxybutan-2-yl)carbamate

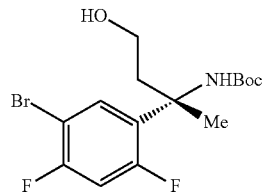 [SMILES: CC(C)(C)OC(=O)N[C@@](C)(CCO)c1cc(Br)c(F)cc1F]

A mixture of (S)-3-amino-3-(5-bromo-2,4-difluorophenyl)butan-1-ol (1.43 g, 5.11 mmol) and BOC$_2$O (2.371 ml, 10.21 mmol) in dioxane (11.87 ml), and H$_2$O (1.781 ml) was stirred at rt for 12 h, and then worked up with EtOAc/water, and the crude product was purified by silica gel chromatography eluting with 10-30% EtOAc/Hexanes to give the title compound as a colorless oil (1.2 g, 3.16 mmol, 61.8% yield). $^1$H NMR (500 MHz, CHLOROFORM-d) δ 7.53 (t, J=8.2 Hz, 1H), 6.87 (dd, J=11.6, 8.1 Hz, 1H), 3.83 (ddd, J=10.8, 6.4, 4.3 Hz, 1H), 3.66-3.50 (m, 1H), 2.29-2.16 (m, 1H), 2.12-2.01 (m, 2H), 1.84 (s, 3H), 1.44 (br. s., 9H).

Preparation 31

(S)-tert-butyl (2-(5-bromo-2,4-difluorophenyl)-4-oxobutan-2-yl)carbamate

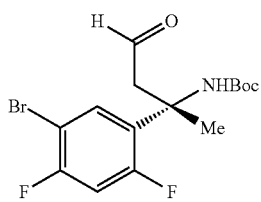 [SMILES: CC(C)(C)OC(=O)N[C@@](C)(CC=O)c1cc(Br)c(F)cc1F]

To a solution of oxalyl chloride (0.530 ml, 6.05 mmol) in CH$_2$Cl$_2$ (8 mL) at −78° C. was added DMSO (0.859 ml, 12.10 mmol), and the reaction mixture was stirred at −78° C. for 20 min. A solution of (S)-tert-butyl (2-(5-bromo-2,4-difluorophenyl)-4-hydroxybutan-2-yl)carbamate (1.15 g, 3.02 mmol) in CH$_2$Cl$_2$ (7 mL) was added drop wise, and the reaction mixture was stirred at −78° C. for 30 min. Triethylamine (2.53 ml, 18.15 mmol) was added and the reaction mixture was warmed up to rt over a 30 min period. The reaction was worked up with EtOAc/water, and the crude product was purified by silica gel chromatography eluting with 10-30% EtOAc/Hexanes to give the title compound (1.1 g, 96%). $^1$H NMR (500 MHz, CHLOROFORM-d) δ 9.74 (s, 1H), 7.51 (t, J=8.0 Hz, 1H), 6.91 (dd, J=11.7, 8.1 Hz, 1H), 3.50 (br. s., 1H), 3.00 (dt, J=14.9, 1.4 Hz, 1H), 1.78-1.67 (m, 3H).

Preparation 32 tert-butyl ((2S,4R)-2-(5-bromo-2,4-difluorophenyl)-4-(3,5-dimethylisoxazol-4-yl)-4-hydroxybutan-2-yl)carbamate

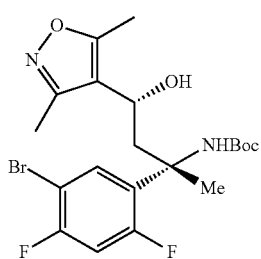 [SMILES: Cc1noc(C)c1[C@H](O)C[C@](C)(NC(=O)OC(C)(C)C)c1cc(Br)c(F)cc1F]

To a solution of 4-bromo-3,5-dimethylisoxazole (248 mg, 1.41 mmol) in ether (1.8 mL) at −78° C. was added n-BuLi (2.50 M solution in hexanes, 0.56 mL, 1.41 mmol), and the reaction mixture was stirred at −78° C. for 1 h. A solution of (S)-tert-butyl (2-(5-bromo-2,4-difluorophenyl)-4-oxobutan-2-yl)carbamate (232 mg, 0.61 mmol) in THF (0.30 mL) was added, and the reaction mixture was stirred at −78° C. for 1 h. The reaction was partitioned between saturated NH$_4$Cl and EtOAc, and the organic layer was isolated and concentrated. The crude product was purified by preparative TLC eluting with 40% EtOAc/Hexanes to give tert-butyl ((2S,4R)-2-(5-bromo-2,4-difluorophenyl)-4-(3,5-dimethylisoxazol-4-yl)-4-hydroxybutan-2-yl)carbamate as a minor isomer (87 mg, 30% yield). $^1$H NMR (500 MHz, CHLOROFORM-d) δ 7.56 (t, J=8.1 Hz, 1H), 6.86 (dd, J=11.7, 8.1 Hz, 1H), 6.29 (br. s., 1H), 4.99 (dd, J=10.0, 1.8 Hz, 1H), 2.56-2.47 (m, 1H), 2.40 (s, 3H), 2.30 (s, 3H), 1.95-1.88 (s, 3H), 1.40 (br. s., 9H). Isomer B (major isomer): $^1$H NMR (500 MHz, CHLOROFORM-d) δ 7.54 (t, J=7.6 Hz, 1H), 6.91 (dd, J=11.5, 8.0 Hz, 1H), 6.61 (br. s., 1H), 4.37 (d, J=10.4 Hz, 1H), 2.36 (dd, J=15.0, 10.5 Hz, 1H), 2.23 (s, 3H), 2.15 (s, 3H), 1.88 (s, 3H), 1.49 (br. s., 9H).

Preparation 33

(1R,3S)-3-amino-3-(5-bromo-2,4-difluorophenyl)-1-(3,5-dimethylisoxazol-4-yl)butan-1-ol

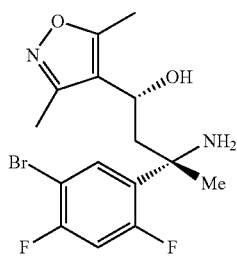 [SMILES: Cc1noc(C)c1[C@H](O)C[C@](C)(N)c1cc(Br)c(F)cc1F]

Method A:

To a solution of isomer A of tert-butyl ((2S,4R)-2-(5-bromo-2,4-difluorophenyl)-4-(3,5-dimethylisoxazol-4-yl)-4-hydroxybutan-2-yl)carbamate (52 mg, 0.11 mmol) (from Preparation 33) in CH$_2$Cl$_2$ (0.31 mL) at rt was added TFA (59 μL), and the reaction mixture was stirred at rt for 1 h. The crude product was purified directly by preparative TLC eluting with 90% CH$_2$Cl$_2$/9% MeOH/1% NH$_3$.H$_2$O to give (1R,3S)-3-amino-3-(5-bromo-2,4-difluorophenyl)-1-(3,5-dimethylisoxazol-4-yl)butan-1-ol as a white solid (20 mg, 48% yield). $^1$H NMR (500 MHz, CHLOROFORM-d) δ 7.52 (dd, J=8.5, 7.6 Hz, 1H), 6.93 (dd, J=11.9, 7.9 Hz, 1H), 5.09 (dd, J=11.1, 2.1 Hz, 1H), 2.42 (s, 3H), 2.32 (s, 3H), 2.19 (dd, J=14.3, 11.3 Hz, 1H), 1.83 (dd, J=14.3, 2.3 Hz, 1H), 1.74 (s, 3H).

Method B:

To a solution of (R)—N-((2S,4R)-2-(5-bromo-2,4-difluorophenyl)-4-(3,5-dimethylisoxazol-4-yl)-4-hydroxybutan-2-yl)-2-methylpropane-2-sulfinamide (4.2 g, 8.76 mmol) (from Preparation 37) in methanol (35.0 ml) at rt was added 4 N HCl in dioxane (21.90 ml, 88 mmol), and the reaction mixture was stirred at rt for 10 min. The solvents were removed completely and the residue was then dried in vacuo to give a yellow foam. Saturated sodium bicarbonate was added and the aqueous layer was extracted with DCM (×3). The combined organic layers were washed with brine, dried over anhydrous sodium sulfate, and filtered, and the filtrate was evaporated in vacuo to give the crude product. The crude product was purified by silica gel chromatography eluting with 95% DCM/5% MeOH/0.5% ammonium hydroxide to give (1R,3S)-3-amino-3-(5-bromo-2,4-difluorophenyl)-1-(3,5-dimethylisoxazol-4-yl)butan-1-ol (2.9 g, 7.73 mmol, 88% yield) as a colorless oil. This material was used without further purification.

Preparation 34

N-methoxy-N,3,5-trimethylisoxazole-4-carboxamide

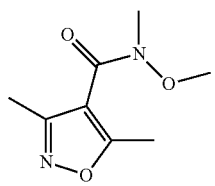

N-methoxy-N,3,5-trimethylisoxazole-4-carboxamide

A solution of 3,5-dimethylisoxazole-4-carboxylic acid (15 g, 106 mmol), N,O-dimethylhydroxylamine hydrochloride (11.40 g, 117 mmol), HATU (44.5 g, 117 mmol) and Hunig's Base (46.4 ml, 266 mmol) in DCM (304 ml) was stirred at rt for 2 days. Water was added and the aqueous layer was extracted with DCM (×3). The combined organic layers were washed with brine, dried over anhydrous sodium sulfate, and filtered, and the filtrate was evaporated in vacuo to give the crude product. The crude product was purified by silica gel chromatography eluting with 0-40% EtOAc/Hexane to give N-methoxy-N,3,5-trimethylisoxazole-4-carboxamide (19 g) as a colorless oil. $^1$H NMR (500 MHz, CHLOROFORM-d) δ 3.53 (s, 3H), 3.36 (s, 3H), 2.48 (s, 3H), 2.34 (s, 3H).

Preparation 35

1-(3,5-dimethylisoxazol-4-yl)ethanone

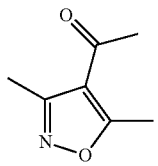

To a solution of N-methoxy-N,3,5-trimethylisoxazole-4-carboxamide (20 g, 109 mmol) in THF (362 ml) at 0° C. was added MeMgBr (155 ml, 217 mmol) dropwise via a dropping funnel, and the reaction mixture was stirred at 0° C. for 3 h and then at rt for 10 h. A lot of white precipitate appeared by the end of the addition of MeMgBr. 1 N aqueous HCl (109 ml, 109 mmol) was added dropwise, ethyl acetate was added, and the organic layer was separated. The aqueous layer was extracted with EtOAc (×3). The combined organic layers were washed with brine, dried over anhydrous sodium sulfate, and filtered, and the filtrate was evaporated in vacuo to give the crude product. The crude product was purified by silica gel chromatography eluting with 0-40% EtOAc/Hexane to give 1-(3,5-dimethylisoxazol-4-yl)ethanone (13 g, 93 mmol, 86% yield) as a colorless oil, which solidified upon standing at rt. $^1$H NMR (500 MHz, CHLOROFORM-d) δ 2.697 (s, 3H), 2.481 (s, 3H), and 2.478 (s, 3H).

Preparation 36

(R)—N—((S)-2-(5-bromo-2,4-difluorophenyl)-4-(3,5-dimethylisoxazol-4-yl)-4-oxobutan-2-yl)-2-methylpropane-2-sulfinamide

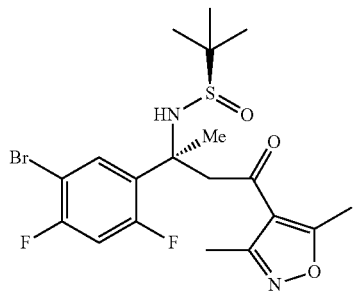 [SMILES: Cc1noc(C)c1C(=O)C[C@](C)(N[S@](=O)C(C)(C)C)c1cc(Br)c(F)cc1F]

To a solution of 1-(3,5-dimethylisoxazol-4-yl)ethanone (3.70 g, 26.6 mmol) in THF (36 mL) at −78° C. was added n-BuLi (10.64 ml, 26.6 mmol), and the reaction mixture was stirred −78° C. for 20 min. Then a solution of (R,E)-N-(1-(5-bromo-2,4-difluorophenyl)ethylidene)-2-methylpropane-2-sulfinamide (5 g, 14.78 mmol) in THF (15 mL) was added dropwise, and the reaction mixture was stirred at −78° C. for 30 min, warmed up to −40° C. over a 30 min period, and then stirred at −40° C. for 30 min. Water was added and the aqueous layer was extracted with EtOAc (×3). The combined organic layers were washed with brine, dried over anhydrous sodium sulfate, and filtered, and the filtrate was evaporated in vacuo to give the crude product. The crude product was purified by silica gel chromatography eluting with 1-40% EtOAc/Hexanes followed by 40% EtOAc/Hexanes to give (R)—N—((S)-2-(5-bromo-2,4-difluorophenyl)-4-(3,5-dimethylisoxazol-4-yl)-4-oxobutan-2-yl)-2-methylpropane-2-sulfinamide (3.9 g, 8.17 mmol, 55.3% yield) as a foam. $^1$H NMR (500 MHz, CHLOROFORM-d) δ 7.81 (t, J=8.2 Hz, 1H), 6.82 (dd, J=12.2, 7.9 Hz, 1H), 5.48 (s, 1H), 3.95-3.84 (m, 1H), 3.64 (dd, J=18.3, 2.9 Hz, 1H), 2.65 (s, 3H), 2.41 (s, 3H), 1.80 (s, 3H), 1.34 (s, 9H).

Preparation 37

(R)—N-((2S,4R)-2-(5-bromo-2,4-difluorophenyl)-4-(3,5-dimethylisoxazol-4-yl)-4-hydroxybutan-2-yl)-2-methylpropane-2-sulfinamide

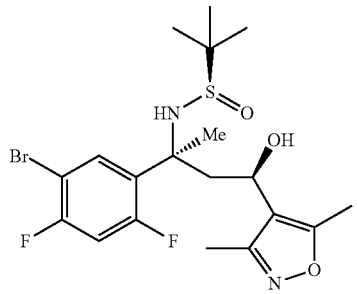 [SMILES: Cc1noc(C)c1[C@H](O)C[C@](C)(N[S@](=O)C(C)(C)C)c1cc(Br)c(F)cc1F]

To a solution of (R)—N—((S)-2-(5-bromo-2,4-difluorophenyl)-4-(3,5-dimethylisoxazol-4-yl)-4-oxobutan-2-yl)-2-methylpropane-2-sulfinamide (3.3 g, 6.91 mmol) in ether (46.1 ml) at −78° C. was added lithium tri-tert-butoxyaluminum hydride (1 M solution in toluene, 27.7 ml, 27.7 mmol) dropwise, and the reaction mixture was stirred at −78° C. for 10 min and then warmed up to −20° C. over a period of 1 h. The reaction mixture was diluted with 100 mL of ether, crystals of sodium sulfate decahydrate were added, and the reaction mixture was stirred at rt for 12 h and then filtered. The filtrate was evaporated in vacuo to give (R)—N-((2S,4R)-2-(5-bromo-2,4-difluorophenyl)-4-(3,5-dimethylisoxazol-4-yl)-4-hydroxybutan-2-yl)-2-methylpropane-2-sulfinamide (2.9 g, 6.05 mmol, 88% yield) as a white foam. $^1$H NMR (500 MHz, CHLOROFORM-d) δ 7.68 (t, J=8.0 Hz, 1H), 6.88 (dd, J=11.8, 8.0 Hz, 1H), 5.41 (s, 1H), 5.11-5.01 (m, 1H), 4.28 (d, J=3.2 Hz, 1H), 2.59 (dd, J=14.8, 10.4 Hz, 1H), 2.39 (s, 3H), 2.30 (s, 3H), 2.04 (s, 3H), 1.94-1.88 (m, 1H), 1.28-1.24 (m, 9H).

Preparation 38

Isomer A of N-((2S)-2-(5-bromo-2,4-difluorophenyl)-4-(3,5-dimethylisoxazol-4-yl)-4-hydroxybutan-2-ylcarbamothioyl)benzamide

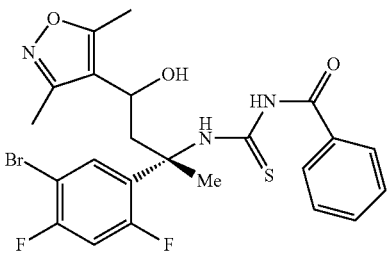 [SMILES: Cc1noc(C)c1C(O)C[C@](C)(NC(=S)NC(=O)c1ccccc1)c1cc(Br)c(F)cc1F]

To a solution of Isomer A of (3S)-3-amino-3-(5-bromo-2,4-difluorophenyl)-1-(3,5-dimethylisoxazol-4-yl)butan-1-ol (18 mg, 0.048 mmol) in CH$_2$Cl$_2$ (0.24 mL) at rt was added benzoyl isothiocyanate (10 μL, 0.077 mmol), and the reaction mixture was stirred at rt for 30 min. This mixture was purified by preparative TLC eluting with 30% EtOAc/Hexanes to give the title compound as a white solid (23 mg, 89% yield). $^1$H NMR (500 MHz, CHLOROFORM-d) δ 11.65 (s, 1H), 8.82 (s, 1H), 7.85 (dd, J=8.5, 1.1 Hz, 2H), 7.70-7.48 (m, 4H), 6.86 (dd, J=11.6, 8.1 Hz, 1H), 4.92 (dd, J=9.6, 2.7 Hz, 1H), 4.20-4.20 (m, 1H), 2.95 (s, 1H), 2.38 (s, 3H), 2.33 (3H, s), 2.21 (s, 3H).

Preparation 39

(4S,6S)-4-(5-bromo-2,4-difluorophenyl)-6-(3,5-dimethylisoxazol-4-yl)-4-methyl-5,6-dihydro-4H-1,3-thiazin-2-amine

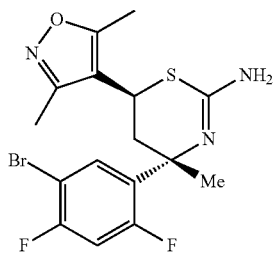 [SMILES: Cc1noc(C)c1[C@@H]1C[C@@](C)(c2cc(Br)c(F)cc2F)N=C(N)S1]

To a solution of isomer A of N-((2S)-2-(5-bromo-2,4-difluorophenyl)-4-(3,5-dimethylisoxazol-4-yl)-4-hydroxybutan-2-ylcarbamothioyl)benzamide (25 mg, 0.046 mmol) in dioxane (0.20 mL) was added 5N HCl (0.74 mL), and the reaction mixture was heated at 95° C. for 3 h. The solvent was removed in vacuo, and the residue was subjected to HPLC separation eluting with 0-100% A/B (A: 95% H$_2$O/5% MeCN, 10 MM NH$_4$OAc; B: 5% H$_2$O/95% MeCN, 10 mM NH$_4$OAC over 30 min period to give the title compound as a colorless oil (8 mg, 41% yield). $^1$H NMR (500 MHz, CHLOROFORM-d) δ 7.62-7.47 (m, 1H), 6.96 (dd, J=11.5, 7.9 Hz, 1H), 3.83 (d, J=11.3 Hz, 1H), 2.86 (d, J=14.0 Hz, 1H), 2.33 (s, 3H), 2.24 (s, 4H), 2.12-2.00 (m, 1H), 1.74 (s, 3H). MS (M+H)$^+$: 418.2

Preparation 40 tert-butyl (4S,6S)-4-(5-bromo-2,4-difluorophenyl)-6-(3,5-dimethylisoxazol-4-yl)-4-methyl-5,6-dihydro-4H-1,3-thiazin-2-ylcarbamate

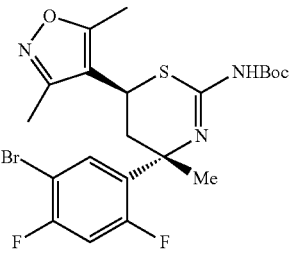 [SMILES: Cc1noc(C)c1[C@@H]1C[C@@](C)(c2cc(Br)c(F)cc2F)N=C(NC(=O)OC(C)(C)C)S1]

To a solution of (4S,6S)-4-(5-bromo-2,4-difluorophenyl)-6-(3,5-dimethylisoxazol-4-yl)-4-methyl-5,6-dihydro-4H-1,3-thiazin-2-amine (8 mg, 0.019 mmol) in dioxane (59 μL), saturated NaHCO$_3$ (59 μL) and water (9 μL) was added BOC$_2$O (9 mg, 0.038 mmol), and the reaction mixture was stirred at rt for 12 h. The reaction was partitioned between ethyl acetate and water, and the ethyl acetate layer was separated and dried to provide a crude product. The crude product was purified by preparative TLC eluting with 30% EtOAc/Hexanes to give the title compound as a white solid (8 mg, 81% yield). $^1$H NMR (500 MHz, CHLOROFORM-d) δ 7.55-7.43 (m, 1H), 6.98 (dd, J=11.4, 7.8 Hz, 1H), 3.73 (d, J=11.6 Hz, 1H), 2.87 (d, J=13.6 Hz, 1H), 2.31 (s, 3H), 2.22 (s, 2H), 2.21 (1H, m), 1.73 (br. s., 3H), 1.55 (s, 9H). MS (M+H)$^+$: 518.2.

Preparation 41 tert-butyl ((4S,6S)-4-(2,4-difluoro-5-(pyrimidin-5-yl)phenyl)-6-(3,5-dimethylisoxazol-4-yl)-4-methyl-5,6-dihydro-4H-1,3-thiazin-2-yl)carbamate

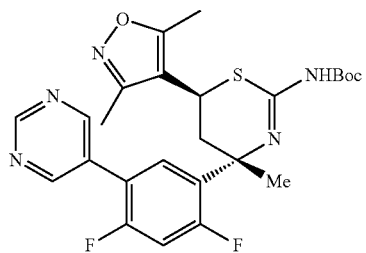 [SMILES: Cc1noc(C)c1[C@@H]1C[C@@](C)(c2cc(-c3cncnc3)c(F)cc2F)N=C(NC(=O)OC(C)(C)C)S1]

A mixture of bis(triphenylphosphine)palladium(II) chloride (2 mg), pyrimidin-5-ylboronic acid (8 mg), tert-butyl (4S,6S)-4-(5-bromo-2,4-difluorophenyl)-6-(3,5-dimethylisoxazol-4-yl)-4-methyl-5,6-dihydro-4H-1,3-thiazin-2-ylcarbamate (8 mg), cesium carbonate (20 mg) in DME (77 μL), EtOH (38 μL) and water (38 μL) was heated at 100° C. for 5 min, and the crude reaction mixture was subjected to HPLC separation eluting with 0-100% A/B (A: 95% H₂O/5% MeCN, 10 MM NH₄OAc; B: 5% H₂O/95% MeCN, 10 mM NH₄OAC over 12 min period to give the title compound as a white solid (3 mg). $^1$H NMR (500 MHz, CHLOROFORM-d) δ 9.29 (s, 1H), 8.95 (s, 2H), 7.39 (t, J=8.5 Hz, 1H), 7.17-7.04 (m, 1H), 3.76 (d, J=13.7 Hz, 1H), 2.94 (d, J=14.3 Hz, 1H), 2.32 (s, 3H), 2.24 (s, 3H), 1.78 (s, 3H), 1.53 (s, 9H). MS (M+H)⁺: 516.3.

Preparation 42

1-(2,4-difluoro-5-(pyrimidin-5-yl)phenyl)ethanol

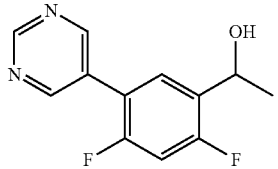 [SMILES: CC(O)c1cc(-c2cncnc2)c(F)cc1F]

To a solution of 2,4-difluoro-5-(pyrimidin-5-yl)benzaldehyde (2 g, 9.08 mmol, from Preparation 3) in ether (30.3 ml) was added MeMgBr (9.7 ml, 13.6 mmol), and the resulting white suspension was stirred at rt for 12 h and then heated at 75° C. for 3 h. Saturated ammonium chloride was added and the aqueous layer was extracted with EtOAc (×3). The combined organic layers were washed with brine, dried over anhydrous sodium sulfate, and filtered, and the filtrate was evaporated in vacuo to give the crude product. The crude product was purified by silica gel chromatography eluting with 10-80% EtOAc/Hexane to give 1-(2,4-difluoro-5-(pyrimidin-5-yl)phenyl)ethanol (1.2 g, 5.08 mmol, 55.9% yield) as a white solid. $^1$H NMR (500 MHz, CHLOROFORM-d) δ 9.24 (s, 1H), 8.97-8.77 (m, 2H), 7.66 (t, J=8.3 Hz, 1H), 6.99 (t, J=10.0 Hz, 1H), 5.27 (dd, J=6.2, 4.3 Hz, 1H), 2.14 (d, J=4.3 Hz, 1H), 1.58 (d, J=6.6 Hz, 3H).

Preparation 43

1-(2,4-difluoro-5-(pyrimidin-5-yl)phenyl)ethanone

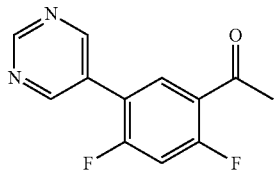 [SMILES: CC(=O)c1cc(-c2cncnc2)c(F)cc1F]

To a solution of oxalyl chloride (2.179 ml, 24.89 mmol) in DCM (2.5 mL) at −78° C. was added DMSO (3.53 ml, 49.8 mmol), and the reaction mixture was stirred at −78° C. for 30 min. A solution of the compound of preparation 42 (4.2 g, 17.78 mmol) in DCM (3.0 mL) was added dropwise, and the reaction mixture was stirred at −78° C. for 30 min.

Triethylamine (12.39 ml, 89 mmol) was added and the reaction mixture was then warmed up to rt over a 30 min period. Water was added and the aqueous layer was extracted with DCM (×3). The combined organic layers were washed with brine, dried over anhydrous sodium sulfate, and filtered, and the filtrate was evaporated in vacuo to give 1-(2,4-difluoro-5-(pyrimidin-5-yl)phenyl)ethanone (4.3 g, 18.36 mmol, 103% yield) as a yellow solid. $^1$H NMR (500 MHz, CHLOROFORM-d) δ 9.27 (s, 1H), 8.99-8.88 (m, 2H), 8.17-8.02 (m, 1H), 7.11 (t, J=10.1 Hz, 1H), 2.71 (d, J=5.2 Hz, 3H).

Preparation 44

(R,E)-N-(1-(2,4-difluoro-5-(pyrimidin-5-yl)phenyl)ethylidene)-2-methylpropane-2-sulfinamide

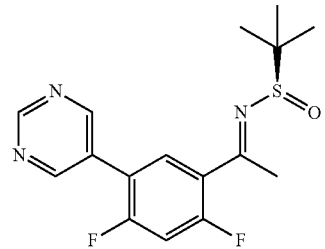 [SMILES: C/C(=N\[S@](=O)C(C)(C)C)c1cc(-c2cncnc2)c(F)cc1F]

A solution of (R)-2-methylpropane-2-sulfinamide (1.346 g, 11.10 mmol), 1-(2,4-difluoro-5-(pyrimidin-5-yl)phenyl)ethanone (2 g, 8.54 mmol) and 1-(2,4-difluoro-5-(pyrimidin-5-yl)phenyl)ethanone (2 g, 8.54 mmol) in THF (21.35 ml) was heated at 65° C. for 20 h. Water (30 mL) and EtOAc (50 mL) were added, and the resulting suspension was filtered through a pad of Celite. The aqueous layer was extracted with EtOAc (×3), and the combined organic layers were washed with brine, dried over anhydrous sodium sulfate, and filtered, and the filtrate was evaporated in vacuo to give the crude product. The crude product was purified by silica gel chromatography eluting with 20-60% EtOAc/Hexane to give (S,E)-N-(1-(2,4-difluoro-5-(pyrimidin-5-yl)phenyl)ethylidene)-2-methylpropane-2-sulfinamide (1.9 g, 5.63 mmol, 65.9% yield) as a yellow solid. $^1$H NMR (500 MHz, CHLOROFORM-d) δ 9.27 (s, 1H), 8.92 (d, J=1.4 Hz, 2H), 7.86 (t, J=8.2 Hz, 1H), 7.09 (t, J=10.2 Hz, 1H), 2.83 (d, J=3.5 Hz, 3H), 1.35-1.27 (m, 9H). MS (M+H)⁺: 338.11.

Preparation 45

(R)—N—((S)-2-(2,4-difluoro-5-(pyrimidin-5-yl)phenyl)-4-(3,5-dimethylisoxazol-4-yl)-4-oxobutan-2-yl)-2-methylpropane-2-sulfinamide

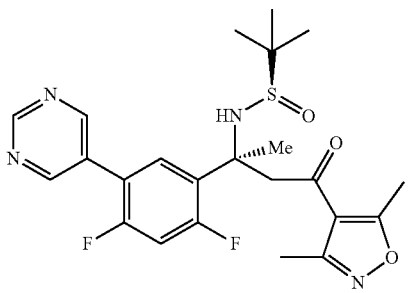 [SMILES: Cc1noc(C)c1C(=O)C[C@](C)(N[S@](=O)C(C)(C)C)c1cc(-c2cncnc2)c(F)cc1F]

To a solution of 1-(3,5-dimethylisoxazol-4-yl)ethanone (0.148 g, 1.067 mmol) in (8 mL) in THF (8 mL) at −78° C. was added n-BuLi (0.427 ml, 1.067 mmol) and the reaction mixture was stirred −78° C. for 20 min. A solution of (R,E)-N-(1-(2,4-difluoro-5-(pyrimidin-5-yl)phenyl)ethylidene)-2-methylpropane-2-sulfinamide (0.20 g, 0.593 mmol) in THF (1 mL) was added dropwise, and the reaction mixture was stirred at −78° C. for 30 min and then warmed up to −40° C. and stirred at −40° C. for 30 min. Water was added and the aqueous layer was extracted with EtOAc (×3). The combined organic layers were washed with brine, dried over anhydrous sodium sulfate, and filtered, and the filtrate was evaporated in vacuo to give the crude product. The crude product was purified by preparative TLC on silica gel (0.50 mm thickness) eluting with 90% EtOAc/Hexane to give (R)—N—((S)-2-(2,4-difluoro-5-(pyrimidin-5-yl)phenyl)-4-(3,5-dimethylisoxazol-4-yl)-4-oxobutan-2-yl)-2-methylpropane-2-sulfinamide (0.13 g, 0.273 mmol, 46.0% yield). $^1$H NMR $^1$H NMR (500 MHz, CHLOROFORM-d) δ 9.23 (s, 1H), 8.91 (d, J=1.2 Hz, 2H), 7.75 (t, J=8.8 Hz, 1H), 6.92 (dd, J=12.2, 9.8 Hz, 1H), 5.53 (s, 1H), 3.99-3.89 (m, 1H), 3.68 (dd, J=18.4, 2.8 Hz, 1H), 2.65 (s, 3H), 2.40 (s, 3H), 1.84 (s, 3H), 1.30 (s, 9H). MS (M+H)$^+$: 477.3.

Preparation 46

(R)—N-((2S,4R)-2-(2,4-difluoro-5-(pyrimidin-5-yl)phenyl)-4-(3,5-dimethylisoxazol-4-yl)-4-hydroxybutan-2-yl)-2-methylpropane-2-sulfinamide

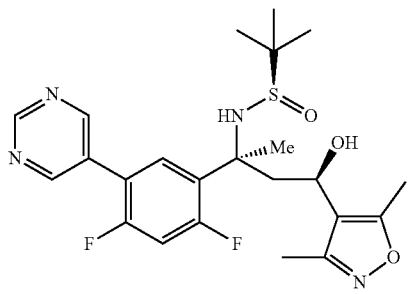 [SMILES: Cc1noc(C)c1[C@H](O)C[C@](C)(N[S@](=O)C(C)(C)C)c1cc(-c2cncnc2)c(F)cc1F]

To a solution of (R)—N—((S)-2-(2,4-difluoro-5-(pyrimidin-5-yl)phenyl)-4-(3,5-dimethylisoxazol-4-yl)-4-oxobutan-2-yl)-2-methylpropane-2-sulfinamide (47 mg, 0.099 mmol) in ether (658 μL) at −78° C. was added lithium tri-tert-butoxyaluminum hydride (493 μL, 0.493 mmol) dropwise, and the reaction mixture was stirred at −78° C. for 30 min. Another portion of lithium tri-tert-butoxyaluminum hydride (296 μL, 0.296 mmol) was added, and the reaction mixture was stirred at −78° C. for 20 min. A few crystals of sodium sulfate decahydrate were added, and the reaction mixture was diluted with 8 mL ether. Anhydrous sodium sulfate was added, and the reaction mixture was stirred at rt for 2 h and then filtered. The filtrate was evaporated in vacuo to give (R)-N-((2S,4R)-2-(2,4-difluoro-5-(pyrimidin-5-yl)phenyl)-4-(3,5-dimethylisoxazol-4-yl)-4-hydroxybutan-2-yl)-2-methylpropane-2-sulfinamide (43 mg, 0.090 mmol, 91% yield). The crude product was used directly for the next reaction without further purification. $^1$H NMR (500 MHz, CHLOROFORM-d) δ 9.26-9.20 (m, 1H), 8.93-8.84 (m, 2H), 7.57 (t, J=8.5 Hz, 1H), 6.99 (dd, J=11.7, 9.8 Hz, 1H), 5.82 (s, 1H), 5.09 (d, J=10.5 Hz, 1H), 4.91 (br. s., 1H), 2.68 (dd, J=14.7, 10.8 Hz, 1H), 2.39 (s, 3H), 2.30 (s, 3H), 2.13-2.09 (m, 3H), 1.91 (br. s., 1H), 1.87 (dd, J=14.8, 2.1 Hz, 1H), 1.25-1.22 (m, 9H). MS (M−H)$^−$: 477.3.

Preparation 47

(1R,3S)-3-amino-3-(2,4-difluoro-5-(pyrimidin-5-yl)phenyl)-1-(3,5-dimethylisoxazol-4-yl)butan-1-ol

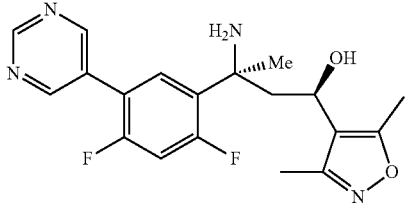 [SMILES: Cc1noc(C)c1[C@H](O)C[C@](C)(N)c1cc(-c2cncnc2)c(F)cc1F]

To a solution of (R)—N-((2S,4R)-2-(2,4-difluoro-5-(pyrimidin-5-yl)phenyl)-4-(3,5-dimethylisoxazol-4-yl)-4-hydroxybutan-2-yl)-2-methylpropane-2-sulfinamide (50 mg, 0.104 mmol) in DCM at rt was added HCl (261 μL, 1.045 mmol), and the reaction mixture was stirred at rt for 10 min. The solvents were removed under high vacuum. Water was added and the aqueous layer was extracted with DCMc (×3). The combined organic layers were washed with brine, dried over anhydrous sodium sulfate, and filtered, and the filtrate was evaporated in vacuo to give the crude product. The crude product was purified by preparative TLC on silica gel (0.50 mm thickness) eluting with 90% DCM/9% MeOH/1% ammonium hydroxide to give (1R,3S)-3-amino-3-(2,4-difluoro-5-(pyrimidin-5-yl)phenyl)-1-(3,5-dimethylisoxazol-4-yl)butan-1-ol (21.4 mg, 0.057 mmol, 54.7% yield) as a colorless oil. $^1$H NMR (500 MHz, CHLOROFORM-d) δ 9.25 (s, 1H), 8.95-8.82 (m, 2H), 7.41 (t, J=8.6 Hz, 1H), 7.04 (dd, J=12.0, 9.7 Hz, 1H), 5.12 (dd, J=11.1, 2.1 Hz, 1H), 2.45-2.36 (m, 3H), 2.32 (s, 3H), 2.26 (dd, J=14.1, 11.1 Hz, 1H), 1.88 (dd, J=14.3, 2.3 Hz, 1H), 1.80 (s, 3H). MS (M+H)$^+$: 375.25.

Preparation 48

N-(((2S,4R)-2-(2,4-difluoro-5-(pyrimidin-5-yl)phenyl)-4-(3,5-dimethylisoxazol-4-yl)-4-hydroxybutan-2-yl)carbamothioyl)benzamide

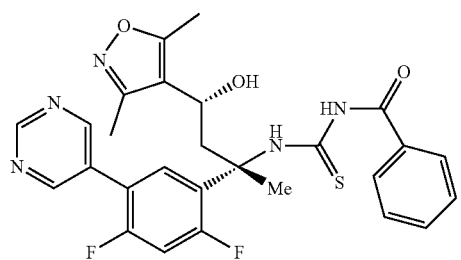 [SMILES: Cc1noc(C)c1[C@H](O)C[C@](C)(NC(=S)NC(=O)c1ccccc1)c1cc(-c2cncnc2)c(F)cc1F]

To a solution of (1R,3S)-3-amino-3-(2,4-difluoro-5-(pyrimidin-5-yl)phenyl)-1-(3,5-dimethylisoxazol-4-yl)butan-1-ol (50 mg, 0.134 mmol) in CH2Cl2 (668 μL) at rt was added benzoyl isothiocyanate (27.0 μL, 0.200 mmol), and the reaction mixture was stirred at rt for 30 min. The solvent was removed, and the residue was purified by preparative TLC on silica gel (0.50 mm thickness) eluting with 60% EtOAc/

Hexane to give N-(((2S,4R)-2-(2,4-difluoro-5-(pyrimidin-5-yl)phenyl)-4-(3,5-dimethylisoxazol-4-yl)-4-hydroxybutan-2-yl)carbamothioyl)benzamide (50 mg, 0.093 mmol, 69.6% yield). $^1$H NMR (500 MHz, CHLOROFORM-d) δ 11.74 (s, 1H), 9.23 (s, 1H), 8.93 (d, J=1.2 Hz, 2H), 8.86 (s, 1H), 7.90-7.83 (m, 2H), 7.68-7.62 (m, 1H), 7.56-7.52 (m, 2H), 7.49 (t, J=8.5 Hz, 1H), 6.98 (dd, J=11.7, 9.8 Hz, 1H), 4.99 (dt, J=9.8, 2.7 Hz, 1H), 3.04 (dd, J=14.6, 9.8 Hz, 1H), 2.42 (dd, J=3.0, 1.3 Hz, 1H), 2.40 (s, 3H), 2.34 (s, 3H), 2.27 (s, 3H), 2.28-2.24 (m, 1H), 2.17 (d, J=13.7 Hz, 1H). MS (M−H)$^-$: 536.4.

Preparation 49

1-(2,5-dimethyloxazol-4-yl)ethanol

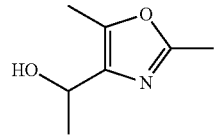

To a solution of 2,5-dimethyloxazole-4-carbaldehyde (1 g, 7.99 mmol) in ether (26.6 ml) at rt was added methylmagnesium bromide (7.99 ml, 11.19 mmol) dropwise, and the reaction mixture was stirred at rt for 1 h. Hydrochloric acid (11.19 ml, 11.19 mmol) was added, and the aqueous layer was extracted with EtOAc (×3). The combined organic layers were washed with brine, dried over anhydrous sodium sulfate, and filtered, and the filtrate was evaporated in vacuo to give the crude product (1.2 g, 100%). This crude product was used without purification. $^1$H NMR (500 MHz, CHLOROFORM-d) δ 4.79 (quin, J=6.4 Hz, 1H), 2.41 (s, 3H), 2.30 (s, 3H), 1.53 (d, J=6.6 Hz, 3H).

Preparation 50

1-(2,5-dimethyloxazol-4-yl)ethanone

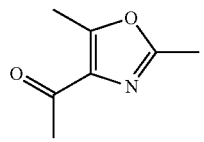

A mixture of 1-(2,5-dimethyloxazol-4-yl)ethanol (1.2 g, 8.50 mmol) and MnO$_2$ (3.70 g, 42.5 mmol) in chloroform (85 ml) was heated at 75° C. for 12 h, and the reaction mixture was then filtered through a pad of celite. The filtrate was evaporated in vacuo to give 1-(2,5-dimethyloxazol-4-yl)ethanone (750 mg, 5.39 mmol, 63.4% yield) as a slightly yellow oil, which solidified upon standing at rt. $^1$H NMR (500 MHz, CHLOROFORM-d) δ 2.59 (s, 3H), 2.52 (s, 3H), 2.46 (s, 3H).

Preparation 51

(R)—N—((S)-2-(2,4-difluoro-5-(pyrimidin-5-yl)phenyl)-4-(2,5-dimethyloxazol-4-yl)-4-oxobutan-2-yl)-2-methylpropane-2-sulfinamide

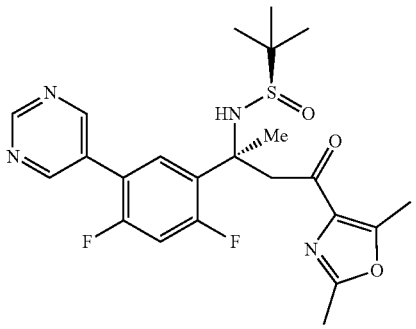 [SMILES: Cc1nc(C(=O)C[C@](C)(N[S@](=O)C(C)(C)C)c2cc(-c3cncnc3)c(F)cc2F)c(C)o1]

To a solution of 1-(2,5-dimethyloxazol-4-yl)ethanone (74.2 mg, 0.534 mmol) in THF (741 μL) at −78° C. was added potassium hexamethyldisilazide (1186 μL, 0.593 mmol), and the reaction mixture was stirred at −78° C. for 1 h. Then a solution of (R,E)-N-(1-(2,4-difluoro-5-(pyrimidin-5-yl)phenyl)ethylidene)-2-methylpropane-2-sulfinamide (100 mg, 0.296 mmol) in THF (0.30 mL) was added, and the reaction mixture was stirred at −78° C. for 2 h. Water was added and the aqueous layer was extracted with EtOAc (×3). The combined organic layers were washed with brine, dried over anhydrous sodium sulfate, and filtered, and the filtrate was evaporated in vacuo to give the crude product. The crude product was purified by preparative TLC on silica gel (0.50 mm thickness) eluting with 90% EtOAc/Hexane to give (R)—N—((S)-2-(2,4-difluoro-5-(pyrimidin-5-yl)phenyl)-4-(2,5-dimethyloxazol-4-yl)-4-oxobutan-2-yl)-2-methylpropane-2-sulfinamide (38 mg, 0.080 mmol, 26.9% yield). $^1$H NMR (500 MHz, CHLOROFORM-d) δ 9.23 (s, 1H), 8.95-8.79 (m, 2H), 7.69 (t, J=8.7 Hz, 1H), 6.93 (dd, J=11.7, 9.9 Hz, 1H), 5.67 (s, 1H), 4.16 (dd, J=18.6, 1.2 Hz, 1H), 3.72 (dd, J=18.5, 1.7 Hz, 1H), 2.51 (s, 3H), 2.44 (s, 3H), 1.87 (s, 3H), 1.30 (s, 9H).

Preparation 52

(R)—N-((2S,4R)-2-(2,4-difluoro-5-(pyrimidin-5-yl)phenyl)-4-(2,5-dimethyloxazol-4-yl)-4-hydroxybutan-2-yl)-2-methylpropane-2-sulfinamide

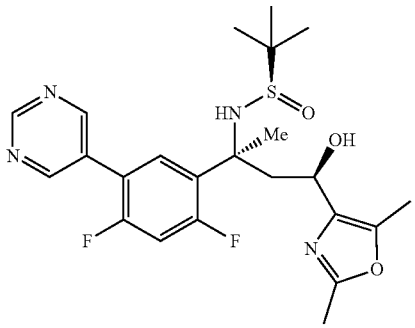 [SMILES: Cc1nc([C@H](O)C[C@](C)(N[S@](=O)C(C)(C)C)c2cc(-c3cncnc3)c(F)cc2F)c(C)o1]

To a solution of (R)—N—((S)-2-(2,4-difluoro-5-(pyrimidin-5-yl)phenyl)-4-(2,5-dimethyloxazol-4-yl)-4-oxobutan-2-yl)-2-methylpropane-2-sulfinamide (194 mg, 0.407 mmol) in ether (1628 μL) at −78° C. was added lithium tri-tert-butoxyaluminum hydride (1628 μL, 1.628 mmol), and the reaction mixture was stirred at −78° C. for 20 min. The reaction mixture was warmed up to −20° C. over a period of 20 min, and the reaction was complete. A few crystals of sodium sulfate decahydrate were added followed by ether and anhydrous sodium sulfate, and the reaction mixture was stirred at rt for 2 h and then filtered and washed with ethyl acetate. The filtrate was evaporated in vacuo to give the crude product. The crude product was purified by preparative TLC on silica gel (1 mm thickness, 3 plates) eluting with 60% acetone/hexane to give (R)—N-((2S,4R)-2-(2,4-difluoro-5-(pyrimidin-5-yl)phenyl)-4-(2,5-dimethyloxazol-4-yl)-4-hydroxybutan-2-yl)-2-methylpropane-2-sulfinamide (155 mg, 0.324 mmol, 80% yield) as a colorless oil. $^1$H NMR (500 MHz, CHLOROFORM-d) δ 9.24 (s, 1H), 8.90 (d, J=1.4 Hz, 2H), 7.59 (t, J=8.5 Hz, 1H), 6.96 (dd, J=11.7, 9.9 Hz, 1H), 5.60 (s, 1H), 5.06 (td, J=5.0, 2.6 Hz, 1H), 4.01 (d, J=5.0 Hz, 1H), 2.74 (dd, J=14.9, 10.0 Hz, 1H), 2.33 (s, 3H), 2.28 (s, 3H), 2.14 (dd, J=14.9, 2.4 Hz, 1H), 2.08 (s, 3H), 1.27 (s, 9H).

Preparation 53

(1R,3S)-3-amino-3-(2,4-difluoro-5-(pyrimidin-5-yl)phenyl)-1-(2,5-dimethyloxazol-4-yl)butan-1-ol

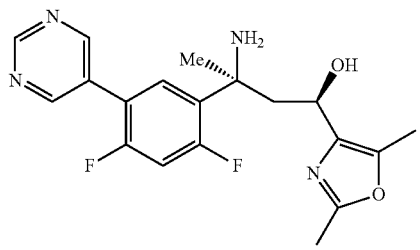 [SMILES: Cc1nc([C@H](O)C[C@](C)(N)c2cc(-c3cncnc3)c(F)cc2F)c(C)o1]

To a solution of (R)—N-((2S,4R)-2-(2,4-difluoro-5-(pyrimidin-5-yl)phenyl)-4-(2,5-dimethyloxazol-4-yl)-4-hydroxybutan-2-yl)-2-methylpropane-2-sulfinamide (154 mg, 0.322 mmol) in methanol (1287 μL) at rt was added hydrochloric acid in dioxane (805 μL, 3.22 mmol), and the reaction mixture was stirred at rt for 10 min. The reaction was complete by LC/MS analysis (TFA conditions). The solvents were removed completely, saturated sodium bicarbonate was added, and the aqueous layer was extracted with DCM (×3). The combined organic layers were washed with brine, dried over anhydrous sodium sulfate, and filtered, and the filtrate was evaporated in vacuo to give the crude product. The crude product was purified by preparative TLC on silica gel (0.50 mm thickness, 3 plates) eluting with 90% DCM/9% MeOH/1% ammonium hydroxide to give (1R,3S)-3-amino-3-(2,4-difluoro-5-(pyrimidin-5-yl)phenyl)-1-(2,5-dimethyloxazol-4-yl)butan-1-ol (88 mg, 0.235 mmol, 73.0% yield) as a colorless oil. $^1$H NMR (500 MHz, CHLOROFORM-d) δ 9.22 (s, 1H), 8.88 (s, 2H), 7.41 (t, J=8.6 Hz, 1H), 7.04-6.89 (m, 1H), 5.08 (d, J=10.8 Hz, 1H), 3.54-3.40 (m, 2H), 2.44-2.28 (1H, m), 2.35 (s, 3H), 2.31 (s, 3H), 2.05 (d, J=14.3 Hz, 1H), 1.77 (s, 3H). MS (M+H)$^+$: 375.3.

Preparation 54

N-(((2S,4R)-2-(2,4-difluoro-5-(pyrimidin-5-yl)phenyl)-4-(2,5-dimethyloxazol-4-yl)-4-hydroxybutan-2-yl)carbamothioyl)benzamide

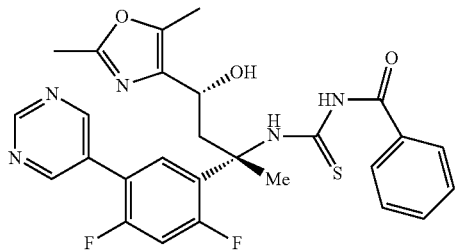 [SMILES: Cc1nc([C@H](O)C[C@](C)(NC(=S)NC(=O)c2ccccc2)c2cc(-c3cncnc3)c(F)cc2F)c(C)o1]

To a solution of (1R,3S)-3-amino-3-(2,4-difluoro-5-(pyrimidin-5-yl)phenyl)-1-(2,5-dimethyloxazol-4-yl)butan-1-ol (88 mg, 0.235 mmol) in DCM (1567 μL) at rt was added Benzoyl isothiocyanate (37.9 μL, 0.282 mmol), and the reaction mixture was stirred at rt for 30 min. The solvent was removed, and the residue was purified by preparative TLC on silica gel (0.50 mm thickness, 3 plates) eluting with 75% EtOAc/Hexane to give N-(((2S,4R)-2-(2,4-difluoro-5-(pyrimidin-5-yl)phenyl)-4-(2,5-dimethyloxazol-4-yl)-4-hydroxybutan-2-yl)carbamothioyl)benzamide (115 mg, 0.214 mmol, 91% yield). $^1$H NMR (500 MHz, CHLOROFORM-d) δ 11.74 (s, 1H), 9.24 (s, 1H), 8.94 (d, J=1.2 Hz, 2H), 8.81 (s, 1H), 7.90-7.85 (m, 2H), 7.69-7.60 (m, 1H), 7.57-7.45 (m, 3H), 6.95 (dd, J=11.6, 9.9 Hz, 1H), 4.91 (br. s., 1H), 2.97 (dd, J=14.5, 9.3 Hz, 1H), 2.50 (d, J=6.3 Hz, 1H), 2.38 (s, 3H), 2.32 (dd, J=14.7, 3.3 Hz, 1H), 2.29-2.24 (m, 6H), 1.63 (s, 5H). MS (M+H)$^+$: 538.3.

Preparation 55

1-(2,4-dimethyloxazol-5-yl)ethanol

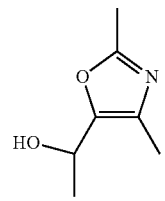

To a solution of 2,4-dimethyloxazole-5-carbaldehyde (0.8 g, 6.39 mmol) in THF (21.31 ml) at rt was added MeMgBr (5.94 ml, 8.31 mmol), and the reaction mixture was stirred at rt for 1 h. 1N HCl (8.31 ml, 8.31 mmol) was added, and the aqueous layer was extracted with EtOAc (×3). The combined organic layers were washed with brine, dried over anhydrous sodium sulfate, and filtered, and the filtrate was evaporated in vacuo to give the crude product. This product was used directly for the oxidation reaction. $^1$H NMR (500 MHz, CHLOROFORM-d) δ 5.00-4.88 (m, 1H), 2.42 (s, 3H), 2.38 (s, 3H), 1.56 (d, J=6.6 Hz, 3H).

Preparation 56

1-(2,4-dimethyloxazol-5-yl)ethanone

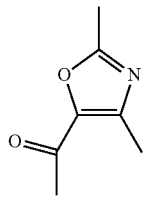

A suspension of 1-(2,4-dimethyloxazol-5-yl)ethanol (0.9 g, 6.38 mmol) and manganese dioxide (2.77 g, 31.9 mmol) in chloroform (63.8 ml) was heated at 75° C. for 12 h. Another 2 g portion of MnO$_2$ was added, and the reaction mixture was heated at reflux for 48 h. The mixture was filtered through a pad of Celite, and the filtrate was evaporated in vacuo to give 1-(2,4-dimethyloxazol-5-yl)ethanone (0.43 g, 3.09 mmol, 48.5% yield) as a yellow solid. $^1$H NMR (500 MHz, CHLOROFORM-d) δ 2.52 (s, 3H), 2.47 (s, 3H), 2.47 (s, 3H).

Preparation 57

(R)—N—((S)-2-(2,4-difluoro-5-(pyrimidin-5-yl)phenyl)-4-(2,4-dimethyloxazol-5-yl)-4-oxobutan-2-yl)-2-methylpropane-2-sulfinamide

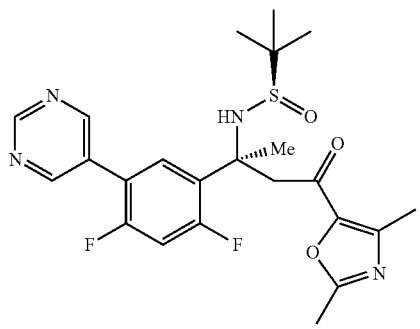 [SMILES: Cc1nc(C)c(C(=O)C[C@](C)(N[S@](=O)C(C)(C)C)c2cc(-c3cncnc3)c(F)cc2F)o1]

To a solution of KHMDS (5.10 ml, 2.55 mmol) in THF (30 mL) at −78° C. was added a solution of 1-(2,4-dimethyloxazol-5-yl)ethanone (0.319 g, 2.294 mmol) in THF (3.0 mL) and a pink solution was formed. This solution was stirred at −78° C. for 1 h, then a solution of (R,E)-N-(1-(2,4-difluoro-5-(pyrimidin-5-yl)phenyl)ethylidene)-2-methylpropane-2-sulfinamide (0.43 g, 1.274 mmol) in THF (3 mL) was added dropwise, and the reaction mixture was stirred at −78° C. for 2 h. Water was added and the aqueous layer was extracted with EtOAc (×3). The combined organic layers were washed with brine, dried over anhydrous sodium sulfate, and filtered, and the filtrate was evaporated in vacuo to give the crude product. The crude product was purified by preparative TLC on silica gel (1 mm thickness, 4 plates) eluting with 7% EtOAc/Hexane to give (R)—N—((S)-2-(2,4-difluoro-5-(pyrimidin-5-yl)phenyl)-4-(2,4-dimethyloxazol-5-yl)-4-oxobutan-2-yl)-2-methylpropane-2-sulfinamide (0.228 g, 0.478 mmol, 37.5% yield) as a yellow foam. $^1$H NMR (500 MHz, CHLOROFORM-d) δ 9.24 (s, 1H), 8.91 (d, J=1.4 Hz, 2H), 7.73 (t, J=8.7 Hz, 1H), 6.94 (dd, J=11.9, 9.8 Hz, 1H), 5.58 (s, 1H), 4.10-3.98 (m, 1H), 3.68 (dd, J=18.6, 2.1 Hz, 1H), 2.51 (s, 3H), 2.39 (s, 3H), 1.88 (s, 3H), 1.31 (s, 9H).

Preparation 58

(R)—N-((2S,4R)-2-(2,4-difluoro-5-(pyrimidin-5-yl)phenyl)-4-(2,4-dimethyloxazol-5-yl)-4-hydroxybutan-2-yl)-2-methylpropane-2-sulfinamide

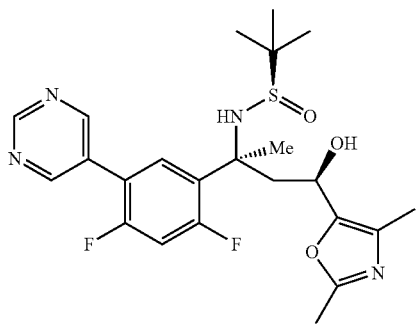 [SMILES: Cc1nc(C)c([C@H](O)C[C@](C)(N[S@](=O)C(C)(C)C)c2cc(-c3cncnc3)c(F)cc2F)o1]

To a solution of (R)—N—((S)-2-(2,4-difluoro-5-(pyrimidin-5-yl)phenyl)-4-(2,4-dimethyloxazol-5-yl)-4-oxobutan-2-yl)-2-methylpropane-2-sulfinamide (240 mg, 0.504 mmol) in ether (2518 μL) at −78° C. was added lithium tri-tert-butoxyaluminum hydride (2015 μL, 2.015 mmol), and the reaction mixture was stirred at −78° C. for 20 min and then warmed up to −25° C. over a period of 35 min. A few crystals of sodium sulfate decahydrate were added followed by ether, the reaction mixture was stirred at rt for 2 h and then filtered, and the solid material was washed with ethyl acetate. The combined filtrate was evaporated in vacuo to give the crude product. The crude product was purified by preparative TLC on silica gel (1 mm thickness, 3 plates) eluting with 60% acetone/hexane to give (R)—N-((2S,4R)-2-(2,4-difluoro-5-(pyrimidin-5-yl)phenyl)-4-(2,4-dimethyloxazol-5-yl)-4-hydroxybutan-2-yl)-2-methylpropane-2-sulfinamide (213 mg, 0.445 mmol, 88% yield) as a colorless oil. $^1$H NMR (500 MHz, CHLOROFORM-d) δ 9.25 (s, 1H), 8.90 (d, J=1.4 Hz, 2H), 7.57 (t, J=8.5 Hz, 1H), 6.99 (dd, J=11.7, 9.8 Hz, 1H), 5.47 (s, 1H), 5.20 (d, J=10.1 Hz, 1H), 4.56 (br. s., 1H), 2.80 (dd, J=14.9, 10.0 Hz, 1H), 2.35 (s, 3H), 2.16-2.10 (m, 1H), 2.12 (s, 3H), 2.09 (s, 3H), 1.72 (s, 4H), 1.27 (s, 9H).

Preparation 59

(1R,3S)-3-amino-3-(2,4-difluoro-5-(pyrimidin-5-yl)phenyl)-1-(2,4-dimethyloxazol-5-yl)butan-1-ol

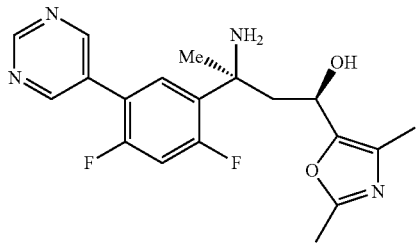 [SMILES: Cc1nc(C)c([C@H](O)C[C@](C)(N)c2cc(-c3cncnc3)c(F)cc2F)o1]

To a solution of (R)—N-((2S,4R)-2-(2,4-difluoro-5-(pyrimidin-5-yl)phenyl)-4-(2,4-dimethyloxazol-5-yl)-4-hydroxybutan-2-yl)-2-methylpropane-2-sulfinamide (210 mg, 0.439 mmol) in methanol (1755 μL) at rt was added 1N HCl in dioxane (1097 μL, 4.39 mmol), and the reaction mixture was stirred at rt for 10 min. The solvents were removed completely, saturated sodium bicarbonate was added, and the aqueous layer was extracted with DCM (×3). The combined organic layers were washed with brine, dried over anhydrous sodium sulfate, and filtered, and the filtrate was evaporated in vacuo to give the crude product. The crude product was purified by preparative TLC on silica gel (1 mm thickness, 2 plates) eluting with 90% DCM/9% MeOH/1% ammonium hydroxide to give (1R,3S)-3-amino-3-(2,4-difluoro-5-(pyrimidin-5-yl)phenyl)-1-(2,4-dimethyloxazol-5-yl)butan-1-ol (152 mg, 0.406 mmol, 93% yield) as a colorless oil. $^1$H NMR (500 MHz, CHLOROFORM-d) δ 9.22 (s, 1H), 8.88 (s, 2H), 7.40 (t, J=8.6 Hz, 1H), 7.09-6.89 (m, 1H), 5.18 (d, J=10.7 Hz, 1H), 2.50-2.41 (m, 1H), 2.36 (s, 3H), 2.12 (s, 3H), 1.98 (dd, J=14.3, 2.6 Hz, 1H), 1.77 (s, 3H). MS (M+H)$^+$: 375.2.

Preparation 60

N-(((2S,4R)-2-(2,4-difluoro-5-(pyrimidin-5-yl)phenyl)-4-(2,4-dimethyloxazol-5-yl)-4-hydroxybutan-2-yl)carbamothioyl)benzamide

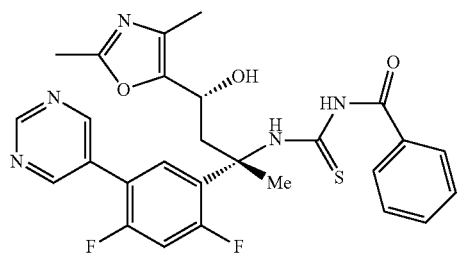 [SMILES: Cc1nc(C)c([C@H](O)C[C@](C)(NC(=S)NC(=O)c2ccccc2)c2cc(-c3cncnc3)c(F)cc2F)o1]

To a solution of (1R,3S)-3-amino-3-(2,4-difluoro-5-(pyrimidin-5-yl)phenyl)-1-(2,4-dimethyloxazol-5-yl)butan-1-ol (145 mg, 0.387 mmol) in DCM (2582 μL) at rt was added benzoyl isothiocyanate (62.5 μL, 0.465 mmol), and the reaction mixture was stirred at rt for 30 min. TLC (80% EtOAc/hexane) and LC/MS showed complete reaction. The solvent was removed, and the residue was purified by preparative TLC on silica gel (0.50 mm thickness, 3 plates) eluting with 75% EtOAc/Hexane to give N-(((2S,4R)-2-(2,4-difluoro-5-(pyrimidin-5-yl)phenyl)-4-(2,4-dimethyloxazol-5-yl)-4-hydroxybutan-2-yl)carbamothioyl)benzamide (192 mg, 0.357 mmol, 92% yield) as a white foam. $^1$H NMR (500 MHz, CHLOROFORM-d) δ 11.70 (s, 1H), 9.24 (s, 1H), 8.93 (d, J=1.2 Hz, 2H), 7.94-7.84 (m, 2H), 7.68-7.63 (m, 1H), 7.57-7.51 (m, 2H), 7.45 (t, J=8.5 Hz, 1H), 6.96 (dd, J=11.6, 9.9 Hz, 1H), 5.05 (dt, J=8.6, 4.2 Hz, 1H), 3.13 (dd, J=14.6, 8.6 Hz, 1H), 2.47 (d, J=4.6 Hz, 1H), 2.48-2.39 (m, 1H), 2.38 (s, 3H), 2.19 (s, 4H), 2.10 (s, 3H). MS (M+H)$^+$: 539.4.

Preparation 61

2-bromo-3-chlorothiophene

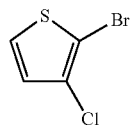

To a solution of 3-chlorothiophene (15 g, 126 mmol) in dioxane (42.2 ml) at 0° C. was added bromine (7.01 ml, 136 mmol) dropwise over 30 min. When the addition was complete, the reaction mixture was brought to 60° C. and stirred overnight. The mixture was then allowed to come to rt at which time it was washed with saturated aqueous sodium bicarbonate (3×15 mL). The remaining organic layer was dried over MgSO$_4$, filtered and concentrated in vacuo. Distillation of the resulting oil (lit. BP: 194° C./760 mm Hg, 47° C./0.1 mm Hg) gave 2-bromo-3-chlorothiophene (18.2 g, 92 mmol, 72.9% yield) as a clear, colorless oil containing some impurities. This was used as-is; $^1$H NMR (500 MHz, CHLOROFORM-d) δ 7.33-7.24 (m, 2H), 6.90 (d, J=5.8 Hz, 1H) with impurities showing between 4.0 and 3.5 ppm.

Preparation 62

1-(5-bromo-3-chlorothiophen-2-yl)ethanone

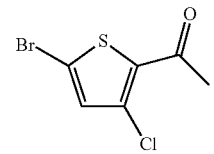

To a solution of diisopropylamine (6.62 ml, 46.4 mmol) in THF (57.2 ml) at −78° C. was added a solution of BuLi (18.57 ml, 46.4 mmol) dropwise. When the addition was complete, the reaction mixture was allowed to stir at −78° C. for an additional 30 min. A solution of 2-bromo-3-chlorothiophene (Preparation 61, 9.17 g, 46.4 mmol) in THF (11.43 ml) was then added rapidly in one aliquot. The resulting mixture was stirred at −78° C. for 30 min. A solution of N-methoxy-N-methylacetamide (1.915 g, 18.57 mmol) in THF (5.72 ml) was then added dropwise to the reaction mixture, which was then allowed to stir for an additional 30 min at −78° C. The reaction mixture was then quenched by the slow addition of 1N HCl (120 mL). After coming to rt, the mixture was extracted with ether (3×50 mL). The combined extracts were washed with water (50 mL), dried over MgSO$_4$, filtered and concentrated in vacuo. Purification by flash chromatography (silica, EtOAc/Hexanes) gave 1-(5-bromo-3-chlorothiophen-2-yl)ethanone (100% yield); $^1$H NMR (500 MHz, CHLOROFORM-d) δ 7.03 (s, 1H), 3.86 (t, J=6.2 Hz, 1H), 3.50 (t, J=6.3 Hz, 1H), 2.65 (s, 3H).

Preparation 63 tert-butyl (4S,6S)-4-(5-bromo-3-chlorothiophen-2-yl)-6-(3,5-dimethylisoxazol-4-yl)-4-methyl-5,6-dihydro-4H-1,3-thiazin-2-ylcarbamate

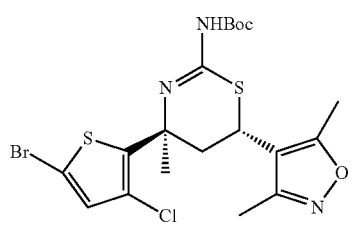 [SMILES: Cc1noc(C)c1[C@@H]1C[C@@](C)(c2sc(Br)cc2Cl)N=C(NC(=O)OC(C)(C)C)S1]

This compound was prepared in a similar manner to the preparation of tert-butyl ((4S,6S)-4-(5-bromo-2,4-difluorophenyl)-6-(3,5-dimethylisoxazol-4-yl)-4-methyl-5,6-dihydro-4H-1,3-thiazin-2-yl)carbamate (Preparation 40) from 1-(5-bromo-3-chlorothiophen-2-yl)ethanone (Preparation 62, 1.5 g, 6.26 mmol). Tert-butyl (4S,6S)-4-(5-bromo-3-chlorothiophen-2-yl)-6-(3,5-dimethylisoxazol-4-yl)-4-methyl-5,6-dihydro-4H-1,3-thiazin-2-ylcarbamate (47.2 mg, 0.091 mmol) was obtained. LC-MS (M+H)$^+$=522.1; $^1$H NMR (500 MHz, CHLOROFORM-d) δ 6.92 (s, 1H), 3.98 (d, J=10.1 Hz, 1H), 3.16 (dd, J=14.0, 2.8 Hz, 1H), 2.37-2.31 (m, 3H), 2.31-2.21 (m, 3H), 2.09-1.94 (m, 1H), 1.73 (br. s., 3H), 1.54-1.48 (m, 9H).

Preparation 64 tert-butyl (4S,6S)-4-(3-chloro-5-(5-(prop-1-ynyl)pyridin-3-yl)thiophen-2-yl)-6-(3,5-dimethylisoxazol-4-yl)-4-methyl-5,6-dihydro-4H-1,3-thiazin-2-ylcarbamate

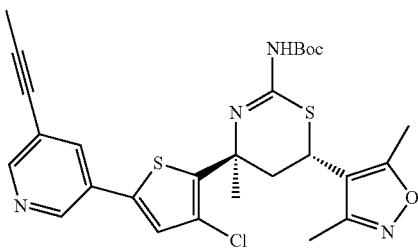 [SMILES: CC#Cc1cncc(-c2cc(Cl)c([C@]3(C)C[C@@H](c4c(C)noc4C)SC(NC(=O)OC(C)(C)C)=N3)s2)c1]

To a solution of tert-butyl ((4S,6S)-4-(5-bromo-3-chlorothiophen-2-yl)-6-(3,5-dimethylisoxazol-4-yl)-4-methyl-5,6-dihydro-4H-1,3-thiazin-2-yl)carbamate (Preparation 63, 11.5 mg, 0.022 mmol) and (5-(prop-1-yn-1-yl)pyridin-3-yl)boronic acid (Preparation 14, 3.73 mg, 0.023 mmol) in DME (100 μL), EtOH (50.2 μL), and H$_2$O (50.2 μL) was added Bis(triphenylphosphine)palladium(II) chloride (3.10 mg, 4.42 μmol) and cesium carbonate (10.79 mg, 0.033 mmol). The resulting mixture was brought to 90° C. and stirred for 1 h. The mixture was then diluted with EtOAc (10 mL), washed with water (2×4 mL), brine (4 mL), dried over MgSO$_4$, filtered and concentrated in vacuo. Purification by flash chromatography (Silica, EtOAc/Hexanes) gave tert-butyl ((4S,6S)-4-(3-chloro-5-(5-(prop-1-yn-1-yl)pyridin-3-yl)thiophen-2-yl)-6-(3,5-dimethylisoxazol-4-yl)-4-methyl-5,6-dihydro-4H-1,3-thiazin-2-yl)carbamate (4.1 mg, 7.36 μmol, 33.3% yield); LC-MS (M+H)$^+$=557.2; $^1$H NMR (500 MHz, CHLOROFORM-d) δ 8.71-8.68 (m, 1H), 8.55 (d, J=1.7 Hz, 1H), 7.82 (t, J=2.1 Hz, 1H), 7.22 (s, 1H), 4.02 (d, J=12.2 Hz, 1H), 3.23 (dd, J=14.0, 2.9 Hz, 1H), 2.35 (s, 3H), 2.31-2.21 (m, 3H), 2.15-2.08 (m, 5H), 1.81 (br. s., 3H), 1.56-1.52 (m, 9H).

Preparation 65 tert-butyl (4S,6R)-4-(2,4-difluorophenyl)-6-(3,5-dimethylisoxazol-4-yl)-4-methyl-5,6-dihydro-4H-1,3-thiazin-2-ylcarbamate

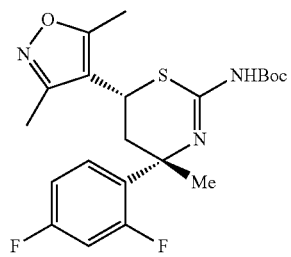 [SMILES: Cc1noc(C)c1[C@H]1C[C@@](C)(c2ccc(F)cc2F)N=C(NC(=O)OC(C)(C)C)S1]

To a solution of tert-butyl ((4S,6R)-4-(5-bromo-2,4-difluorophenyl)-6-(3,5-dimethylisoxazol-4-yl)-4-methyl-5,6-dihydro-4H-1,3-thiazin-2-yl)carbamate (Preparation 40, 30 mg, 0.058 mmol) in THF (1162 μL) at −78° C. was added n-butyllithium (93 μL, 0.232 mmol) dropwise. The resulting mixture was stirred at −78° C. for 20 min. The reaction mixture was quenched by the addition of water (5 mL) and extracted with EtOAc (3×2 mL). The combined extracts were washed with brine (2 mL), dried over MgSO$_4$, filtered and concentrated in vacuo. Purification by flash chromatography (Silica, EtOAc/Hexanes) gave tert-butyl ((4S,6R)-4-(2,4-difluorophenyl)-6-(3,5-dimethylisoxazol-4-yl)-4-methyl-5,6-dihydro-4H-1,3-thiazin-2-yl)carbamate (21.5 mg, 0.049 mmol, 85% yield); LC-MS (M+H)$^+$=438.3; $^1$H NMR (400 MHz, CHLOROFORM-d) δ 7.36-7.28 (m, 1H), 7.02-6.93 (m, 1H), 6.90 (ddd, J=12.0, 8.3, 2.5 Hz, 1H), 3.72 (dd, J=13.1, 2.8 Hz, 1H), 2.87 (dd, J=14.3, 2.8 Hz, 1H), 2.28 (s, 3H), 2.25 (d, J=13.6 Hz, 1H), 2.20 (s, 3H), 1.76 (s, 3H), 1.53 (s, 9H).

Preparation 66

5-((4S,6S)-2-(tert-butoxycarbonylamino)-6-(3,5-dimethylisoxazol-4-yl)-4-methyl-5,6-dihydro-4H-1,3-thiazin-4-yl)-2,4-difluorophenylboronic acid

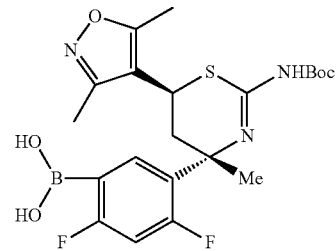 [SMILES: Cc1noc(C)c1[C@@H]1C[C@@](C)(c2cc(B(O)O)c(F)cc2F)N=C(NC(=O)OC(C)(C)C)S1]

To a solution of tert-butyl ((4S,6S)-4-(5-bromo-2,4-difluorophenyl)-6-(3,5-dimethylisoxazol-4-yl)-4-methyl-5,6-dihydro-4H-1,3-thiazin-2-yl)carbamate (Preparation 40, 100 mg, 0.194 mmol) and triisopropyl borate (1124 μL, 4.84 mmol) in THF (17 mL) at −78° C. was added a solution of n-butyllithium (232 μL, 0.581 mmol) in THF (1760 μL) dropwise over 1 min. The resulting mixture was stirred at −78° C. for 5 min., and the mixture was then quenched by the addition of HCl (129 μL, 0.387 mmol). The resulting mixture was allowed to come to rt and stir for 30 min. The reaction mixture was then diluted with water (30 mL) and extracted with EtOAc (3×20 mL). The combined extracts were washed with brine (10 mL), dried over MgSO₄, filtered and concentrated in vacuo to give the crude oil. Purification by flash chromatography (Silica, MeOH/CHCl3) gave 5-((4S,6S)-2-(tert-butoxycarbonylamino)-6-(3,5-dimethylisoxazol-4-yl)-4-methyl-5,6-dihydro-4H-1,3-thiazin-4-yl)-2,4-difluorophenylboronic acid (41 mg, 0.081 mmol, 41.8% yield) as a white, crystalline solid; MS (M+H)⁺: 482.1.

Preparation 67 tert-butyl (4S,6S)-4-(2,4-difluoro-5-(2-fluoropyrimidin-5-yl)phenyl)-6-(3,5-dimethylisoxazol-4-yl)-4-methyl-5,6-dihydro-4H-1,3-thiazin-2-ylcarbamate

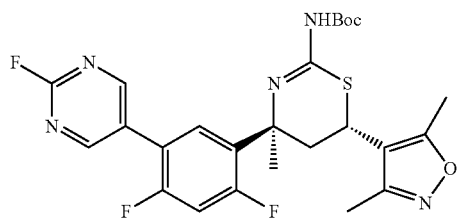 [SMILES: Cc1noc(C)c1[C@@H]1C[C@@](C)(c2cc(-c3cnc(F)nc3)c(F)cc2F)N=C(NC(=O)OC(C)(C)C)S1]

To a solution of (5-((4S,6S)-2-((tert-butoxycarbonyl)amino)-6-(3,5-dimethylisoxazol-4-yl)-4-methyl-5,6-dihydro-4H-1,3-thiazin-4-yl)-2,4-difluorophenyl)boronic acid (Preparation 66, 30 mg, 0.062 mmol) and 5-bromo-2-fluoropyrimidine (22.06 mg, 0.125 mmol) in DME (1,2-dimethoxy ethane) (283 μL), EtOH (142 μL), and H2O (142 μL) was added Bis(triphenylphosphine)palladium(II) chloride (8.75 mg, 0.012 mmol) and cesium carbonate (40.6 mg, 0.125 mmol). The resulting mixture was brought to 90° C. in a sealed tube and stirred for 10 min. The reaction mixture was then diluted with EtOAc (5 mL), washed with water (2 mL), brine (2 mL), dried over MgSO₄, filtered and concentrated in vacuo to give tert-butyl (4S,6S)-4-(2,4-difluoro-5-(2-fluoropyrimidin-5-yl)phenyl)-6-(3,5-dimethylisoxazol-4-yl)-4-methyl-5,6-dihydro-4H-1,3-thiazin-2-ylcarbamate as the crude oil which was used without further purification; MS (M+H)⁺: 534.2.

Preparation 68 tert-butyl (4S,6S)-4-(5-acetyl-2,4-difluorophenyl)-6-(3,5-dimethylisoxazol-4-yl)-4-methyl-5,6-dihydro-4H-1,3-thiazin-2-ylcarbamate

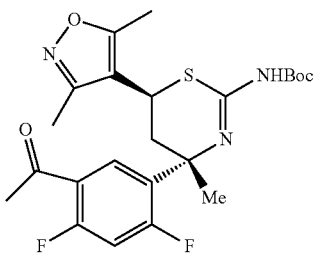 [SMILES: CC(=O)c1cc([C@]2(C)C[C@@H](c3c(C)noc3C)SC(NC(=O)OC(C)(C)C)=N2)c(F)cc1F]

To a solution of tert-butyl ((4S,6S)-4-(5-bromo-2,4-difluorophenyl)-6-(3,5-dimethylisoxazol-4-yl)-4-methyl-5,6-dihydro-4H-1,3-thiazin-2-yl)carbamate (Preparation 40, 100 mg, 0.194 mmol) and N-Methoxy-N-methylacetamide (412 μL, 3.87 mmol) in THF (17 mL) at −78° C. was added n-butyllithium (930 μL, 2.324 mmol) in THF (1760 μL) dropwise over 3 min. The resulting mixture was stirred for 5 min. at −78° C. and the cold mixture was then quenched by the addition of saturated aqueous ammonium chloride (30 mL). After coming to rt, the mixture was extracted with EtOAc (3×10 mL). The combined extracts were washed with brine (10 mL), dried over MgSO₄, filtered and concentrated in vacuo. Purification by flash chromatography (Silica, EtOAc/Hexanes) gave tert-butyl (4S,6S)-4-(5-acetyl-2,4-difluorophenyl)-6-(3,5-dimethylisoxazol-4-yl)-4-methyl-5,6-dihydro-4H-1,3-thiazin-2-ylcarbamate (50 mg, 0.099 mmol, 51.2% yield); LC-MS (M+H)⁺=480.2; ¹H NMR (500 MHz, CHLOROFORM-d) δ 7.87 (t, J=8.6 Hz, 1H), 6.98 (t, J=10.6 Hz, 1H), 3.77 (br. s., 1H), 3.74-3.70 (m, 1H), 2.90 (d, J=13.7 Hz, 1H), 2.73-2.57 (m, 4H), 2.36-2.29 (m, 3H), 2.27 (d, J=11.3 Hz, 1H), 2.24-2.16 (m, 4H), 1.76 (br. s., 3H), 1.55 (s, 9H).

Preparation 69 tert-butyl (4S,6S)-4-(2,4-difluorophenyl)-6-(5-(2-hydroxy-2-methylpropyl)-3-methylisoxazol-4-yl)-4-methyl-5,6-dihydro-4H-1,3-thiazin-2-ylcarbamate

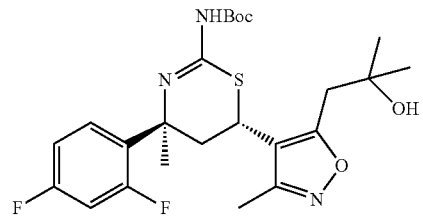 [SMILES: Cc1noc(CC(C)(C)O)c1[C@@H]1C[C@@](C)(c2ccc(F)cc2F)N=C(NC(=O)OC(C)(C)C)S1]

To a solution of tert-butyl ((4S,6S)-4-(5-bromo-2,4-difluorophenyl)-6-(3,5-dimethylisoxazol-4-yl)-4-methyl-5,6-dihydro-4H-1,3-thiazin-2-yl)carbamate (Preparation 40, 100 mg, 0.194 mmol) and propan-2-one (313 μL, 3.87 mmol) in THF (1.76E+04 μL) at −78° C. was added n-butyllithium (775 μL, 1.936 mmol) in THF (1760 μL) dropwise over 2 min. The resulting mixture was stirred at −78° C. for 5 min.

and the cold mixture was then quenched by the addition of saturated aqueous ammonium chloride (50 mL). The resulting mixture was allowed to come to rt at which time it was extracted with EtOAc (3×20 mL). The combined extracts were washed with brine (20 mL), dried over MgSO₄, filtered and concentrated in vacuo. Purification by flash chromatography (Silica, EtOAc/Hexanes) gave a mixture containing approx. a 1:3 ratio of tert-butyl (4S,6S)-4-(2,4-difluorophenyl)-6-(5-(2-hydroxy-2-methylpropyl)-3-methylisoxazol-4-yl)-4-methyl-5,6-dihydro-4H-1,3-thiazin-2-ylcarbamate and tert-butyl ((4S,6S)-4-(2,4-difluoro-5-(2-hydroxypropan-2-yl)phenyl)-6-(3,5-dimethylisoxazol-4-yl)-4-methyl-5,6-dihydro-4H-1,3-thiazin-2-yl)carbamate (49 mg, 0.084 mmol, 43.4% combined yield); MS (M+H)⁺: 496.2.

Preparation 70

5-bromo-2-methylpyrimidine

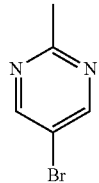

A solution of 5-bromo-2-iodopyrimidine (400 mg, 1.404 mmol), Me₃Al (2 M in toluene, 1053 μL, 2.106 mmol) and tetrakistriphenylphosphinepalladium(0) (32.5 mg, 0.028 mmol) in dioxane (4680 μL) was heated at 110° C. for 12 h. Water was added and the aqueous layer was extracted with EtOAc (×3). The combined organic layers were washed with brine, dried over anhydrous sodium sulfate, and filtered, and the filtrate was evaporated in vacuo to give 5-bromo-2-methylpyrimidine (88 mg, 0.509 mmol, 36.2% yield) as a brown solid. ¹H NMR (500 MHz, CHLOROFORM-d) δ 8.70 (s, 2H), 2.71 (s, 3H). MS (M+H)⁺: 174.91.

Preparation 71 tert-butyl ((4S,6S)-4-(2,4-difluoro-5-(2-methylpyrimidin-5-yl)phenyl)-6-(3,5-dimethylisoxazol-4-yl)-4-methyl-5,6-dihydro-4H-1,3-thiazin-2-yl)carbamate

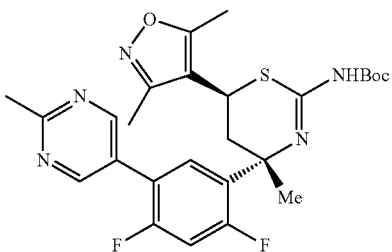 [SMILES: Cc1ncc(-c2cc([C@]3(C)C[C@@H](c4c(C)noc4C)SC(NC(=O)OC(C)(C)C)=N3)c(F)cc2F)cn1]

A solution of 5-bromo-2-methylpyrimidine (43.1 mg, 0.249 mmol), (5-((4S,6S)-2-((tert-butoxycarbonyl)amino)-6-(3,5-dimethylisoxazol-4-yl)-4-methyl-5,6-dihydro-4H-1,3-thiazin-4-yl)-2,4-difluorophenyl)boronic acid (Preparation 66, 30 mg, 0.062 mmol), PdCl₂(P(Ph₃)₂ (8.75 mg, 0.012 mmol) and cesium carbonate (81 mg, 0.249 mmol) in DME (312 μL), EtOH (156 μL), H₂O (156 μL) was heated at 100° C. for 6 min. The crude product was purified by reverse phase preparative HPLC on a Luna C18 column (10 μM, 30×100 mm) eluting with 0-100% B (A: 95% eater/5% MeCN/10 nM NH₄OAc, B: 5% water/95% MeCN/10 mM NH₄OAc) over 12 min to give tert-butyl ((4S,6S)-4-(2,4-difluoro-5-(2-methylpyrimidin-5-yl)phenyl)-6-(3,5-dimethylisoxazol-4-yl)-4-methyl-5,6-dihydro-4H-1,3-thiazin-2-yl)carbamate (11 mg, 0.021 mmol, 33.3% yield) as a white solid. ¹H NMR (500 MHz, CHLOROFORM-d) δ 8.82 (br. s., 2H), 7.36 (t, J=8.5 Hz, 1H), 7.13-7.03 (m, 1H), 3.82-3.71 (m, 1H), 2.93 (d, J=11.9 Hz, 1H), 2.84 (s, 3H), 2.32 (s, 3H), 2.24 (2H, d, J=11.9 Hz), 2.23 (s, 4H), 1.78 (s, 3H), 1.53 (s, 9H). MS (M+Na)⁺: 552.39.

Preparation 72

1-(1-methyl-1H-pyrazol-5-yl)ethanone

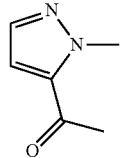

Iodomethane (4.68 mL, 74.8 mmol) was added to a stirred mixture of 1-(1H-pyrazol-5-yl)ethanone (8.24 g, 74.8 mmol) and potassium carbonate (20.58 g, 149 mmol) in acetonitrile (50 mL). The mixture was left to stir at rt for 3 days. Water was added to the reaction mixture, and the mixture was extracted with ethyl acetate. The combined organic layers were washed with brine, dried over magnesium sulfate, filtered and concentrated in vacuo. The crude product was purified using silica gel column chromatography (5:1-2:1 hexane/ethyl acetate, linear gradient) to afford 1-(1-methyl-1H-pyrazol-5-yl)ethanone (1.20 g, 9.67 mmol, 13% yield) (less polar component, first to elute) and 1-(1-methyl-1H-pyrazol-3-yl)ethanone (5.40 g, 43.5 mmol, 58% yield) (more polar component, second to elute). Data for 1-(1-methyl-1H-pyrazol-5-yl)ethanone: ¹H NMR (500 MHz, CHLOROFORM-d) δ 7.47 (d, J=2.0 Hz, 1H), 6.83 (d, J=2.1 Hz, 1H), 4.17 (s, 3H), 2.52 (s, 3H). MS (M+H)⁺: 125.2. Data for 1-(1-methyl-1H-pyrazol-3-yl)ethanone: ¹H NMR (500 MHz, chloroform-d) δ 7.38 (d, J=2.3 Hz, 1H), 6.78 (d, J=2.4 Hz, 1H), 3.98 (s, 3H), 2.57 (s, 3H). MS (M+H)⁺: 125.2.

Preparation 73

(R,E)-N-(1-(2,4-difluorophenyl)ethylidene)-2-methylpropane-2-sulfinamide

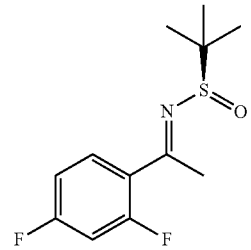

To a solution of 1-(2,4-difluorophenyl)ethanone (12 g, 77 mmol) and (R)-2-methylpropane-2-sulfinamide (10.25 g, 85 mmol) in THF (200 mL) was added ethyl orthotitanate (24 mL, 115 mmol), and the reaction mixture was heated at 65° C. for 16 h. The solution was allowed to cool to rt and brine was added. The resulting suspension was filtered through a pad of Celite. The filter cake was washed with EtOAc, and the combined organic layer was separated, dried over sodium sulfate, filtered, and concentrated. The crude product was purified by silica gel chromatography eluting with 10-25% EtOAc/Hexanes to give the title compound as a yellow oil (11.7 g, 59% yield). $^1$H NMR (400 MHz, CHLOROFORM-d) δ 7.75 (t, J=7.0 Hz, 1H), 7.00-6.80 (m, 2H), 2.77 (d, J=3.5 Hz, 3H), 1.42-1.25 (m, 9H).

Preparation 74

(R)—N—((S)-2-(2,4-difluorophenyl)-4-(1-methyl-1H-pyrazol-5-yl)-4-oxobutan-2-yl)-2-methylpropane-2-sulfinamide

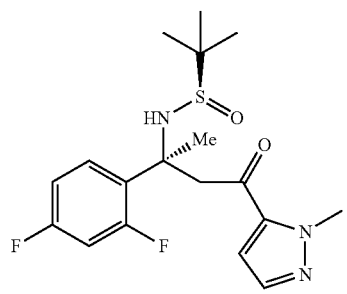 [SMILES: Cn1nccc1C(=O)C[C@](C)(N[S@](=O)C(C)(C)C)c1ccc(F)cc1F]

A solution of 2.4 M n-butyllithium in hexane (1.933 mL, 4.83 mmol) was added to a solution of 1-(1-methyl-1H-pyrazol-5-yl)ethanone (600 mg, 4.83 mmol) in THF (20 mL) maintained at −78° C. under a nitrogen atmosphere. The resulting mixture was allowed to stir for 20 min at −78° C. A solution of (R,E)-N-(1-(2,4-difluorophenyl)ethylidene)-2-methylpropane-2-sulfinamide (preparation 73, 836 mg, 3.22 mmol) in THF (5 mL) was slowly added over 2 min. After 5 min, the resulting solution was warmed to between −30 and −20° C. and allowed to stir for 24 h. The reaction was quenched with saturated aqueous ammonium chloride solution and extracted with EtOAc. The combined organics were washed with brine, dried over magnesium sulfate, and filtered. The filtrate was concentrated in vacuo. The crude product was purified using silica gel column chromatography (5:1-1:1 hexanes/ethyl acetate, linear gradient) to afford (R)—N—((S)-2-(2,4-difluorophenyl)-4-(1-methyl-1H-pyrazol-5-yl)-4-oxobutan-2-yl)-2-methylpropane-2-sulfinamide (330 mg, 0.861 mmol, 27% yield). MS (M+Na)$^+$: 406.1.

Preparation 75

(R)—N-((2S,4R)-2-(2,4-difluorophenyl)-4-hydroxy-4-(1-methyl-1H-pyrazol-5-yl)butan-2-yl)-2-methylpropane-2-sulfinamide

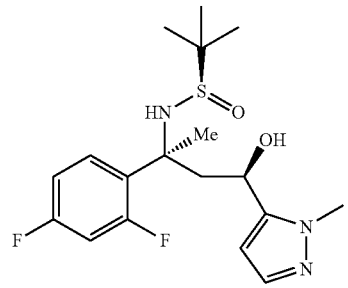 [SMILES: Cn1nccc1[C@H](O)C[C@](C)(N[S@](=O)C(C)(C)C)c1ccc(F)cc1F]

To a solution of (R)—N—((S)-2-(2,4-difluorophenyl)-4-(1-methyl-1H-pyrazol-5-yl)-4-oxobutan-2-yl)-2-methylpropane-2-sulfinamide (330 mg, 0.86 mmol) in diethyl ether (100 mL) at −78° C. was added lithium tri-tert-butoxyaluminium hydride (1.10 mL, 1.10 mmol) dropwise. When the addition was complete, the resulting mixture was stirred at −78° C. for 10 min, then the mixture was allowed to warm to −25° C. and stir for 30 min. Approximately 4 g of sodium sulfate decahydrate was then added to the reaction mixture along with diethyl ether (100 mL). The reaction mixture was allowed to come to rt and was then stirred vigorously for 24 h. Anhydrous magnesium sulfate was added and the resulting mixture was stirred for 1 h. The reaction mixture was filtered through Celite and concentrated in vacuo to afford (R)—N-((2S,4R)-2-(2,4-difluorophenyl)-4-hydroxy-4-(1-methyl-1H-pyrazol-5-yl)butan-2-yl)-2-methylpropane-2-sulfinamide (330 mg, 0.856 mmol, 99% yield) as a white foamy solid. MS (M+H)$^+$: 386.1.

Preparation 76

(1R,3S)-3-amino-3-(2,4-difluorophenyl)-1-(1-methyl-1H-pyrazol-5-yl)butan-1-ol

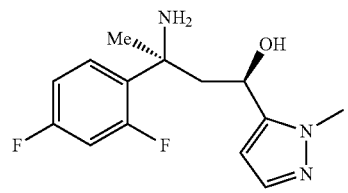 [SMILES: Cn1nccc1[C@H](O)C[C@](C)(N)c1ccc(F)cc1F]

To a solution of (R)—N-((2S,4R)-2-(2,4-difluorophenyl)-4-hydroxy-4-(1-methyl-1H-pyrazol-5-yl)butan-2-yl)-2-methylpropane-2-sulfinamide (0.330 g, 0.860 mmol) in methanol (20 ml) was added 4 M HCl in dioxane (2.1 ml, 8.6 mmol). The resulting mixture was stirred at rt for 30 min. The reaction mixture was then concentrated in vacuo to afford the hydrochloride salt of (1R,3S)-3-amino-3-(2,4-difluorophenyl)-1-(1-methyl-1H-pyrazol-5-yl)butan-1-ol in quantitative yield. MS (M+H)$^+$: 282.1.

Preparation 77

N-((2S,4R)-2-(2,4-difluorophenyl)-4-hydroxy-4-(1-methyl-1H-pyrazol-5-yl)butan-2-ylcarbamothioyl)benzamide

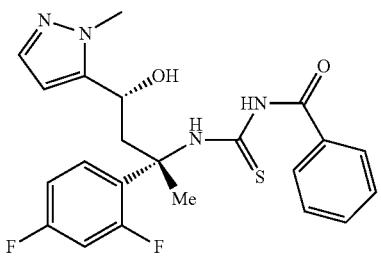 [SMILES: Cn1nccc1[C@H](O)C[C@](C)(NC(=S)NC(=O)c1ccccc1)c1ccc(F)cc1F]

To a solution of (1R,3S)-3-amino-3-(2,4-difluorophenyl)-1-(1-methyl-1H-pyrazol-5-yl)butan-1-ol, HCl (272 mg, 0.856 mmol) in DCM (25 mL) at rt was added DIEA (0.299 mL, 1.71 mmol) and benzoyl isothiocyanate (0.230 mL, 1.71 mmol). The reaction mixture was stirred at rt for 1 h. The reaction was quenched by the addition of 0.5 N HCl (20 mL). The resulting mixture was extracted with DCM. The combined organics were washed with brine, dried over sodium sulfate, filtered, and concentrated in vacuo. The residue was purified by silica gel column chromatography (16-75% EtOAc/Hexanes, linear gradient) to afford N-(((2S,4R)-2-(2,4-difluorophenyl)-4-hydroxy-4-(1-methyl-1H-pyrazol-5-yl)butan-2-yl)carbamothioyl)benzamide (268 mg, 0.603 mmol, 70% yield). $^1$H NMR (500 MHz, chloroform-d) δ 11.71 (s, 1H), 8.82 (s, 1H), 7.89-7.78 (m, 2H), 7.62 (tt, J=7.5, 1.2 Hz, 1H), 7.55-7.48 (m, 2H), 7.40 (td, J=9.1, 6.3 Hz, 1H), 7.35 (d, J=2.0 Hz, 1H), 6.94-6.85 (m, 1H), 6.83-6.73 (m, 1H), 6.19 (d, J=1.8 Hz, 1H), 5.07 (d, J=9.3 Hz, 1H), 3.88 (s, 3H), 3.03 (dd, J=14.8, 9.9 Hz, 1H), 2.69 (d, J=4.6 Hz, 1H), 2.32 (dd, J=14.7, 2.5 Hz, 1H), 2.21 (s, 3H). MS (M+H)$^+$: 558.1.

Preparation 78

N-methoxy-N,3-dimethylisoxazole-4-carboxamide

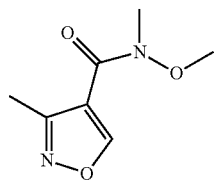

A solution of 3-methylisoxazole-4-carboxylic acid (5.00 g, 39.3 mmol), N,O-dimethylhydroxylamine hydrochloride (4.22 g, 43.3 mmol), HATU (16.5 g, 43.3 mmol) and DIEA (17.18 ml, 98 mmol) in DCM (112 ml) was stirred at rt for 16 h. Water was added and the aqueous layer was extracted with DCM (×3). The combined organic layers were washed with brine, dried over anhydrous sodium sulfate, filtered, and concentrated in vacuo to give the crude product. The crude product was purified by silica gel chromatography (0-60% EtOAc/Hexane, linear gradient) to give N-methoxy-N,3-dimethylisoxazole-4-carboxamide (6.0 mmol, 35.3 mmol, 90% yield) as a colorless oil. $^1$H NMR (500 MHz, chloroform-d) δ 8.85 (s, 1H), 3.70 (s, 3H), 3.34 (s, 3H), 2.54 (s, 3H). MS (M+H)$^+$: 171.1.

Preparation 79

1-(3-methylisoxazol-4-yl)ethanone

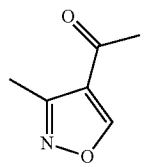

To a solution of N-methoxy-N,3-dimethylisoxazole-4-carboxamide (6.00 g, 35.3 mmol) in THF (118 ml) at 0° C. was added a solution of 3.0 M methylmagnesium bromide in THF (23.5 ml, 70.5 mmol) dropwise via pressure equalizing addition funnel. The reaction mixture was stirred at 0° C. for 3 h and then at rt for 10 h. A 1 M aqueous solution of hydrochloric acid (35.3 ml, 35.3 mmol) was added dropwise. The resulting mixture was extracted with EtOAc. The combined organic layers were washed with brine, dried over anhydrous sodium sulfate, filtered, and concentrated in vacuo to give 1-(3-methylisoxazol-4-yl)ethanone (2.83 g, 22.6 mmol, 64% yield). $^1$H NMR (500 MHz, chloroform-d) δ 8.85 (s, 1H), 2.52 (s, 3H), 2.49 (s, 3H). MS (M+H)$^+$: 126.2.

Preparation 80

(R)—N—((S)-2-(2,4-difluorophenyl)-4-(3-methylisoxazol-4-yl)-4-oxobutan-2-yl)-2-methylpropane-2-sulfinamide

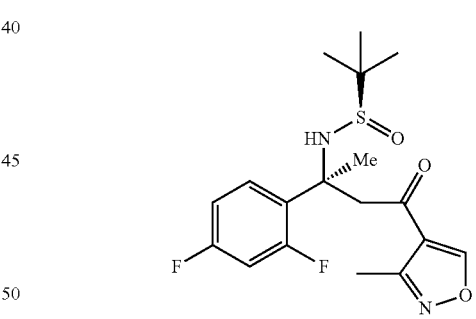

To a solution of 2.5 M n-BuLi in THF (0.96 mL, 2.40 mmol) in THF (4.0 mL) at −78° C. was added a solution of 1-(3-methylisoxazol-4-yl)ethanone (300 mg, 2.40 mmol) in THF (0.800 mL) dropwise over 2 min. The resulting mixture was stirred at −78° C. for 20 min. A solution of (R,E)-N-(1-(2,4-difluorophenyl)ethylidene)-2-methylpropane-2-sulfinamide (preparation 73, 414 mg, 1.60 mmol) in THF (0.800 mL) was then added dropwise over 2 min. The resulting mixture was stirred at −78° C. for 5 min., then allowed to warm to −30° C. and was stirred for 3 h. The cold reaction mixture was quenched by the addition of saturated aqueous ammonium chloride (25 mL). The resulting mixture was then allowed to come to rt at which time it was extracted with EtOAc. The combined extracts were sequentially washed with water, brine. The organic layer was dried over magnesium sulfate, filtered, and concentrated in vacuo to give the crude oil. This crude material was purified by flash chromatography (0-100% EtOAc/hexanes, linear gradient) to give (R)—N—((S)-2-(2,4-difluorophenyl)-4-(3-methylisoxazol-4-yl)-4-oxobutan-2-yl)-2-methylpropane-2-sulfinamide (300 mg, 0.780 mmol, 49% yield). $^1$H NMR (500 MHz, chloroform-d) δ 8.91 (s, 1H), 7.55 (td, J=9.2, 6.4 Hz, 1H), 6.96-6.84 (m, 1H), 6.74 (ddd, J=12.8, 8.5, 2.6 Hz, 1H), 3.92 (dd, J=17.8, 1.3 Hz, 1H), 3.64 (dd, J=17.9, 2.3 Hz, 1H), 2.39 (s, 3H), 1.82 (s, 3H), 1.32 (s, 9H). MS (M+H)$^+$: 385.1.

Preparation 81

(R)—N-((2S,4R)-2-(2,4-difluorophenyl)-4-hydroxy-4-(3-methylisoxazol-4-yl)butan-2-yl)-2-methylpropane-2-sulfinamide

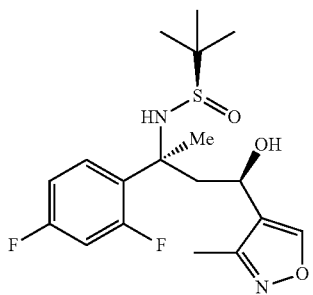 [SMILES: Cc1nocc1[C@H](O)C[C@](C)(N[S@](=O)C(C)(C)C)c1ccc(F)cc1F]

To a solution of (R)—N—((S)-2-(2,4-difluorophenyl)-4-(3-methylisoxazol-4-yl)-4-oxobutan-2-yl)-2-methylpropane-2-sulfinamide (300 mg, 0.780 mmol) in diethyl ether (3.9 mL) at −78° C. was added a solution of 1 M lithium tri-tert-butoxyaluminium hydride in THF (3.12 mL, 3.12 mmol) dropwise. When the addition was complete, the resulting mixture was stirred at −78° C. for 10 min, then the mixture was allowed to come to −25° C. and stir for 30 min. Several crystals of sodium sulfate decahydrate were then added to the reaction mixture along with diethyl ether (25 mL). The reaction mixture was allowed to come to rt and stir vigorously for 2 h. Saturated aqueous ammonium chloride (5 mL) was then added to the reaction mixture which was then filtered through Celite, washing the solid with EtOAc. The layers of the filtrate were separated and the aqueous layer was extracted with EtOAc (2×2 mL). The combined organics were washed with brine (5 mL), dried over sodium sulfate, filtered and concentrated in vacuo to give (R)—N-((2S,4R)-2-(2,4-difluorophenyl)-4-hydroxy-4-(3-methylisoxazol-4-yl)butan-2-yl)-2-methylpropane-2-sulfinamide (267 mg, 0.691 mmol, 89% yield). MS (M+H)$^+$: 387.1.

Preparation 82

(1R,3S)-3-amino-3-(2,4-difluorophenyl)-1-(3-methylisoxazol-4-yl)butan-1-ol

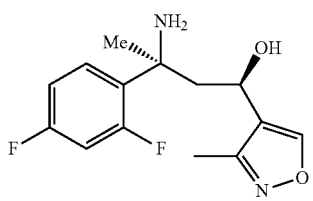 [SMILES: Cc1nocc1[C@H](O)C[C@](C)(N)c1ccc(F)cc1F]

To a solution of (R)—N-((2S,4R)-2-(2,4-difluorophenyl)-4-hydroxy-4-(3-methylisoxazol-4-yl)butan-2-yl)-2-methylpropane-2-sulfinamide (128 mg, 0.331 mmol) in methanol (12 mL) was added 4 M HCl in dioxane (0.83 mL, 3.3 mmol). The resulting mixture was stirred at rt for 1 h. The reaction mixture was then concentrated in vacuo to give a crude oil. This crude material was purified by flash chromatography (0-25% methanol/dichloromethane, with 2.5% NH$_4$OH in the methanol) to give (1R,3S)-3-amino-3-(2,4-difluorophenyl)-1-(3-methylisoxazol-4-yl)butan-1-ol (90 mg, 0.319 mmol, 96% yield) as a clear viscous oil. MS (M+H)$^+$: 283.1.

Preparation 83

N-((2S,4R)-2-(2,4-difluorophenyl)-4-hydroxy-4-(3-methylisoxazol-4-yl)butan-2-ylcarbamothioyl)benzamide

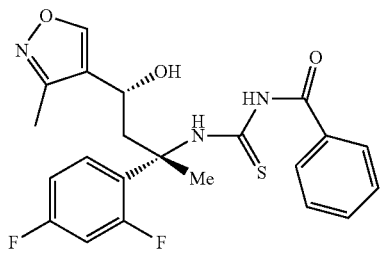 [SMILES: Cc1nocc1[C@H](O)C[C@](C)(NC(=S)NC(=O)c1ccccc1)c1ccc(F)cc1F]

To a solution of (1R,3S)-3-amino-3-(2,4-difluorophenyl)-1-(3-methylisoxazol-4-yl)butan-1-ol (90 mg, 0.319 mmol) in DCM (5 mL) at rt was added benzoyl isothiocyanate (0.064 mL, 0.478 mmol) and the reaction mixture was stirred at rt for 30 min. The solvent was removed in vacuo and the residue was purified by silica gel column chromatography (10-80% EtOAc/hexanes, linear gradient) to afford N-(((2S,4R)-2-(2,4-difluorophenyl)-4-hydroxy-4-(3-methylisoxazol-4-yl)butan-2-yl)carbamothioyl)benzamide (40 mg, 0.090 mmol, 28% yield). MS (M+H)$^+$: 446.1.

Preparation 84

(R)—N—((S)-2-(2,4-difluorophenyl)-4-oxo-4-(pyrimidin-5-yl)butan-2-yl)-2-methylpropane-2-sulfinamide

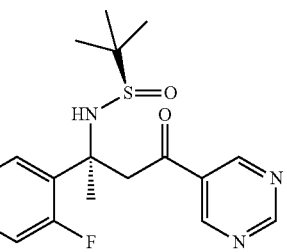

To a solution of 1-(pyrimidin-5-yl)ethanone (2.072 g, 16.97 mmol) in DMF (40 mL) was added 60% wt NaH (0.747 g, 18.66 mmol) at 0° C. under nitrogen. The mixture was stirred at 0° C. for 30 min. A solution of (R,E)-N-(1-(2,4-difluorophenyl)ethylidene)-2-methylpropane-2-sulfinamide from preparation 73 (2.2 g, 8.48 mmol) in DMF (4 mL) was slowly added at −10° C. under nitrogen. The mixture was stirred from −10° C. to −5° C. over 1.5 h. The reaction was quenched with water, and extracted with 2×250 mL of ethyl acetate. The combined organic layers were removed, dried over sodium sulfate, and concentrated. The residue was purified via silica gel chromatography (gradient elution using ethyl acetate to 10% methanol in ethyl acetate) to give (R)—N—((S)-2-(2,4-difluorophenyl)-4-oxo-4-(pyrimidin-5-yl)butan-2-yl)-2-methylpropane-2-sulfinamide (1.5 g, 3.93 mmol, 46.4% yield). MS (M+H)$^+$=382.05. $^1$H NMR (500 MHz, CHLOROFORM-d) δ 9.37 (s, 1H), 9.18 (s, 2H), 7.61 (td, J=9.3, 6.5 Hz, 1H), 6.97-6.89 (m, 1H), 6.74 (ddd, J=12.9, 8.4, 2.6 Hz, 1H), 5.32 (s, 1H), 4.21 (dd, J=18.6, 1.4 Hz, 1H), 3.91 (dd, J=18.6, 2.9 Hz, 1H), 1.86 (s, 3H), 1.34 (s, 9H).

Preparation 85

(R)—N-((2S,4R)-2-(2,4-difluorophenyl)-4-hydroxy-4-(pyrimidin-5-yl)butan-2-yl)-2-methylpropane-2-sulfinamide

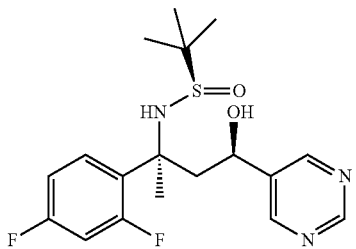 [SMILES: CC(C)(C)[S@@](=O)N[C@@](C)(C[C@@H](O)c1cncnc1)c1ccc(F)cc1F]

To a solution of (R)—N—((S)-2-(2,4-difluorophenyl)-4-oxo-4-(pyrimidin-5-yl)butan-2-yl)-2-methylpropane-2-sulfinamide (2.0 g, 5.24 mmol) in diethyl ether (25 mL) was added 1.0 M lithium tri-tert-butoxyaluminium hydride solution in THF (10.49 mL, 10.49 mmol) at −78° C. under nitrogen. The mixture was stirred from −78° C. to −50° C. for 1 h. The rxn was quenched with Na2SO4 decahydrate and 300 mL of EtOAc was added. After stirring at rt for 2 h, the solid was filtered out. The filtrate was washed with water, dried over anhydrous Na2SO4, and concentrated. The residue was crystallized in EtOAc/Hexanes to give 1.2 g of product. The mother liquor was concentrated and purified via silica gel chromatography (hexanes-100% EtOAc-10% methanol in ethyl acetate) to give 0.3 g of additional product. The combined yield was 1.5 g (3.91 mmol, 74.6% yield) of the desired ((R)—N-((2S,4R)-2-(2,4-difluorophenyl)-4-hydroxy-4-(pyrimidin-5-yl)butan-2-yl)-2-methylpropane-2-sulfinamide. (M+H)$^+$=384. $^1$H NMR (500 MHz, CHLOROFORM-d) δ 9.04 (s, 1H), 8.70 (s, 2H), 7.42 (td, J=9.0, 6.5 Hz, 1H), 6.86-6.77 (m, J=16.3, 2.3, 0.6 Hz, 1H), 6.75-6.68 (m, 1H), 6.66 (br. s., 1H), 6.14 (s, 1H), 5.24 (d, J=10.5 Hz, 1H), 2.65 (dd, J=14.8, 10.8 Hz, 1H), 2.11 (s, 3H), 1.90 (dd, J=14.8, 2.3 Hz, 1H), 1.21 (s, 9H).

Preparation 86

(1R,3S)-3-amino-3-(2,4-difluorophenyl)-1-(pyrimidin-5-yl)butan-1-ol, hydrochloride salt

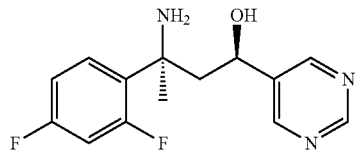 [SMILES: C[C@](N)(C[C@@H](O)c1cncnc1)c1ccc(F)cc1F]

To a solution of (R)—N-((2S,4R)-2-(2,4-difluorophenyl)-4-hydroxy-4-(pyrimidin-5-yl)butan-2-yl)-2-methylpropane-2-sulfinamide (1.5 g, 3.91 mmol) in methanol (20 mL) was added at 0° C. 10 mL of a 4 M solution of HCl in dioxane. The mixture was stirred from 0° C. to rt over 1 h. The mixture was directly concentrated and dried azeotropically with toluene to give a crude (1R,3S)-3-amino-3-(2,4-difluorophenyl)-1-(pyrimidin-5-yl)butan-1-ol hydrochloride (1.235 g, 3.91 mmol, 100% yield), which was used for the next step without any purification. MS (M+H)$^+$=280.05.

Preparation 87

N-(((2S,4R)-2-(2,4-difluorophenyl)-4-hydroxy-4-(pyrimidin-5-yl)butan-2-yl)carbamothioyl)benzamide

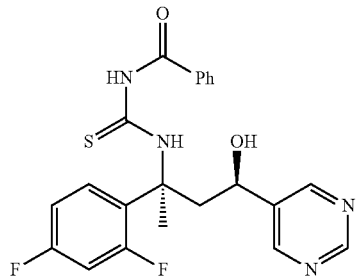 [SMILES: C[C@@](C[C@@H](O)c1cncnc1)(NC(=S)NC(=O)c1ccccc1)c1ccc(F)cc1F]

To a solution of the crude (1R,3S)-3-amino-3-(2,4-difluorophenyl)-1-(pyrimidin-5-yl)butan-1-ol hydrochloride (1.231 g, 3.9 mmol) in DCM (25 mL) was added DIEA (2.043 mL, 11.70 mmol) followed by benzoyl isothiocyanate (0.764 g, 4.68 mmol) at 0° C. under nitrogen. The mixture was stirred at 0° C. for 30 min, then at rt for 1.5 h. The mixture was directly concentrated and the residue was purified via silica gel chromatography eluting with a linear gradient of hexanes to 100% ethyl acetate to give N-(((2S,4R)-2-(2,4-difluorophenyl)-4-hydroxy-4-(pyrimidin-5-yl)butan-2-yl)carbamothioyl)benzamide (1.0 g, 2.260 mmol, 57.9% yield). (M+H)$^+$=443.1. $^1$H NMR (500 MHz, CHLOROFORM-d) δ 11.73 (s, 1H), 9.16 (s, 1H), 8.83 (s, 1H), 8.77 (s, 2H), 7.92-7.83 (m, 2H), 7.65 (td, J=7.6, 1.5 Hz, 1H), 7.57-7.51 (m, 2H), 7.42 (td, J=9.1, 6.3 Hz, 1H), 6.93-6.87 (m, 1H), 6.79 (ddd, J=12.3, 8.7, 2.7 Hz, 1H), 5.10 (d, J=9.8 Hz, 1H), 3.01 (dd, J=14.8, 9.6 Hz, 1H), 2.70 (d, J=3.2 Hz, 1H), 2.29 (d, J=2.4 Hz, 1H), 2.26 (s, 3H).

EXAMPLES

The following examples set forth certain specific aspects of the invention, but should not be construed as limiting the scope thereof:

Example 1

(±)-4-(2,4-difluoro-5-(pyrimidin-5-yl)phenyl)-6-(3,4-dimethoxyphenyl)-5,6-dihydro-4H-1,3-thiazin-2-amine

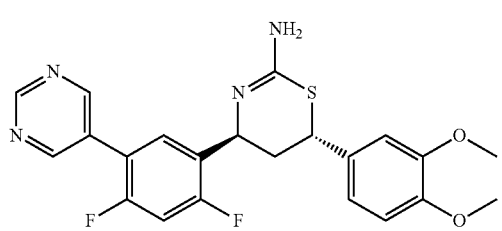 [SMILES: COc1ccc([C@@H]2C[C@@H](c3cc(-c4cncnc4)c(F)cc3F)N=C(N)S2)cc1OC]

Diastereomer B

To a solution of 2,4-difluoro-5-(pyrimidin-5-yl)benzaldehyde (Preparation 3)(100 mg, 0.454 mmol) in DMF (454 μL) was added thiourea (41.5 mg, 0.545 mmol), 3,4-dimethoxystyrene (67.2 μL, 0.454 mmol), and chlorotrimethylsilane (58.1 μL, 0.454 mmol). The resulting mixture was brought to 120° C. and stirred for 1 h. The mixture was then diluted with chloroform (10 mL, a precipitate formed) and filtered. The filtrate was concentrated and purified by flash chromatography (silica, MeOH/CHCl3) to give a yellow oil consisting primarily of 2 peaks with the desired MW by LC/MS. This oil was further purified (diastereomer separation) by prep HPLC (C18, MeOH/Water/NH₄OAc) to give (±)-4-(2,4-difluoro-5-(pyrimidin-5-yl)phenyl)-6-(3,4-dimethoxyphenyl)-5,6-dihydro-4H-1,3-thiazin-2-amine (16.4 mg, 0.037 mmol, 8.2% yield), the first major peak to elute, as an oil; LC-MS (M+H)+=443.2; $^1$H NMR (500 MHz, DMSO-d$_6$) δ 9.26 (s, 1H), 9.01 (d, J=1.2 Hz, 2H), 7.97 (s, 1H), 7.54-7.42 (m, 2H), 7.00 (s, 1H), 6.95 (d, J=0.9 Hz, 2H), 6.12 (br. s., 2H), 4.96 (dd, J=6.3, 4.1 Hz, 1H), 4.35 (dd, J=8.2, 4.0 Hz, 1H), 3.76 (d, J=1.2 Hz, 6H), 2.91 (s, 2H), 2.75 (d, J=0.6 Hz, 1H), 2.29-2.21 (m, 1H), 2.03 (ddd, J=13.6, 6.6, 4.0 Hz, 1H), 1.87 (s, 2H).

Example 1A (4S,6S)-4-(2,4-difluoro-5-(pyrimidin-5-yl)phenyl)-6-(3,4-dimethoxyphenyl)-5,6-dihydro-4H-1,3-thiazin-2-amine

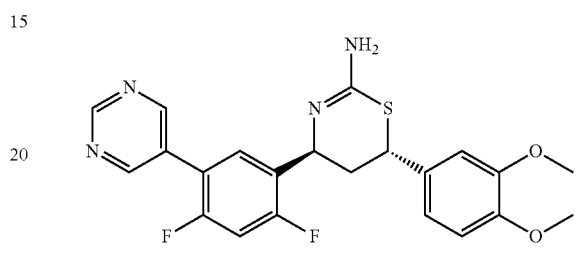

Enantiomer A of Example 1

(±)-4-(2,4-difluoro-5-(pyrimidin-5-yl)phenyl)-6-(3,4-dimethoxyphenyl)-5,6-dihydro-4H-1,3-thiazin-2-amine (Example 1) was separated by chiral SFC (C18, MeOH/Water/NH₄OAc) to give (4S,6S)-4-(2,4-difluoro-5-(pyrimidin-5-yl)phenyl)-6-(3,4-dimethoxyphenyl)-5,6-dihydro-4H-1,3-thiazin-2-amine (first to elute, enantiomer A) as an opaque glass; LC-MS (M+H)+=443.1; $^1$H NMR (400 MHz, MeOH-d$_4$) δ 9.18 (s, 1H), 9.00 (d, J=1.5 Hz, 2H), 7.48 (t, J=8.4 Hz, 1H), 7.20 (t, J=10.3 Hz, 1H), 6.98 (s, 1H), 6.93 (d, J=1.0 Hz, 2H), 5.14 (t, J=4.8 Hz, 1H), 4.25 (dd, J=9.3, 3.8 Hz, 1H), 3.82 (d, J=1.8 Hz, 6H), 2.75 (q, J=7.3 Hz, 1H), 2.39-2.17 (m, 2H).

The following compounds in Table 1 are prepared essentially according to the preparation of (±)-4-(2,4-difluoro-5-(pyrimidin-5-yl)phenyl)-6-(3,4-dimethoxyphenyl)-5,6-dihydro-4H-1,3-thiazin-2-amine (Example 1) from the appropriate commercial or other aldehydes (Preparations 4,5), alkenes, and styrenes (Preparation 6).

TABLE 1

| Example # | Structure and Chemical Name | MS (M + H)+ |
|---|---|---|
| 2 | 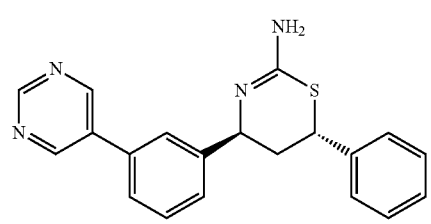 [SMILES: NC1=N[C@H](c2cccc(-c3cncnc3)c2)C[C@@H](c2ccccc2)S1]<br>(±)-6-phenyl-4-(3-(pyrimidin-5-yl)phenyl)-5,6-dihydro-4H-1,3-thiazin-2-amine | 347.0 |

TABLE 1-continued

| Example # | Structure and Chemical Name | MS (M + H)+ |
|---|---|---|
| 3 | 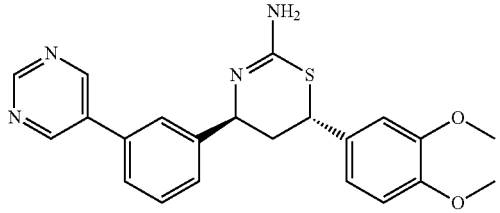 [SMILES: COc1ccc([C@@H]2C[C@@H](c3cccc(-c4cncnc4)c3)N=C(N)S2)cc1OC]<br>(±)-6-(3,4-dimethoxyphenyl)-4-(3-(pyrimidin-5-yl)phenyl)-5,6-dihydro-4H-1,3-thiazin-2-amine | 407.1 |
| 4 | 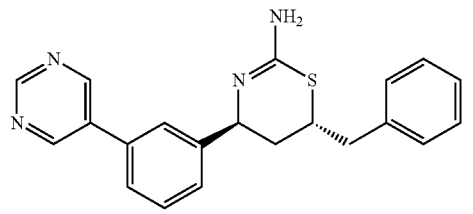 [SMILES: NC1=N[C@H](c2cccc(-c3cncnc3)c2)C[C@@H](Cc2ccccc2)S1]<br>(±)-6-benzyl-4-(3-(pyrimidin-5-yl)phenyl)-5,6-dihydro-4H-1,3-thiazin-2-amine | 361.1 |
| 5 | 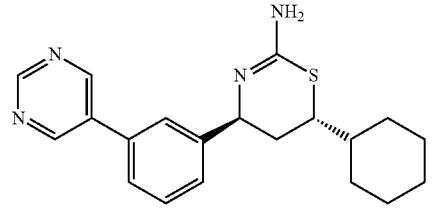 [SMILES: NC1=N[C@H](c2cccc(-c3cncnc3)c2)C[C@@H](C2CCCCC2)S1]<br>(±)-6-cyclohexyl-4-(3-(pyrimidin-5-yl)phenyl)-5,6-dihydro-4H-1,3-thiazin-2-amine | 353.1 |
| 6 | 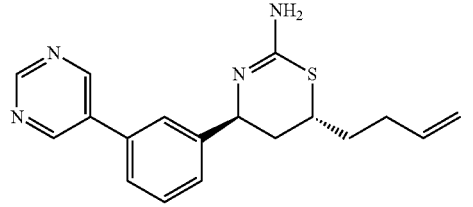 [SMILES: C=CCC[C@@H]1C[C@@H](c2cccc(-c3cncnc3)c2)N=C(N)S1]<br>(±)-6-(but-3-enyl)-4-(3-(pyrimidin-5-yl)phenyl)-5,6-dihydro-4H-1,3-thiazin-2-amine | 325.2 |
| 7 | 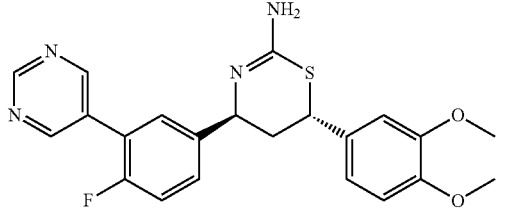 [SMILES: COc1ccc([C@@H]2C[C@@H](c3ccc(F)c(-c4cncnc4)c3)N=C(N)S2)cc1OC]<br>(±)-6-(3,4-dimethoxyphenyl)-4-(4-fluoro-3-(pyrimidin-5-yl)phenyl)-5,6-dihydro-4H-1,3-thiazin-2-amine | 425.1 |

TABLE 1-continued

| Example # | Structure and Chemical Name | MS (M + H)+ |
|---|---|---|
| 8 | 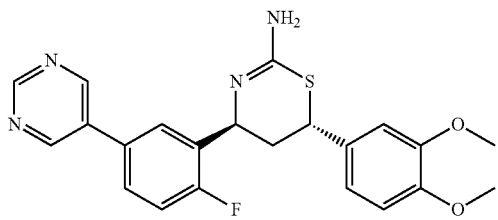 [SMILES: COc1ccc([C@@H]2C[C@@H](c3cc(-c4cncnc4)ccc3F)N=C(N)S2)cc1OC]<br>(±)-6-(3,4-dimethoxyphenyl)-4-(2-fluoro-5-(pyrimidin-5-yl)phenyl)-5,6-dihydro-4H-1,3-thiazin-2-amine | 425.1 |
| 9 | 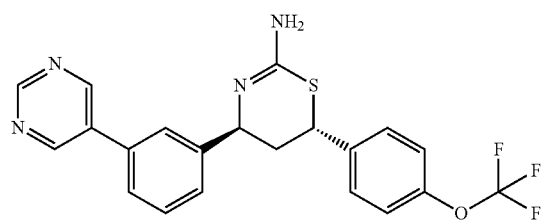 [SMILES: NC1=N[C@H](c2cccc(-c3cncnc3)c2)C[C@@H](c2ccc(OC(F)(F)F)cc2)S1]<br>(±)-4-(3-(pyrimidin-5-yl)phenyl)-6-(4-(trifluoromethoxy)phenyl)-5,6-dihydro-4H-1,3-thiazin-2-amine | 431.4 |
| 10 | 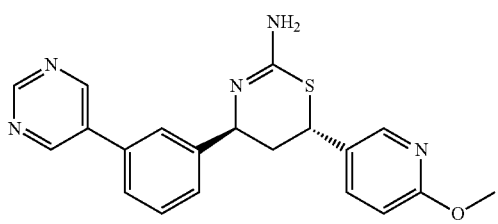 [SMILES: COc1ccc([C@@H]2C[C@@H](c3cccc(-c4cncnc4)c3)N=C(N)S2)cn1]<br>(4S,6S)-6-(6-methoxypyridin-3-yl)-4-(3-(pyrimidin-5-yl)phenyl)-5,6-dihydro-4H-1,3-thiazin-2-amine•TFA | 378.4 |

Example 3A (4S,6S)-6-(3,4-dimethoxyphenyl)-4-(3-(pyrimidin-5-yl)phenyl)-5,6-dihydro-4H-1,3-thiazin-2-amine

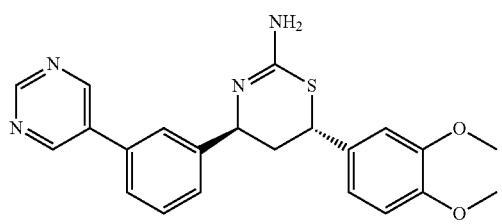 [SMILES: COc1ccc([C@@H]2C[C@@H](c3cccc(-c4cncnc4)c3)N=C(N)S2)cc1OC]

Enantiomer A of Example 3

3-Pyrimidin-5-ylbenzaldehyde (407 mg, 2.210 mmol) and 3,4-dimethoxy-styrene (327 μL, 2.210 mmol) were combined and the resulting product mixture was purified in essentially the same manner as (4S,6S)-4-(2,4-difluoro-5-(pyrimidin-5-yl)phenyl)-6-(3,4-dimethoxyphenyl)-5,6-dihydro-4H-1,3-thiazin-2-amine (Example 1A) to give (4S,6S)-6-(3,4-dimethoxyphenyl)-4-(3-(pyrimidin-5-yl)phenyl)-5,6-dihydro-4H-1,3-thiazin-2-amine (27 mg, 0.063 mmol, 2.9% yield) as a slightly yellow, opaque glass; LC-MS (M+H)+=407.1; $^1$H NMR (500 MHz, CDCl$_3$) δ 9.19 (s, 1H), 8.96 (s, 2H), 7.54-7.43 (m, 3H), 7.34 (d, J=7.3 Hz, 1H), 6.88-6.78 (m, 3H), 5.02 (t, J=4.6 Hz, 1H), 4.20 (dd, J=9.2, 4.0 Hz, 1H), 3.86 (d, J=1.8 Hz, 6H), 2.34-2.16 (m, 2H).

Example 7A (4S,6S)-6-(3,4-dimethoxyphenyl)-4-(4-fluoro-3-(pyrimidin-5-yl)phenyl)-5,6-dihydro-4H-1,3-thiazin-2-amine

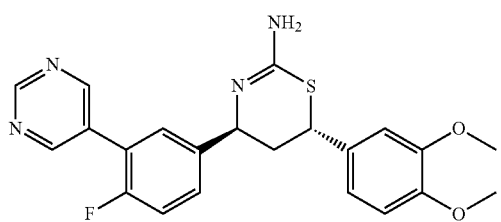 [SMILES: COc1ccc([C@@H]2C[C@@H](c3ccc(F)c(-c4cncnc4)c3)N=C(N)S2)cc1OC]

Enantiomer A of Example 7

4-fluoro-3-(pyrimidin-5-yl)benzaldehyde (Preparation 4) (100 mg, 0.495 mmol) and 3,4-dimethoxystyrene (73.2E μL, 0.495 mmol) were combined and the resulting product mixture was purified in essentially the same manner as (4S,6S)-4-(2,4-difluoro-5-(pyrimidin-5-yl)phenyl)-6-(3,4-dimethoxyphenyl)-5,6-dihydro-4H-1,3-thiazin-2-amine (Example 1A) to give (4S,6S)-6-(3,4-dimethoxyphenyl)-4-(4-fluoro-3-(pyrimidin-5-yl)phenyl)-5,6-dihydro-4H-1,3-thiazin-2-amine (4.9 mg, 0.012 mmol, 2.3% yield) as an opaque glass; LC-MS (M+H)⁺=425.1; ¹H NMR (400 MHz, CDCl₃) δ 9.22 (s, 1H), 8.96 (d, J=1.5 Hz, 2H), 7.36-7.29 (m, 2H), 7.26-7.17 (m, 1H), 6.89-6.79 (m, 3H), 4.98 (t, J=4.8 Hz, 1H), 4.20 (dd, J=9.3, 3.8 Hz, 1H), 3.88 (d, J=1.8 Hz, 6H), 2.67 (q, J=7.0 Hz, 2H), 2.33-2.15 (m, 3H).

Example 8A (4S,6S)-6-(3,4-dimethoxyphenyl)-4-(2-fluoro-5-(pyrimidin-5-yl)phenyl)-5,6-dihydro-4H-1,3-thiazin-2-amine

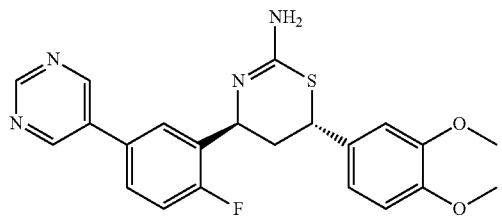 [SMILES: COc1ccc([C@@H]2C[C@@H](c3cc(-c4cncnc4)ccc3F)N=C(N)S2)cc1OC]

Enantiomer A of Example 8

2-fluoro-5-(pyrimidin-5-yl)benzaldehyde (Preparation 5) (100 mg, 0.495 mmol) and 3,4-dimethoxystyrene (73.2 μL, 0.495 mmol) were combined and the resulting product mixture was purified in essentially the same manner as (4S,6S)-4-(2,4-difluoro-5-(pyrimidin-5-yl)phenyl)-6-(3,4-dimethoxyphenyl)-5,6-dihydro-4H-1,3-thiazin-2-amine (Example 1A) to give (4S,6S)-6-(3,4-dimethoxyphenyl)-4-(2-fluoro-5-(pyrimidin-5-yl)phenyl)-5,6-dihydro-4H-1,3-thiazin-2-amine (5.2 mg, 0.012 mmol, 2.3% yield) as an opaque glass; LC-MS (M+H)⁺=425.1; ¹H NMR (400 MHz, CDCl₃) δ 9.21 (s, 1H), 8.97 (s, 2H), 7.54-7.43 (m, 2H), 7.19 (dd, J=9.9, 8.4 Hz, 1H), 6.89-6.79 (m, 3H), 5.32 (t, J=4.6 Hz, 1H), 4.17 (dd, J=9.0, 4.3 Hz, 1H), 3.88 (d, J=4.0 Hz, 6H), 2.34-2.25 (m, 2H).

The following compounds in Table 2 are prepared essentially according to the preparation of (±)-4-(2,4-difluoro-5-(pyrimidin-5-yl)phenyl)-6-(3,4-dimethoxyphenyl)-5,6-dihydro-4H-1,3-thiazin-2-amine (Example 1) except that the reaction mixtures are stirred at 120° C. overnight and the crude reaction mixtures are purified directly by prep HPLC (Phenyl, MeOH/Water/TFA). These compounds are prepared from commercial or other alkenyl heterocycles (Preparations 7-10) and styrenes.

TABLE 2

| Example # | Structure and Chemical Name | MS (M + H)⁺ |
|---|---|---|
| 11 | (±)-6-(2-methoxyphenyl)-4-(3-(pyrimidin-5-yl)phenyl)-5,6-dihydro-4H-1,3-thiazin-2-amine•TFA | 377.1 |
| 12 | 4-((±)-2-amino-4-(3-(pyrimidin-5-yl)phenyl)-5,6-dihydro-4H-1,3-thiazin-6-yl)benzonitrile | 372.1 |
| 13 | (±)-6-(4-methoxyphenyl)-4-(3-(pyrimidin-5-yl)phenyl)-5,6-dihydro-4H-1,3-thiazin-2-amine | 377.1 |

TABLE 2-continued

| Example # | Structure and Chemical Name | MS (M + H)+ |
|---|---|---|
| 14 | 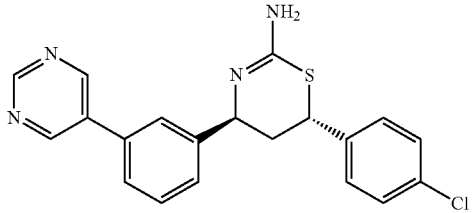 [SMILES: NC1=N[C@H](c2cccc(-c3cncnc3)c2)C[C@@H](c2ccc(Cl)cc2)S1]<br>(±)-6-(4-chlorophenyl)-4-(3-(pyrimidin-5-yl)phenyl)-5,6-dihydro-4H-1,3-thiazin-2-amine•TFA | 381.0 |
| 15 | 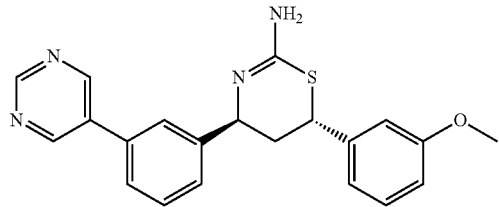 [SMILES: COc1cccc([C@@H]2C[C@@H](c3cccc(-c4cncnc4)c3)N=C(N)S2)c1]<br>(±)-6-(3-methoxyphenyl)-4-(3-(pyrimidin-5-yl)phenyl)-5,6-dihydro-4H-1,3-thiazin-2-amine•TFA | 377.1 |
| 16 | 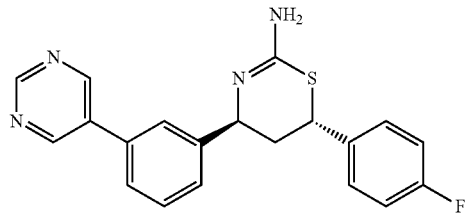 [SMILES: NC1=N[C@H](c2cccc(-c3cncnc3)c2)C[C@@H](c2ccc(F)cc2)S1]<br>(±)-6-(4-fluorophenyl)-4-(3-(pyrimidin-5-yl)phenyl)-5,6-dihydro-4H-1,3-thiazin-2-amine•TFA | 365.0 |
| 17 | 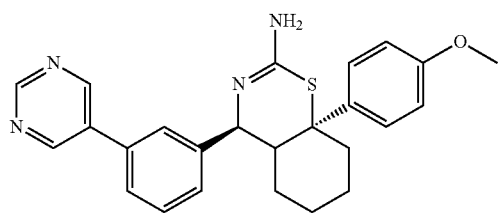 [SMILES: COc1ccc([C@]23CCCCC2[C@@H](c2cccc(-c4cncnc4)c2)N=C(N)S3)cc1]<br>(±)-8a-(4-methoxyphenyl)-4-(3-(pyrimidin-5-yl)phenyl)-4a,5,6,7,8,8a-hexahydro-4H-benzo[e][1,3]thiazin-2-amine•TFA | 431 |
| 18 | 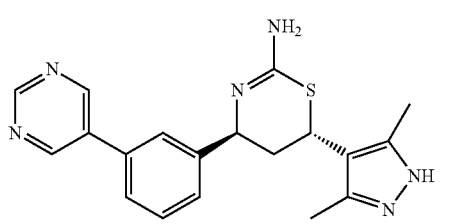 [SMILES: Cc1n[nH]c(C)c1[C@@H]1C[C@@H](c2cccc(-c3cncnc3)c2)N=C(N)S1]<br>(±)-6-(3,5-dimethyl-1H-pyrazol-4-yl)-4-(3-(pyrimidin-5-yl)phenyl)-5,6-dihydro-4H-1,3-thiazin-2-amine•TFA | 365.1 |

TABLE 2-continued

| Example # | Structure and Chemical Name | MS (M + H)+ |
|---|---|---|
| 19 | (±)-6-(3,5-dimethylisoxazol-4-yl)-4-(3-(pyrimidin-5-yl)phenyl)-5,6-dihydro-4H-1,3-thiazin-2-amine•TFA | 366.0 |
| 20 | (±)-6-(pyridin-3-yl)-4-(3-(pyrimidin-5-yl)phenyl)-5,6-dihydro-4H-1,3-thiazin-2-amine•TFA | 348.0 |
| 21 | (±)-6-(1H-imidazol-4-yl)-4-(3-(pyrimidin-5-yl)phenyl)-5,6-dihydro-4H-1,3-thiazin-2-amine•TFA | 337.1 |
| 22 | (±)-6-(pyridin-2-yl)-4-(3-(pyrimidin-5-yl)phenyl)-5,6-dihydro-4H-1,3-thiazin-2-amine•TFA | 348.0 |
| 23 | (±)-6-(pyrazin-2-yl)-4-(3-(pyrimidin-5-yl)phenyl)-5,6-dihydro-4H-1,3-thiazin-2-amine•TFA | 349.1 |

TABLE 2-continued

| Example # | Structure and Chemical Name | MS (M + H)+ |
|---|---|---|
| 24 | (±)-6-(4-methylthiazol-5-yl)-4-(3-(pyrimidin-5-yl)phenyl)-5,6-dihydro-4H-1,3-thiazin-2-amine•TFA | 368.0 |
| 25 | (±)-6-(1,5-dimethyl-1H-pyrazol-4-yl)-4-(3-(pyrimidin-5-yl)phenyl)-5,6-dihydro-4H-1,3-thiazin-2-amine•TFA | 365.0 |
| 26 | (±)-6-(1,3-dimethyl-1H-pyrazol-4-yl)-4-(3-(pyrimidin-5-yl)phenyl)-5,6-dihydro-4H-1,3-thiazin-2-amine•TFA | 365.0 |
| 27 | (±)-6-(1-methyl-1H-pyrazol-4-yl)-4-(3-(pyrimidin-5-yl)phenyl)-5,6-dihydro-4H-1,3-thiazin-2-amine•TFA | 351.3 |
| 28 | (±)-4-(3-(pyrimidin-5-yl)phenyl)-6-(1,3,5-trimethyl-1H-pyrazol-4-yl)-5,6-dihydro-4H-1,3-thiazin-2-amine•TFA | 379.1 |

Example 29

(±)-4-(2,4-difluoro-5-(pyrimidin-5-yl)phenyl)-6-(3,5-dimethylisoxazol-4-yl)-5,6-dihydro-4H-1,3-thiazin-2-amine

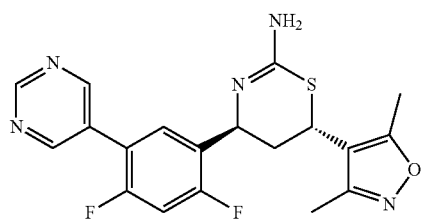

Diastereomer B

To a solution of 2,4-difluoro-5-(pyrimidin-5-yl)benzaldehyde (Preparation 3, 250 mg, 1.135 mmol) in DMF (1135 µL) was added thiourea (104 mg, 1.363 mmol), 3,5-dimethyl-4-vinylisoxazole (280 mg, 2.271 mmol), and chlorotrimethylsilane (218 µL, 1.703 mmol). The resulting mixture was brought to 120° C. and stirred for 1 h. The mixture was then diluted with EtOAc (12 mL), washed with 1 N aqueous NaOH (2×4 mL), water (4 mL), brine (4 mL), dried over MgSO$_4$, filtered and concentrated in vacuo. Purification by flash chromatography (Silica, MeOH/CHCl3) gave a slightly yellow oil consisting primarily of 2 peaks with the desired MW by LC/MS. This oil was further purified (diastereomer separation) by prep HPLC (C18, MeOH/Water/TFA) to give (±)-4-(2,4-difluoro-5-(pyrimidin-5-yl)phenyl)-6-(3,5-dimethylisoxazol-4-yl)-5,6-dihydro-4H-1,3-thiazin-2-amine (20.0 mg, 0.035 mmol, 3.08% yield), the first major peak to elute, as an opaque white glass; LC-MS (M+H)$^+$=402.4; $^1$H NMR (500 MHz, CDCl$_3$) δ 9.25 (s, 1H), 8.94 (d, J=1.4 Hz, 2H), 7.41 (t, J=8.3 Hz, 1H), 7.03 (t, J=10.0 Hz, 1H), 5.26 (t, J=4.6 Hz, 1H), 4.14 (q, J=7.1 Hz, 1H), 4.09 (dd, J=10.0, 3.9 Hz, 1H), 2.37 (s, 3H), 2.35-2.30 (m, 1H), 2.27 (s, 3H), 2.16 (dt, J=13.8, 4.5 Hz, 1H).

Example 29A (4S,6S)-4-(2,4-difluoro-5-(pyrimidin-5-yl)phenyl)-6-(3,5-dimethylisoxazol-4-yl)-5,6-dihydro-4H-1,3-thiazin-2-amine

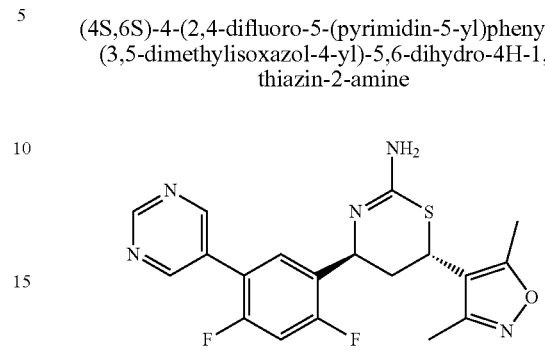

Enantiomer A of Example 29

(±)-4-(2,4-difluoro-5-(pyrimidin-5-yl)phenyl)-6-(3,5-dimethylisoxazol-4-yl)-5,6-dihydro-4H-1,3-thiazin-2-amine (Example 29) was separated by Chiral SFC (Chiralpak AD-H, MeOH/CO$_2$/Diethyl amine) to give (4S,6S)-4-(2,4-difluoro-5-(pyrimidin-5-yl)phenyl)-6-(3,5-dimethylisoxazol-4-yl)-5,6-dihydro-4H-1,3-thiazin-2-amine (5.1 mg, 0.011 mmol, 1.0% yield, first peak to elute) as a clear, colorless glass; LC-MS (M+H)$^+$=402.3; $^1$H NMR (500 MHz, CDCl$_3$) δ 9.18 (s, 1H), 8.99 (d, J=1.4 Hz, 2H), 7.51 (t, J=8.4 Hz, 1H), 7.23 (t, J=10.3 Hz, 1H), 5.15 (t, J=4.7 Hz, 1H), 4.23 (dd, J=9.7, 3.9 Hz, 1H), 2.36 (s, 3H), 2.35-2.29 (m, 1H), 2.25 (s, 3H), 2.20 (dt, J=13.8, 4.8 Hz, 1H).

The following compounds in Table 3 are prepared essentially according to the preparation of (±)-4-(2,4-difluoro-5-(pyrimidin-5-yl)phenyl)-6-(3,5-dimethylisoxazol-4-yl)-5,6-dihydro-4H-1,3-thiazin-2-amine (Example 29) from the appropriate commercial or other aldehydes (Preparations 3, 11, 12, 15, 18, 19, 23, 24)) and alkenyl heterocycles (Preparations 16, 17) and styrenes.

TABLE 3

| Example # | Structure and Chemical Name | MS (M + H)$^+$ |
| --- | --- | --- |
| 30 | ![structure] (±)-6-(3,4-dimethoxyphenyl)-4-(4-(pyrimidin-5-yl)thiophen-2-yl)-5,6-dihydro-4H-1,3-thiazin-2-amine | 413.1 |
| 31 | ![structure] 3'-((±)-2-amino-6-(3,4-dimethoxyphenyl)-5,6-dihydro-4H-1,3-thiazin-4-yl)biphenyl-3-carbonitrile | 429.2 |

TABLE 3-continued

| Example # | Structure and Chemical Name | MS (M + H)+ |
|---|---|---|
| 32 | (±)-4-(2,4-difluoro-5-(5-(prop-1-ynyl)pyridin-3-yl)phenyl)-6-(3,4-dimethoxyphenyl)-5,6-dihydro-4H-1,3-thiazin-2-amine | 480.3 |
| 33 | (±)-4-(2,4-difluoro-5-(pyrimidin-5-yl)phenyl)-6-methyl-6-(5-methylisoxazol-4-yl)-5,6-dihydro-4H-1,3-thiazin-2-amine | 402.4 |
| 34 | (±)-4-(2,4-difluoro-5-(pyrimidin-5-yl)phenyl)-6-(3,5-dimethylisoxazol-4-yl)-6-methyl-5,6-dihydro-4H-1,3-thiazin-2-amine•TFA | 416.3 |
| 35 | 3-(5-((±)-2-amino-6-(3,5-dimethylisoxazol-4-yl)-5,6-dihydro-4H-1,3-thiazin-4-yl)thiophen-3-yl)benzonitrile | 395.1 |
| 36 | (±)-6-(3,5-dimethylisoxazol-4-yl)-4-(4-(5-(prop-1-ynyl)pyridin-3-yl)thiophen-2-yl)-5,6-dihydro-4H-1,3-thiazin-2-amine | 409.0 |

TABLE 3-continued

| Example # | Structure and Chemical Name | MS (M + H)+ |
|---|---|---|
| 37 | 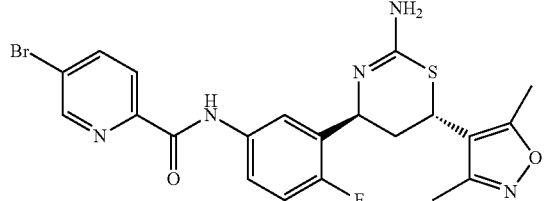<br>N-(3-((±)-2-amino-6-(3,5-dimethylisoxazol-4-yl)-5,6-dihydro-4H-1,3-thiazin-4-yl)-4-fluorophenyl)-5-bromopicolinamide | 506.5 |
| 38 | 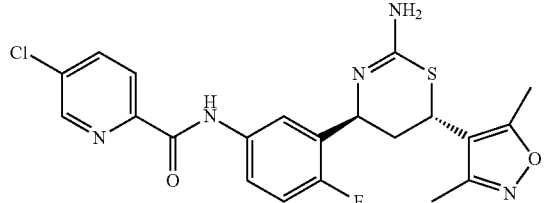<br>N-(3-((±)-2-amino-6-(3,5-dimethylisoxazol-4-yl)-5,6-dihydro-4H-1,3-thiazin-4-yl)-4-fluorophenyl)-5-chloropicolinamide•TFA | 460.0 |

Example 38A

N-(3-((4S,6S)-2-amino-6-(3,5-dimethylisoxazol-4-yl)-5,6-dihydro-4H-1,3-thiazin-4-yl)-4-fluorophenyl)-5-chloropicolinamide

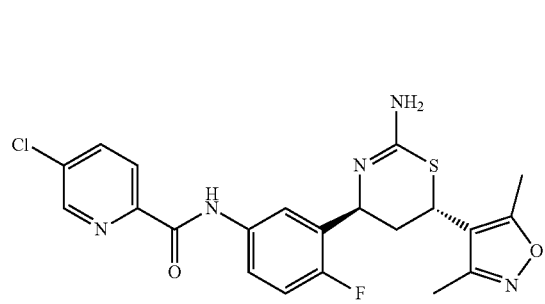 [SMILES: Cc1noc(C)c1[C@@H]1C[C@@H](c2cc(NC(=O)c3ccc(Cl)cn3)ccc2F)N=C(N)S1]

Enantiomer A of Example 38

N-(3-((±)-2-amino-6-(3,5-dimethylisoxazol-4-yl)-5,6-dihydro-4H-1,3-thiazin-4-yl)-4-fluorophenyl)-5-chloropicolinamide (Example 38) was separated by Chiral prep HPLC (Chiralpak AD-H, EtOH/Heptane/Diethyl amine) to give N-(3-((4S,6S)-2-amino-6-(3,5-dimethylisoxazol-4-yl)-5,6-dihydro-4H-1,3-thiazin-4-yl)-4-fluorophenyl)-5-chloropicolinamide (28.5 mg, 0.059 mmol, 3.2% yield, first peak to elute) as a tacky, opaque oil; LC-MS (M+H)+=460.0; $^1$H NMR (500 MHz, DMSO-$d_6$) δ 10.77 (s, 1H), 8.79 (d, J=1.8 Hz, 1H), 8.24-8.13 (m, 2H), 7.82-7.73 (m, 2H), 7.16 (t, J=9.5 Hz, 1H), 6.14 (s, 2H), 5.02 (t, J=4.8 Hz, 1H), 4.27 (dd, J=9.4, 3.6 Hz, 1H), 2.31 (s, 3H), 2.17 (s, 4H), 1.95-1.85 (m, 1H).

Example 39

(4S,6S)-4-(2,4-difluoro-5-(pyrimidin-5-yl)phenyl)-6-(3,5-dimethylisoxazol-4-yl)-4-methyl-5,6-dihydro-4H-1,3-thiazin-2-amine

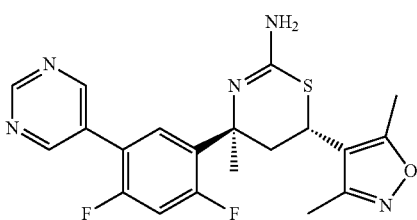 [SMILES: Cc1noc(C)c1[C@@H]1C[C@@](C)(c2cc(-c3cncnc3)c(F)cc2F)N=C(N)S1]

Method A

To a solution of tert-butyl ((4S,6S)-4-(2,4-difluoro-5-(pyrimidin-5-yl)phenyl)-6-(3,5-dimethylisoxazol-4-yl)-4-methyl-5,6-dihydro-4H-1,3-thiazin-2-yl)carbamate (Preparation 41, 2 mg) in CH$_2$Cl$_2$ (0.20 mL) was added TFA (9 μL), and the reaction mixture was stirred at rt for 6 h. The mixture was evaporated in vacuo to give the title compound as a colorless oil (2.5 mg). $^1$H NMR (500 MHz, METHANOL-$d_4$) δ 9.33 (br. s., 1H), 9.14 (br. s., 2H), 7.61-7.36 (m, 2H), 4.27 (dd, J=13.1, 3.4 Hz, 1H), 3.14 (dd, J=14.9, 3.3 Hz, 1H), 2.61 (dd, J=14.6, 13.4 Hz, 1H), 2.38 (s, 3H), 2.28 (s, 3H), 1.90 (s, 3H). MS: 416.4 (M+H)+.

Method B

To a solution of N-(((2S,4R)-2-(2,4-difluoro-5-(pyrimidin-5-yl)phenyl)-4-(3,5-dimethylisoxazol-4-yl)-4-hydroxybutan-2-yl)carbamothioyl)benzamide (Preparation 48, 40 mg, 0.074 mmol) in dioxane (248 μL) was added HCl (1191 μL, 5.95 mmol), and the reaction mixture was heated at 90° C. for 3 h. The crude reaction mixture was purified by reverse phase preparative HPLC on a Luna C18 column (10

μM, 30×100 mm) eluting with 0-100% B (A: 10% MeOH/ 90% water/0.1% TFA; B: 90% MeOH/10% water/0.1% TFA) over 12 min to give a mixture of cis and trans isomers. This mixture was purified by preparative TLC on silica gel (0.50 mm thickness) eluting with 90% DCM/9% MeOH/1% ammonium hydroxide to give (4S,6S)-4-(2,4-difluoro-5-(pyrimidin-5-yl)phenyl)-6-(3,5-dimethylisoxazol-4-yl)-4-methyl-5,6-dihydro-4H-1,3-thiazin-2-amine (13 mg, 0.031 mmol, 42.1% yield). $^1$H NMR (500 MHz, CHLOROFORM-d) δ 9.22 (s, 1H), 8.93 (d, J=1.4 Hz, 2H), 7.45 (t, J=8.8 Hz, 1H), 7.04 (dd, J=11.4, 9.9 Hz, 1H), 3.80 (dd, J=13.1, 3.2 Hz, 1H), 2.86-2.77 (m, 1H), 2.31 (s, 3H), 2.24 (s, 3H), 1.91 (t, J=13.6 Hz, 1H), 1.70 (d, J=0.8 Hz, 3H). MS (M+H) 416.21.

Example 40

(4S,6S)-4-(2,4-difluoro-5-(2-methylpyrimidin-5-yl) phenyl)-6-(3,5-dimethylisoxazol-4-yl)-4-methyl-5,6-dihydro-4H-1,3-thiazin-2-amine

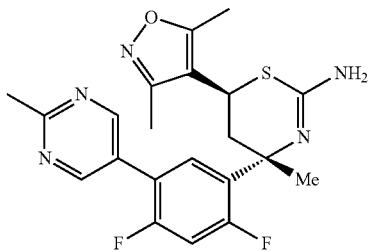 [SMILES: Cc1ncc(-c2cc([C@]3(C)C[C@@H](c4c(C)noc4C)SC(N)=N3)c(F)cc2F)cn1]

A solution of tert-butyl ((4S,6S)-4-(2,4-difluoro-5-(2-methylpyrimidin-5-yl)phenyl)-6-(3,5-dimethylisoxazol-4-yl)-4-methyl-5,6-dihydro-4H-1,3-thiazin-2-yl)carbamate (Preparation 71, 11 mg, 0.021 mmol) and TFA (28.8 μL, 0.374 mmol) in DCM (208 μL) was stirred at rt for 2 h. The solvents were removed to give (4S,6S)-4-(2,4-difluoro-5-(2-methylpyrimidin-5-yl)phenyl)-6-(3,5-dimethylisoxazol-4-yl)-4-methyl-5,6-dihydro-4H-1,3-thiazin-2-amine (13 mg, 0.030 mmol, 146% yield) as its TFA salt as a colorless oil. $^1$H NMR (500 MHz, METHANOL-d$_4$) δ 8.91 (s, 2H), 7.48 (t, J=8.5 Hz, 1H), 7.42 (dd, J=12.1, 10.1 Hz, 1H), 4.26 (dd, J=13.1, 3.2 Hz, 1H), 3.13 (dd, J=14.8, 3.4 Hz, 1H), 2.78 (s, 3H), 2.60 (dd, J=14.6, 13.3 Hz, 1H), 2.37 (s, 3H), 2.27 (s, 3H), 1.90 (s, 3H). MS (M+H) 430.14.

Example 41

(4S,6S)-4-(2,4-difluoro-5-(pyrimidin-5-yl)phenyl)-6-(2,5-dimethyloxazol-4-yl)-4-methyl-5,6-dihydro-4H-1,3-thiazin-2-amine

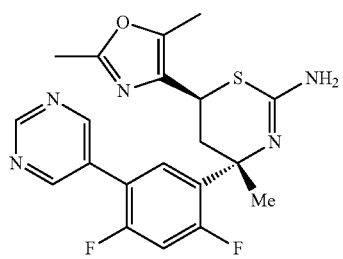 [SMILES: Cc1nc([C@@H]2C[C@@](C)(c3cc(-c4cncnc4)c(F)cc3F)N=C(N)S2)c(C)o1]

To a solution of N-(((2S,4R)-2-(2,4-difluoro-5-(pyrimidin-5-yl)phenyl)-4-(2,5-dimethyloxazol-4-yl)-4-hydroxybutan-2-yl)carbamothioyl)benzamide (Preparation 54, 20 mg, 0.037 mmol) in dioxane (124 μL) was added HCl (595 μL, 2.98 mmol), and the reaction mixture was heated at 90° C. for 2.5. The crude reaction mixture was purified by reverse phase preparative HPLC on a Luna C18 column (10 μM, 30×100 mm) eluting with 0-100% B (A: 10% MeOH/ 90% water/0.1% TFA; B: 90% MeOH/10% water/0.1% TFA) over 12 min to give two fractions. Both isomers were combined and the combined residue was purified by preparative TLC on silica gel (0.50 mm thickness) eluting with 90% DCM/9% MeOH/1% ammonium hydroxide to give (4S,6S)-4-(2,4-difluoro-5-(pyrimidin-5-yl)phenyl)-6-(2,5-dimethyloxazol-4-yl)-4-methyl-5,6-dihydro-4H-1,3-thiazin-2-amine (3 mg, 7.22 μmol, 19.41% yield) and (4S,6R)-4-(2,4-difluoro-5-(pyrimidin-5-yl)phenyl)-6-(2,5-dimethyloxazol-4-yl)-4-methyl-5,6-dihydro-4H-1,3-thiazin-2-amine (2 mg, 4.81 μmol, 12.94% yield). $^1$H NMR (500 MHz, CHLOROFORM-d) 9.24 (s, 1H), 8.95 (d, J=1.4 Hz, 2H), 7.48-7.42 (m, 1H), 7.02 (dd, J=11.3, 9.9 Hz, 1H), 4.75 (s, 1H), 3.86 (dd, J=12.7, 3.3 Hz, 1H), 2.86 (dd, J=14.2, 2.7 Hz, 1H), 2.41 (s, 3H), 2.17-2.14 (m, 1H), 2.16 (s, 3H), 1.74 (s, 3H). MS (M+H)$^+$: 417.19.

Example 42

(4S,6S)-4-(2,4-difluoro-5-(pyrimidin-5-yl)phenyl)-6-(2,4-dimethyloxazol-5-yl)-4-methyl-5,6-dihydro-4H-1,3-thiazin-2-amine

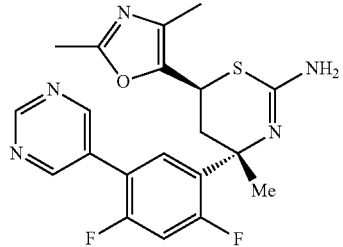 [SMILES: Cc1nc(C)c([C@@H]2C[C@@](C)(c3cc(-c4cncnc4)c(F)cc3F)N=C(N)S2)o1]

To a solution of N-(((2S,4R)-2-(2,4-difluoro-5-(pyrimidin-5-yl)phenyl)-4-(2,4-dimethyloxazol-5-yl)-4-hydroxybutan-2-yl)carbamothioyl)benzamide (Preparation 60, 50 mg, 0.093 mmol) in dioxane (310 μL) was added HCl (1488 μL, 7.44 mmol), and the reaction mixture was heated at 90° C. for 2.5 h. The crude reaction mixture was purified by reverse phase preparative HPLC on a Luna C18 column (10 μM, 30×100 mm) eluting with 0-100% B (A: 10% MeOH/90% water/0.1% TFA; B: 90% MeOH/10% water/ 0.1% TFA) over 12 min to give a mixture of two isomers. This mixture was purified by preparative TLC on silica gel (0.50 mm thickness) eluting with 90% DCM/9% MeOH/1% ammonium hydroxide to give (4S,6S)-4-(2,4-difluoro-5-(pyrimidin-5-yl)phenyl)-6-(2,4-dimethyloxazol-5-yl)-4-methyl-5,6-dihydro-4H-1,3-thiazin-2-amine (7 mg, 0.017 mmol, 18.12% yield) as white solid. $^1$H NMR (500 MHz, CHLOROFORM-d) δ 9.23 (s, 1H), 8.94 (d, J=1.2 Hz, 2H), 7.42 (t, J=8.8 Hz, 1H), 7.04 (dd, J=11.3, 9.9 Hz, 1H), 4.03 (dd, J=12.9, 3.4 Hz, 1H), 2.89 (dd, J=14.2, 3.4 Hz, 1H), 2.42 (s, 3H), 2.07 (t, J=13.5 Hz, 1H), 2.01 (s, 3H), 1.73 (s, 3H). MS (M+H)$^+$: 416.21.

Example 43

(4S,6S)-4-(2,4-difluoro-5-(pyrimidin-5-yl)phenyl)-6-(2,4-dimethylthiazol-5-yl)-4-methyl-5,6-dihydro-4H-1,3-thiazin-2-amine

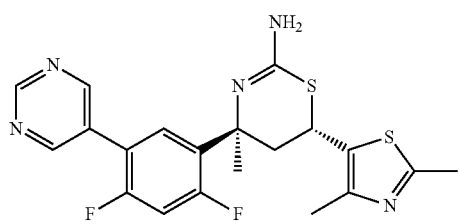 [SMILES: Cc1nc(C)c([C@@H]2C[C@@](C)(c3cc(-c4cncnc4)c(F)cc3F)N=C(N)S2)s1]

This compound is prepared essentially according to the preparation of Example 39 (Method B) from the commercially available 1-(2,4-dimethylthiazol-5-yl)ethanone to give (4S,6S)-4-(2,4-difluoro-5-(pyrimidin-5-yl)phenyl)-6-(2,4-dimethylthiazol-5-yl)-4-methyl-5,6-dihydro-4H-1,3-thiazin-2-amine; LC-MS (M+H)+=432.2; $^1$H NMR (500 MHz, CHLOROFORM-d) δ 9.28-9.21 (m, 1H), 8.96 (d, J=1.4 Hz, 2H), 7.44 (t, J=8.8 Hz, 1H), 7.05 (dd, J=11.4, 9.9 Hz, 1H), 4.16 (dd, J=12.7, 3.2 Hz, 1H), 3.02 (dd, J=14.4, 3.3 Hz, 1H), 2.68-2.59 (m, 4H), 2.20-2.11 (m, 3H), 1.87-1.77 (m, 2H), 1.73 (s, 3H).

Example 44

(4S,6S)-4-(3-chloro-5-(5-(prop-1-ynyl)pyridin-3-yl)thiophen-2-yl)-6-(3,5-dimethylisoxazol-4-yl)-4-methyl-5,6-dihydro-4H-1,3-thiazin-2-amine

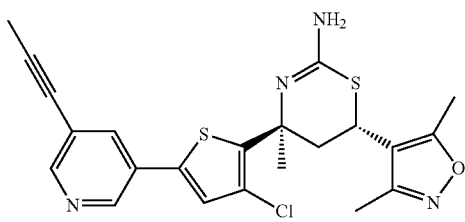 [SMILES: CC#Cc1cncc(-c2cc(Cl)c([C@]3(C)C[C@@H](c4c(C)noc4C)SC(N)=N3)s2)c1]

To a solution of tert-butyl ((4S,6S)-4-(3-chloro-5-(5-(prop-1-yn-1-yl)pyridin-3-yl)thiophen-2-yl)-6-(3,5-dimethylisoxazol-4-yl)-4-methyl-5,6-dihydro-4H-1,3-thiazin-2-yl)carbamate (Preparation 64, 16 mg, 0.029 mmol) in DCM (287 μL) was added TFA (30 μL, 0.389 mmol). The resulting mixture was stirred at rt for 1 h. The reaction mixture was then concentrated in vacuo. Purification by flash chromatography (Silica, MeOH/CHCl$_3$) gave (4S,6S)-4-(3-chloro-5-(5-(prop-1-yn-1-yl)pyridin-3-yl)thiophen-2-yl)-6-(3,5-dimethylisoxazol-4-yl)-4-methyl-5,6-dihydro-4H-1,3-thiazin-2-amine, TFA (8.5 mg, 0.013 mmol, 46.6% yield) as an opaque glass; LC-MS (M+H)+=457.2; $^1$H NMR (500 MHz, CHLOROFORM-d) δ 8.69 (d, J=2.3 Hz, 1H), 8.53 (d, J=2.0 Hz, 1H), 7.82 (t, J=2.1 Hz, 1H), 7.21 (s, 1H), 4.11 (dd, J=12.9, 3.1 Hz, 1H), 3.18 (dd, J=14.0, 3.1 Hz, 1H), 2.37 (s, 3H), 2.29 (s, 3H), 2.11 (s, 3H), 1.76 (s, 3H).

Example 45

(4S,6S)-4-(2,4-difluorophenyl)-6-(3,5-dimethylisoxazol-4-yl)-4-methyl-5,6-dihydro-4H-1,3-thiazin-2-amine

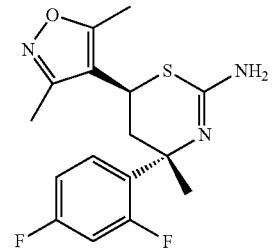 [SMILES: Cc1noc(C)c1[C@@H]1C[C@@](C)(c2ccc(F)cc2F)N=C(N)S1]

To a solution of tert-butyl ((4S,6R)-4-(2,4-difluorophenyl)-6-(3,5-dimethylisoxazol-4-yl)-4-methyl-5,6-dihydro-4H-1,3-thiazin-2-yl)carbamate (Preparation 65, 21.5 mg, 0.049 mmol) in DCM (1.5 mL) was added TFA (200 μL, 2.60 mmol). The resulting mixture was stirred at rt for 1 h. The reaction mixture was then concentrated in vacuo to give the crude oil. Purification by flash chromatography (Silica, 0-15% MeOH/CHCl3) gave (4S,6R)-4-(2,4-difluorophenyl)-6-(3,5-dimethylisoxazol-4-yl)-4-methyl-5,6-dihydro-4H-1,3-thiazin-2-amine, TFA (14.4 mg, 0.030 mmol, 61.7% yield) as an opaque glass; LC-MS (M+H)+=338.1; $^1$H NMR (500 MHz, CHLOROFORM-d) δ 7.31 (d, J=7.2 Hz, 1H), 6.92 (br. s., 1H), 6.86 (t, J=8.9 Hz, 1H), 5.06 (br. s., 1H), 3.76 (d, J=12.5 Hz, 1H), 2.79 (d, J=13.6 Hz, 1H), 2.29 (br. s., 3H), 2.21 (br. s., 3H), 1.94 (t, J=13.3 Hz, 1H), 1.70 (br. s., 3H).

Example 46

(4S,6S)-4-(2,4-difluoro-5-(2-fluoropyrimidin-5-yl)phenyl)-6-(3,5-dimethylisoxazol-4-yl)-4-methyl-5,6-dihydro-4H-1,3-thiazin-2-amine

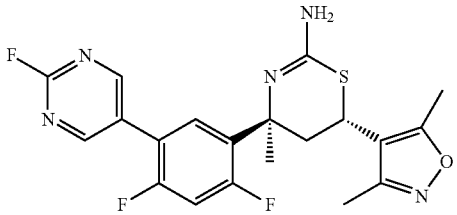

To a solution of tert-butyl ((4S,6S)-4-(2,4-difluoro-5-(2-fluoropyrimidin-5-yl)phenyl)-6-(3,5-dimethylisoxazol-4-yl)-4-methyl-5,6-dihydro-4H-1,3-thiazin-2-yl)carbamate (Preparation 67, 33.1 mg, 0.062 mmol) in DCM (2 mL) was added TFA (200 μL, 2.60 mmol). The resulting mixture was stirred at rt for 1 h. The reaction mixture was then diluted with EtOAc (10 ml) and brought to pH 8 by the addition of 1 N aqueous NaOH. The layers were separated and the aqueous layer was washed with EtOAc (3 mL). The combined organic layers were washed with water (5 mL), brine (5 mL), dried over MgSO$_4$, filtered and concentrated in vacuo to give the crude oil. Purification by prep HPLC (C18, MeOH/Water/NH$_4$OAc) gave (4S,6S)-4-(2,4-difluoro-5-(2-fluoropyrimidin-5-yl)phenyl)-6-(3,5-dimethylisoxazol-4- yl)-4-methyl-5,6-dihydro-4H-1,3-thiazin-2-amine (3.7 mg, 0.082 mmol, 13.2% yield); LC-MS (M+H)+=434.0; $^1$H NMR (500 MHz, DMSO-d$_6$) δ 8.95 (s, 2H), 7.60-7.50 (m, 1H), 7.46 (t, J=9.0 Hz, 1H), 6.28 (br. s., 2H), 3.75 (dd, J=12.8, 3.1 Hz, 1H), 2.69-2.59 (m, 1H), 2.29 (s, 3H), 2.17 (s, 3H), 1.88 (t, J=13.3 Hz, 1H), 1.59 (s, 3H).

Example 47

1-(5-((4S,6S)-2-amino-6-(3,5-dimethylisoxazol-4-yl)-4-methyl-5,6-dihydro-4H-1,3-thiazin-4-yl)-2,4-difluorophenyl)ethanone

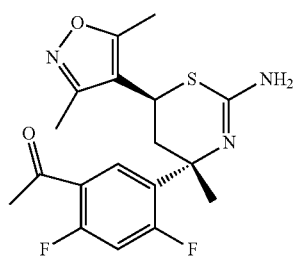 [SMILES: CC(=O)c1cc([C@]2(C)C[C@@H](c3c(C)noc3C)SC(N)=N2)c(F)cc1F]

To a solution of tert-butyl ((4S,6S)-4-(5-acetyl-2,4-difluorophenyl)-6-(3,5-dimethylisoxazol-4-yl)-4-methyl-5,6-dihydro-4H-1,3-thiazin-2-yl)carbamate (Preparation 68, 22 mg, 0.046 mmol) in DCM (2 mL) was added TFA (200 μL, 2.60 mmol). The resulting mixture was stirred at rt for 2 h. The reaction mixture was then concentrated in vacuo to give the crude oil. Purification by prep HPLC (C18, MeOH/Water/NH$_4$OAc) gave 1-(5-((4S,6S)-2-amino-6-(3,5-dimethylisoxazol-4-yl)-4-methyl-5,6-dihydro-4H-1,3-thiazin-4-yl)-2,4-difluorophenyl)ethanone (10.4 mg, 0.027 mmol, 59.7% yield); LC-MS (M+H)+=380.1; $^1$H NMR (500 MHz, DMSO-d$_6$) δ 7.85 (t, J=9.2 Hz, 1H), 7.45 (t, J=11.1 Hz, 1H), 6.33 (br. s., 2H), 3.63 (d, J=13.7 Hz, 1H), 2.67-2.55 (m, 4H), 2.26 (s, 3H), 2.15 (s, 3H), 1.89-1.80 (m, 1H), 1.53 (s, 3H).

Example 48

1-(4-((4S,6S)-2-amino-4-(2,4-difluorophenyl)-4-methyl-5,6-dihydro-4H-1,3-thiazin-6-yl)-3-methyl-isoxazol-5-yl)-2-methylpropan-2-ol

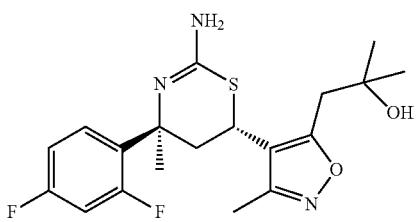 [SMILES: Cc1noc(CC(C)(C)O)c1[C@@H]1C[C@@](C)(c2ccc(F)cc2F)N=C(N)S1]

To a solution of tert-butyl (4S,6S)-4-(2,4-difluorophenyl)-6-(5-(2-hydroxy-2-methylpropyl)-3-methylisoxazol-4-yl)-4-methyl-5,6-dihydro-4H-1,3-thiazin-2-ylcarbamate and tert-butyl ((4S,6S)-4-(2,4-difluoro-5-(2-hydroxypropan-2-yl)phenyl)-6-(3,5-dimethylisoxazol-4-yl)-4-methyl-5,6-dihydro-4H-1,3-thiazin-2-yl)carbamate (Preparation 69, 49 mg, 0.099 mmol) in DCM (2 mL) was added TFA (200 μL, 2.60 mmol). The resulting mixture was stirred at rt for 2 h. The mixture was then concentrated in vacuo to give the crude oil. Purification by prep HPLC (C18, MeOH/Water/NH$_4$OAc) gave 1-(4-((4S,6S)-2-amino-4-(2,4-difluorophenyl)-4-methyl-5,6-dihydro-4H-1,3-thiazin-6-yl)-3-methyl-isoxazol-5-yl)-2-methylpropan-2-ol (6.5 mg, 0.016 mmol, 16.6% yield); LC-MS (M+H)+=396.0; $^1$H NMR (500 MHz, DMSO-d$_6$) δ 7.27 (d, J=7.0 Hz, 1H), 7.20 (br. s., 1H), 7.12 (s, 1H), 4.57 (s, 1H), 3.72-3.65 (m, 1H), 2.31 (s, 3H), 1.92 (s, 2H), 1.88 (s, 1H), 1.56 (s, 3H), 0.92 (s, 6H).

Example 49

(4S,6S)-4-(3,5-difluorophenyl)-6-(3,5-dimethylisoxazol-4-yl)-4-methyl-5,6-dihydro-4H-1,3-thiazin-2-amine

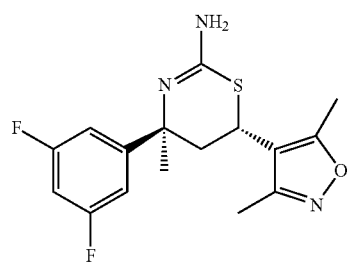 [SMILES: Cc1noc(C)c1[C@@H]1C[C@@](C)(c2cc(F)cc(F)c2)N=C(N)S1]

This compound was prepared in a manner similar to that reported for the preparation of Example 39 (Method B) from the commercially available 1-(3,5-difluorophenyl)ethanone to give (4S,6S)-4-(3,5-difluorophenyl)-6-(3,5-dimethylisoxazol-4-yl)-4-methyl-5,6-dihydro-4H-1,3-thiazin-2-amine; LC-MS (M+H)+=338.4; $^1$H NMR (500 MHz, DMSO-d$_6$) δ 7.17-6.99 (m, 3H), 6.21 (br. s., 2H), 3.60 (dd, J=13.0, 2.9 Hz, 1H), 2.58 (dd, J=13.9, 2.9 Hz, 1H), 2.26 (s, 3H), 2.13 (s, 3H), 1.81 (t, J=13.4 Hz, 1H), 1.47 (s, 3H).

Example 50

(4S,6S)-6-(3,5-dimethylisoxazol-4-yl)-4-methyl-4-(3,4,5-trifluorophenyl)-5,6-dihydro-4H-1,3-thiazin-2-amine

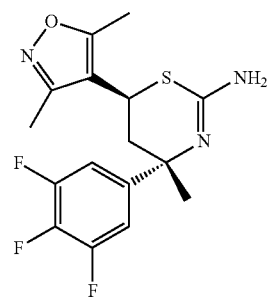 [SMILES: Cc1noc(C)c1[C@@H]1C[C@@](C)(c2cc(F)c(F)c(F)c2)N=C(N)S1]

This compound was prepared in a manner similar to that reported for the preparation of Example 39 (Method B) from the commercially available 1-(3,4,5-trifluorophenyl)ethanone. (4S,6S)-6-(3,5-dimethylisoxazol-4-yl)-4-methyl-4-(3,4,5-trifluorophenyl)-5,6-dihydro-4H-1,3-thiazin-2-amine; LC-MS (M+H)+=356.1; $^1$H NMR (500 MHz, DMSO-d$_6$) δ 7.28 (dd, J=9.9, 6.9 Hz, 2H), 6.25 (br. s., 2H), 3.62 (dd, J=12.8, 2.7 Hz, 1H), 2.59 (dd, J=14.0, 3.1 Hz, 1H), 2.28 (s, 3H), 2.15 (s, 3H), 1.81 (t, J=13.4 Hz, 1H), 1.46 (s, 3H).

Example 51

(4S,6S)-4-(2,4-difluorophenyl)-6-(3,5-dimethylisoxazol-4-yl)-4-ethyl-5,6-dihydro-4H-1,3-thiazin-2-amine

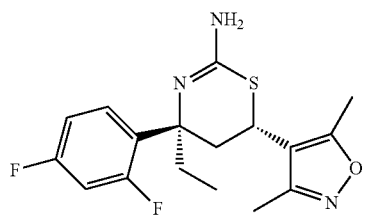 [SMILES: CC[C@@]1(c2ccc(F)cc2F)C[C@@H](c2c(C)noc2C)SC(N)=N1]

This compound was prepared in a manner similar to that reported for the preparation of Example 39 (Method B) from the commercially available 1-(2,4-difluorophenyl)propan-1-one to give (4S,6S)-4-(2,4-difluorophenyl)-6-(3,5-dimethylisoxazol-4-yl)-4-ethyl-5,6-dihydro-4H-1,3-thiazin-2-amine; LC-MS (M+H)+=352.0; $^1$H NMR (500 MHz, DMSO-$d_6$) δ 7.37-7.18 (m, 2H), 7.13 (t, J=8.4 Hz, 1H), 6.21 (br. s., 2H), 3.66 (d, J=13.7 Hz, 1H), 2.25 (s, 3H), 2.13 (s, 3H), 1.98-1.89 (m, 2H), 1.89-1.77 (m, 1H), 1.73 (d, J=6.1 Hz, 1H), 0.77 (t, J=7.2 Hz, 3H).

The following compounds in Table 4 are prepared in a manner similar to that reported for the preparation of (4S,6S)-4-(2,4-difluoro-5-(2-fluoropyrimidin-5-yl)phenyl)-6-(3,5-dimethylisoxazol-4-yl)-4-methyl-5,6-dihydro-4H-1,3-thiazin-2-amine (Example 46) from the appropriate commercial aryl bromides and 5-((4S,6S)-2-(tert-butoxycarbonylamino)-6-(3,5-dimethylisoxazol-4-yl)-4-methyl-5,6-dihydro-4H-1,3-thiazin-4-yl)-2,4-difluorophenylboronic acid (Preparation 66).

TABLE 4

| Example # | Structure and Chemical Name | MS (M + H)+ |
|---|---|---|
| 52 | (4S,6S)-4-(2,4-difluoro-5-(2-(methylsulfonyl)pyrimidin-5-yl)phenyl)-6-(3,5-dimethylisoxazol-4-yl)-4-methyl-5,6-dihydro-4H-1,3-thiazin-2-amine | 494.2 |
| 53 | 5-(5-((4S,6S)-2-amino-6-(3,5-dimethylisoxazol-4-yl)-4-methyl-5,6-dihydro-4H-1,3-thiazin-4-yl)-2,4-difluorophenyl)pyridin-3-ol | 431.2 |
| 54 | (4S,6S)-4-(2,4-difluoro-5-(6-methoxypyridin-3-yl)phenyl)-6-(3,5-dimethylisoxazol-4-yl)-4-methyl-5,6-dihydro-4H-1,3-thiazin-2-amine | 445.2 |

TABLE 4-continued

| Example # | Structure and Chemical Name | MS (M + H)+ |
|---|---|---|
| 55 | 3-(5-((4S,6S)-2-amino-6-(3,5-dimethylisoxazol-4-yl)-4-methyl-5,6-dihydro-4H-1,3-thiazin-4-yl)-2,4-difluorophenyl)picolinonitrile | 440.3 |
| 56 | (4S,6S)-4-(2,4-difluoro-5-(2-methoxypyridin-3-yl)phenyl)-6-(3,5-dimethylisoxazol-4-yl)-4-methyl-5,6-dihydro-4H-1,3-thiazin-2-amine | 445.2 |
| 57 | (4S,6S)-4-(5-(5-chloro-6-methoxypyridin-3-yl)-2,4-difluorophenyl)-6-(3,5-dimethylisoxazol-4-yl)-4-methyl-5,6-dihydro-4H-1,3-thiazin-2-amine | 479.2 |
| 58 | (4S,6S)-4-(2,4-difluoro-5-(2-methoxypyrimidin-5-yl)phenyl)-6-(3,5-dimethylisoxazol-4-yl)-4-methyl-5,6-dihydro-4H-1,3-thiazin-2-amine | 446.2 |
| 59 | (4S,6S)-4-(2,4-difluoro-5-(4-(trifluoromethyl)pyridin-3-yl)phenyl)-6-(3,5-dimethylisoxazol-4-yl)-4-methyl-5,6-dihydro-4H-1,3-thiazin-2-amine | 483.2 |

Example 60

(4S,6S)-4-(2,4-difluorophenyl)-4-methyl-6-(1-methyl-1H-pyrazol-5-yl)-5,6-dihydro-4H-1,3-thiazin-2-amine

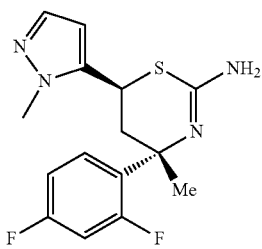 [SMILES: Cn1nccc1[C@@H]1C[C@@](C)(c2ccc(F)cc2F)N=C(N)S1]

To a solution of N-(((2S,4R)-2-(2,4-difluorophenyl)-4-hydroxy-4-(1-methyl-1H-pyrazol-5-yl)butan-2-yl)carbamothioyl)benzamide from preparation 77 (134 mg, 0.301 mmol) in dioxane (1.5 ml) was added 5 M aqueous HCl (3.5 ml, 17.5 mmol). The resulting mixture was sealed in a high pressure vial and heated at 90° C. with stirring for 16 h. The mixture was cooled to rt and concentrated under high vacuum on the rotary evaporator. The residue was purified using reverse phase preparatory HPLC (SunFire PrepC18 OBD 10 mm, 50×250 mm column, 90% MeOH/10% water/0.1% TFA-90% MeOH/10% water/0.1% TFA, linear gradiant over 34 min, 50 ml/min) to afford (4S,6S)-4-(2,4-difluorophenyl)-4-methyl-6-(1-methyl-1H-pyrazol-5-yl)-5,6-dihydro-4H-1,3-thiazin-2-amine, TFA (9.5 mg, 0.021 mmol, 7% yield) as a clear residue. $^1$H NMR (500 MHz, methanol-$d_4$) δ 7.48 (dd, J=2.1, 0.4 Hz, 1H), 7.43-7.34 (m, 1H), 7.21-7.10 (m, 2H), 6.50 (dd, J=2.0, 0.5 Hz, 1H), 4.41 (dd, J=12.6, 3.1 Hz, 1H), 3.71 (s, 3H), 3.22 (dd, J=14.8, 3.2 Hz, 1H), 2.53 (dd, J=14.8, 12.7 Hz, 1H), 1.87 (s, 3H). MS (M+H)$^+$: 323.0.

Example 61

(4S,6S)-4-(2,4-difluorophenyl)-4-methyl-6-(3-methylisoxazol-4-yl)-5,6-dihydro-4H-1,3-thiazin-2-amine

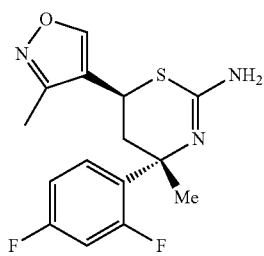 [SMILES: Cc1nocc1[C@@H]1C[C@@](C)(c2ccc(F)cc2F)N=C(N)S1]

To a solution of N-(((2S,4R)-2-(2,4-difluorophenyl)-4-hydroxy-4-(3-methylisoxazol-4-yl)butan-2-yl)carbamothioyl)benzamide from preparation 83 (813 mg, 1.83 mmol) in dioxane (6.1 mL) was added 5 M aqueous HCl (29 mL, 146 mmol). The resulting mixture was brought to 90° C. and stirred for 16 h. The mixture was then allowed to come to rt and aqueous 1 N NaOH was added until the solution became slightly basic. The mixture was then extracted with EtOAc (3×100 mL). The combined organic extracts were washed with water (25 mL) and brine (25 mL), dried over sodium sulfate, filtered and concentrated in vacuo to give 500 mg of the crude oil which was purified using reverse phase preparatory HPLC (SunFire PrepC18 OBD 10 mm, 50×250 mm column, 90% MeOH/10% water/0.1% TFA-90% MeOH/10% water/0.1% TFA, linear gradiant over 34 min, 50 ml/min) to afford (4S,6S)-4-(2,4-difluorophenyl)-4-methyl-6-(3-methylisoxazol-4-yl)-5,6-dihydro-4H-1,3-thiazin-2-amine, TFA (170 mg, 0.381 mmol, 21% yield) as an off-white solid. Data was consistent with the desired structure. $^1$H NMR (400 MHz, methanol-$d_4$) δ 8.75 (s, 1H), 7.41-7.30 (m, 1H), 7.22-7.10 (m, 2H), 4.20 (dd, J=12.7, 3.1 Hz, 1H), 3.17 (dd, J=14.8, 3.3 Hz, 1H), 2.50 (dd, J=14.6, 12.8 Hz, 1H), 2.25 (s, 3H), 1.87 (s, 3H). MS (M+H)$^+$: 324.1.

Example 62

(4S,6S)-4-(2,4-difluorophenyl)-4-methyl-6-(pyrimidin-5-yl)-5,6-dihydro-4H-1,3-thiazin-2-amine

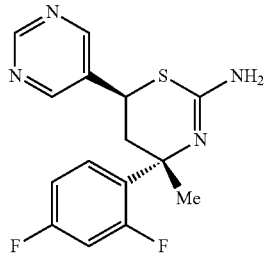 [SMILES: C[C@@]1(c2ccc(F)cc2F)C[C@@H](c2cncnc2)SC(N)=N1]

Procedure, Preparation 87

To a solution of N-(((2S,4R)-2-(2,4-difluorophenyl)-4-hydroxy-4-(pyrimidin-5-yl)butan-2-yl)carbamothioyl)benzamide (1.0 g, 2.260 mmol) in dioxane (40 mL) was added a 5.0 M solution of HCl/water (20 mL, 100 mmol). The mixture was stirred at 90° C. for 3 h. The mixture was concentrated in vacuo to a crude product, and the residue was purified by preparatory HPLC. The sample was purified on a Waters Xbridge C18 19×200 mm column with 5 um particles using the following mobile phases: mobile phase A=water with 20 mM ammonium acetate; mobile phase B=95:5 methanol/water with 20 mM ammonium acetate. Gradient elution was used from 20-60% mobile phase B over 20 minutes, then a 5 minute hold at 100% mobile phase B with a 20 mL/min flow rate. The yield of product was 69.5 mgs. Purity was assessed by LC/MS analysis using a Waters BEH C18 2×50 mm column with 1.7 um particles using the following mobile phases: mobile phase A=5:95 acetonitrile:water with 10 mM ammonium acetate; mobile phase B: 95:5 acetonitrile/water with 10 mM ammonium acetate. Gradient elution was used with a 0.5 min hold at 0% B followed by a gradient of 0-100% B over 4 minutes, then a 0.5 min hold at 100% B with a flow rate of 1 mL/min. The observed retention time was 1.52 minutes and the observed (M+H)$^+$=320.1. $^1$H NMR (500 MHz, DMSO-$d_6$) δ 9.10 (s, 1H), 8.79 (s, 2H), 7.29 (q, J=7.0 Hz, 1H), 7.21 (t, J=9.0 Hz, 1H), 7.11 (t, J=8.4 Hz, 1H), 3.81 (d, J=11.6 Hz, 1H), 2.69 (d, J=14.3 Hz, 1H), 1.98 (t, J=13.3 Hz, 1H), 1.88 (br. s, 3H).

Biological Methods

Cellular Assays for Inhibition of Aβ1-40 and Aβ1-42 Production

H4 cells stably transfected with APP751 containing the Swedish mutation (H4 APP751 SWE clone 8.20, developed at BMS) were maintained in log phase through twice weekly passage at a 1:20 split. For IC$_{50}$ determinations, 30 μl cells (1.5×10$^4$ cells/well) in DMEM media containing 0.0125% BSA (Sigma A8412) were plated directly into 384-well compound plates (Costar 3709) containing 0.1 μl serially diluted compound in DMSO. Following incubation for 19 h in 5% CO$_2$ at 37° C., plates were briefly centrifuged (1000 rpm, 5 min). A 10 μl aliquot from each well was transferred to a second assay plate (Costar 3709) for Aβ40 measurements. Antibody cocktails were freshly prepared by dilution into 40 mM Tris-HCl (pH 7.4) with 0.2% BSA and added to assay plates. For Aβ42 measurements, antibodies specific for the Aβ42 neoepitope (565, developed at BMS; conjugated to the Wallac reagent (Perkin Elmer)) and the N-terminal sequence of Aβ peptide (26D6, developed at SIBIA; conjugated to APC (Perkin Elmer)) were mixed and 20 μl of the mixture was added to each well of the incubated cell plate yielding a final concentration of 0.8 ng/well 565 and 75 ng/well 26D6. For the Aβ40 measurements, antibodies specific for the Aβ40 neoepitope (TSD, developed at BMS; conjugated to the Wallac reagent (Perkin Elmer)) and 26D6 as described above were mixed and 20 μl of the mixture was added to the 10 μl aliquots which had been removed previously from the cell plate yielding a final concentration of 1.6 ng/well TSD and 17.5 ng/well 26D6. Assay plates containing antibodies were sealed with aluminum foil and incubated overnight at 4° C. Signal was determined using a Viewlux counter (Perkin Elmer) and IC$_{50}$ values determined using curve fitting in CurveMaster (Excel Fit based).

The activity of representative compounds of the present invention, based on Aβ42 cellular IC$_{50}$ values in H4 APP751 SWE clone 8.20, are illustrated below in Table 5:

TABLE 5A

Cellular activity of 6-alkyl and 6-substituted phenyl thiazine examples

| Example # | IC$_{50}$ (μM) |
|---|---|
| 1 | 1.1 |
| 1A | 0.29 |
| 2 | 4.1 |
| 3 | 1.1 |
| 3A | 1.1 |
| 4 | 7.4 |
| 5 | 3.8 |
| 6 | 14 |
| 7 | 1.7 |
| 7A | 0.35 |
| 8 | 1.9 |
| 8A | 0.46 |
| 9 | 8.9 |
| 11 | 2.4 |
| 12 | 1.8 |
| 13 | 3.7 |
| 14 | 2.7 |
| 15 | 2.8 |
| 16 | 2.6 |
| 17 | 3.3 |
| 30 | 8.0 |
| 31 | 8.9 |
| 32 | 1.0 |

TABLE 5B

Cellular activity of 6-heterocyclic thiazine examples

| Example # | IC$_{50}$ (μM) |
|---|---|
| 10 | 2.1 |
| 18 | 7.1 |
| 19 | 0.23 |
| 20 | 7.8 |

TABLE 5B-continued

Cellular activity of 6-heterocyclic thiazine examples

| Example # | IC$_{50}$ (μM) |
|---|---|
| 21 | >30 |
| 22 | 2.0 |
| 23 | 2.4 |
| 24 | 1.0 |
| 25 | 3.4 |
| 26 | 2.5 |
| 27 | 2.6 |
| 28 | >30 |
| 29 | 0.20 |
| 29A | 0.060 |
| 33 | 0.18 |
| 34 | 2.7 |
| 35 | 0.30 |
| 36 | 0.060 |
| 37 | 0.022 |
| 38 | 0.011 |
| 38A | 0.005 |
| 39 | 0.008 |
| 40 | 0.186 |
| 41 | 0.233 |
| 42 | 0.108 |
| 43 | 0.21 |
| 44 | 0.03 |
| 45 | 0.15 |
| 46 | 0.39 |
| 47 | 0.22 |
| 48 | 0.11 |
| 49 | 0.27 |
| 50 | 0.84 |
| 51 | 1.3 |
| 52 | 0.82 |
| 53 | 0.30 |
| 54 | 0.32 |
| 55 | 0.087 |
| 56 | 0.67 |
| 57 | 0.38 |
| 58 | 0.12 |
| 59 | 0.67 |
| 60 | 0.33 |
| 61 | 0.30 |
| 62 | 0.31 |

The foregoing description is merely illustrative and should not be understood to limit the scope or underlying principles of the invention in any way. Indeed, various modifications of the invention, in addition to those shown and described herein, will become apparent to those skilled in the art from the following examples and the foregoing description. Such modifications are also intended to fall within the scope of the appended claims.

What is claimed is:

1. A compound of formula (I), including pharmaceutically acceptable salts thereof:

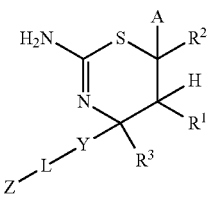

wherein R$^1$ and R$^2$ are independently hydrogen or CH$_3$; or R$^1$ and R$^2$ can join together in a ring by adding —(CH$_2$)$_4$—, R$^3$ is hydrogen or C$_1$-C$_3$ alkyl;

Y and Z are independently a $C_6$-$C_{10}$-aryl group or a 5-10 membered heterocyclic group which can be further substituted with from 0-3 substituents selected from the group of halogen, hydroxy, amino, $C_{1-4}$alkylamino, $C_{1-4}$dialkylamino, halo$C_{1-4}$ alkyl, CN, $C_1$-$C_6$ alkyl or cycloalkyl, $C_1$-$C_6$ alkoxy, —C=O$C_{1-4}$alkyl, —SO$_2C_{1-4}$alkyl, and $C_2$-$C_4$ alkynyl;

A is selected from the group of benzyl, oxazolyl, thiazolyl, isoxazolyl, imidazolyl, pyrazolyl, pyridyl, pyrimidinyl and pyrazinyl and groups which can be further substituted with from 0-3 substituents selected from the group of halogen, hydroxy, amino, $C_{1-4}$alkylamino, $C_{1-4}$dialkylamino, halo$C_{1-4}$ alkyl, hydroxy$C_{1-6}$alkyl, CN, $C_1$-$C_6$ alkyl or cycloalkyl, $C_1$-$C_6$ alkoxy, and $C_2$-$C_4$ alkynyl;

L is —NHCO— or is a single bond;

wherein the Y-L-Z substituent and ring A are trans to each other; and

L and Z together can be absent.

2. A compound of claim 1, wherein $R^1$ and $R^2$ are independently hydrogen or CH$_3$;

or $R^1$ and $R^2$ can join together in a ring by adding —(CH$_2$)$_4$—;

$R^3$ is hydrogen, methyl, or ethyl;

Y is phenyl or thiophenyl and Z is a pyridyl, pyrimidinyl or pyrazinyl group in which either Y or Z group can be further substituted with from 0-3 substituents selected from halogen, hydroxyl, amino, $C_{1-4}$alkylamino, $C_{1-4}$dialkylamino, halo$C_{1-4}$ alkyl, CN, $C_1$-$C_6$ alkyl or cycloalkyl, $C_1$-$C_6$ alkoxy, or $C_2$-$C_4$ alkynyl;

A is selected from the group of benzyl, oxazolyl, thiazolyl, isoxazolyl, imidazolyl, pyrazolyl, pyridyl, pyrimidinyl and pyrazinyl and groups which can be further substituted with from 0-3 substituents selected from the group of halogen, hydroxy, amino, $C_{1-4}$alkylamino, $C_{1-4}$dialkylamino, halo$C_{1-4}$ alkyl, hydroxy$C_{1-6}$alkyl, CN, $C_1$-$C_6$ alkyl or cycloalkyl, $C_1$-$C_6$ alkoxy, and $C_2$-$C_4$ alkynyl;

L is —NHCO— or is a single bond; and

L and Z together can be absent.

3. A compound of claim 2, wherein $R^1$ and $R^2$ are independently hydrogen;

$R^3$ is hydrogen or methyl;

Y is a phenyl or thiophenyl group which can be substituted with from 0-3 halogen, methyl, or trifluoromethyl substituents;

Z is a pyridyl, pyrimidinyl or pyrazinyl group which can be substituted with from 0-3 substituents selected from halogen, CN, or C2-C4 alkynyl;

A is selected from the group of oxazolyl, thiazolyl, isoxazolyl, pyrazolyl, or pyrimidinyl in which each can be further substituted with from 0-3 halogen, $C_1$-$C_6$ alkoxy, halo$C_{1-4}$ alkyl or $C_1$-$C_6$ alkyl substituents;

L is —NHCO— or is a single bond; and

L and Z together can be absent.

4. A compound of claim 3, wherein $R^1$ and $R^2$ are independently hydrogen;

$R^3$ is hydrogen, or methyl;

Y is a phenyl or thiophenyl group which can be substituted with from 0-3 halogen substituents;

Z is a pyridyl, pyrimidinyl or pyrazinyl group which can be substituted with form 0-3 substituents selected from halogen, CN, or $C_2$-$C_4$ alkynyl;

A is isoxazolyl, pyrazolyl, or pyrimidinyl in which each can be further substituted with from 0-3 $C_1$-$C_6$ alkyl substituents;

L is —NHCO— or is a single bond; and

L and Z together can be absent.

5. A compound of claim 4, wherein $R^1$ and $R^2$ are independently hydrogen;

$R^3$ is hydrogen or methyl;

Y is a phenyl or thiophenyl group which can be substituted with from 0-3 halogen substituents;

Z is a pyridyl group which can be substituted with form 0-3 substituents selected from halogen, CN, or $C_2$-$C_4$ alkynyl;

A is isoxazolyl, pyrazolyl, or pyrimidinyl in which each can be further substituted with from 0-3 $C_1$-$C_6$ alkyl substituents;

and L is —NHCO—.

6. A compound of claim 4, wherein $R^1$ and $R^2$ are independently hydrogen;

$R^3$ is hydrogen or methyl;

Y is a phenyl or thiophenyl group which can be substituted with from 0-3 halogen substituents;

Z is pyrimidin-5-yl or pyridin-3-yl or pyridin-5-yl;

A is isoxazolyl, pyrazolyl, or pyrimidinyl in which each can be further substituted with from 0-3 $C_1$-$C_6$ alkyl substituents;

and L is a single bond.

7. A compound of claim 4, wherein $R^1$ and $R^2$ are independently hydrogen;

$R^3$ is hydrogen or methyl;

Y is a phenyl or thiophenyl group which can be substituted with from 0-3 halogen substituents;

A is isoxazolyl, pyrazolyl, or pyrimidinyl in which each can be further substituted with from 0-3 $C_1$-$C_6$ alkyl substituents;

and L and Z together are absent.

8. A compound of claims 1-6, wherein the configuration of the chiral center adjacent to the nitrogen of the aminothiazine is (S).

9. A compound, including pharmaceutically acceptable salts thereof, which is (4S,6S)-4-(2,4-difluorophenyl)-4-methyl-6-(1-methyl-1H-pyrazol-5-yl)-5,6-dihydro-4H-1,3-thiazin-2-amine.

10. A compound, including pharmaceutically acceptable salts thereof, which is (4S,6S)-4-(2,4-difluorophenyl)-4-methyl-6-(3-methylisoxazol-4-yl)-5,6-dihydro-4H-1,3-thiazin-2-amine.

11. A compound, including pharmaceutically acceptable salts thereof, which is (4S,6S)-4-(2,4-difluorophenyl)-4-methyl-6-(pyrimidin-5-yl)-5,6-dihydro-4H-1,3-thiazin-2-amine.

12. A pharmaceutical composition which comprises one or more of the compounds as claimed in claim 1, together with one or more pharmaceutically acceptable carriers, excipients or diluents.

13. A pharmaceutical composition which comprises one or more of the compounds as claimed in claim 5, together with one or more pharmaceutically acceptable carriers, excipients or diluents.

14. A pharmaceutical composition which comprises the compound as claimed in claim 6, together with one or more pharmaceutically acceptable carriers, excipients or diluents.

15. A method for the treatment of disorders selected from Alzheimer's disease, CAA, DLB, ALS, IBM, macular degeneration, traumatic brain injury, Down's syndrome, and inclusion body myositis, which comprises administering to said mammal a therapeutically effective amount of a compound of formula (I) as claimed in claim 1.

16. A method for the treatment of disorders selected from Alzheimer's disease, CAA, DLB, ALS, IBM, macular degeneration, traumatic brain injury, Down's syndrome, and inclusion body myositis, which comprises administering to said mammal a therapeutically effective amount of a compound of formula (I) as claimed in claim 5.

17. A method for the treatment of disorders selected from Alzheimer's disease, CAA, DLB, ALS, IBM, macular degeneration, traumatic brain injury, Down's syndrome, and inclusion body myositis, which comprises administering to said mammal a therapeutically effective amount of the compound of formula (I) as claimed in claim 6.

18. A method according to claim 15 wherein the disorder is Alzheimer's disease.

19. A method according to claim 16 wherein the disorder is Alzheimer's disease.

20. A method according to claim 17 wherein the disorder is Alzheimer's disease.

21. A compound of formula (I), including pharmaceutically acceptable salts thereof:

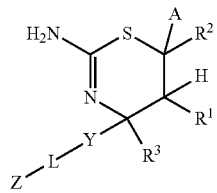

I wherein $R^1$ and $R^2$ are independently hydrogen or $CH_3$; or $R^1$ and $R^2$ can join together in a ring by adding —$(CH_2)_4$—, $R^3$ is hydrogen or $C_1$-$C_3$ alkyl;

Y and Z are independently a $C_6$-$C_{10}$-aryl group or a 5-10 membered heterocyclic group which can be further substituted with from 0-3 substituents selected from the group of halogen, hydroxy, amino, $C_{1-4}$alkylamino, $C_{1-4}$dialkylamino, halo$C_{1-4}$ alkyl, CN, $C_1$-$C_6$ alkyl or cycloalkyl, $C_1$-$C_6$ alkoxy, —C=O$C_{1-4}$alkyl, —$SO_2C_{1-4}$alkyl, and $C_2$-$C_4$ alkynyl;

A is selected from the group of benzyl, oxazolyl, thiazolyl, isoxazolyl, imidazolyl, pyrazolyl, pyridyl, pyrimidinyl and pyrazinyl and groups which can be further substituted with from 0-3 substituents selected from the group of halogen, hydroxy, amino, $C_{1-4}$alkylamino, $C_{1-4}$dialkylamino, halo$C_{1-4}$ alkyl, hydroxy$C_{1-6}$alkyl, CN, $C_1$-$C_6$ alkyl or cycloalkyl, $C_1$-$C_6$ alkoxy, and $C_2$-$C_4$ alkynyl; and L is —NHCO— or a single bond.

22. A compound of formula (I), including pharmaceutically acceptable salts thereof:

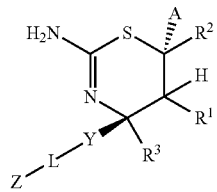

I wherein $R^1$ and $R^2$ are independently hydrogen or $CH_3$; or $R^1$ and $R^2$ can join together in a ring by adding —$(CH_2)_4$—, $R^3$ is hydrogen or $C_1$-$C_3$ alkyl;

Y and Z are independently a $C_6$-$C_{10}$-aryl group or a 5-10 membered heterocyclic group which can be further substituted with from 0-3 substituents selected from the group of halogen, hydroxy, amino, $C_{1-4}$alkylamino, $C_{1-4}$dialkylamino, halo$C_{1-4}$ alkyl, CN, $C_1$-$C_6$ alkyl or cycloalkyl, $C_1$-$C_6$ alkoxy, —C=O$C_{1-4}$alkyl, —$SO_2C_{1-4}$alkyl, and $C_2$-$C_4$ alkynyl;

A is selected from the group of benzyl, oxazolyl, thiazolyl, isoxazolyl, imidazolyl, pyrazolyl, pyridyl, pyrimidinyl and pyrazinyl and groups which can be further substituted with from 0-3 substituents selected from the group of halogen, hydroxy, amino, $C_{1-4}$alkylamino, $C_{1-4}$dialkylamino, halo$C_{1-4}$ alkyl, hydroxy$C_{1-6}$alkyl, CN, $C_1$-$C_6$ alkyl or cycloalkyl, $C_1$-$C_6$ alkoxy, and $C_2$-$C_4$ alkynyl;

L is —NHCO— or is a single bond; and

L and Z together can be absent.

23. A compound of formula (I), including pharmaceutically acceptable salts thereof:

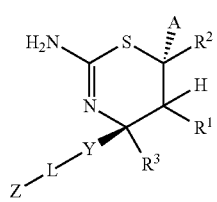

I wherein $R^1$ and $R^2$ are independently hydrogen or $CH_3$; or $R^1$ and $R^2$ can join together in a ring by adding —$(CH_2)_4$—, $R^3$ is hydrogen or $C_1$-$C_3$ alkyl;

Y and Z are independently a $C_6$-$C_{10}$-aryl group or a 5-10 membered heterocyclic group which can be further substituted with from 0-3 substituents selected from the group of halogen, hydroxy, amino, $C_{1-4}$alkylamino, $C_{1-4}$dialkylamino, halo$C_{1-4}$ alkyl, CN, $C_1$-$C_6$ alkyl or cycloalkyl, $C_1$-$C_6$ alkoxy, —C=O$C_{1-4}$alkyl, —$SO_2C_{1-4}$alkyl, and $C_2$-$C_4$ alkynyl;

A is selected from the group of benzyl, oxazolyl, thiazolyl, isoxazolyl, imidazolyl, pyrazolyl, pyridyl, pyrimidinyl and pyrazinyl and groups which can be further substituted with from 0-3 substituents selected from the group of halogen, hydroxy, amino, $C_{1-4}$alkylamino, $C_{1-4}$dialkylamino, halo$C_{1-4}$ alkyl, hydroxy$C_{1-6}$alkyl, CN, $C_1$-$C_6$ alkyl or cycloalkyl, $C_1$-$C_6$ alkoxy, and $C_2$-$C_4$ alkynyl; and L is —NHCO— or a single bond.

* * * * *

UNITED STATES PATENT AND TRADEMARK OFFICE
CERTIFICATE OF CORRECTION

PATENT NO. : 9,475,784 B2
APPLICATION NO. : 14/653025
DATED : October 25, 2016
INVENTOR(S) : Wu et al.

Page 1 of 1

It is certified that error appears in the above-identified patent and that said Letters Patent is hereby corrected as shown below:

In the Claims

Claim 3, Column 99, Line 50:
Delete "C2-C4" and insert -- $C_2$-$C_4$ --.

Claim 4, Column 99, Line 63:
Delete "form" and insert -- from --.

Claim 5, Column 100, Line 8:
Delete "form" and insert -- from --.

Signed and Sealed this
Eighteenth Day of September, 2018

Andrei Iancu
*Director of the United States Patent and Trademark Office*